Figure 1:
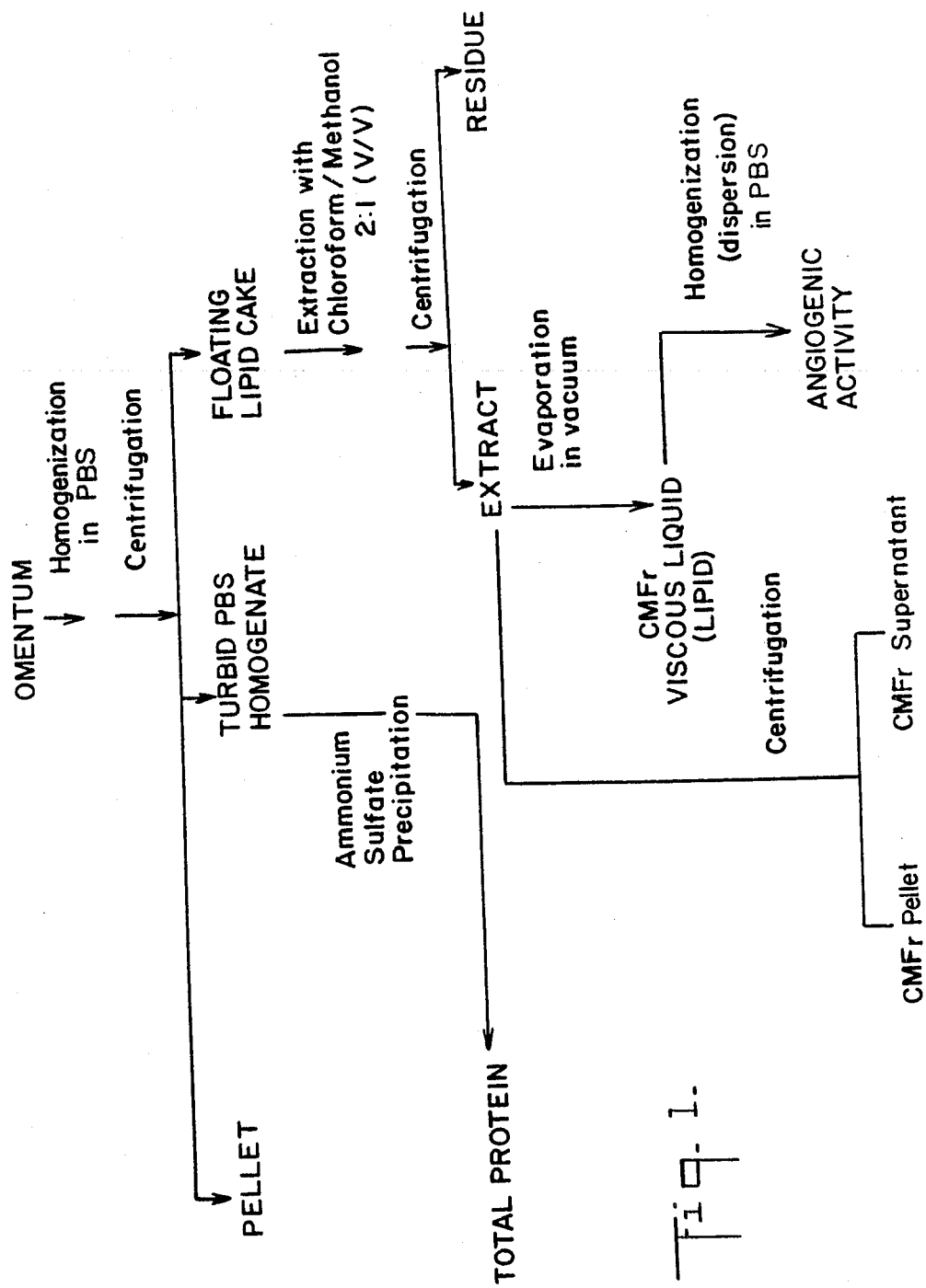

United States Patent [19]

Catsimpoolas et al.

[11] Patent Number: 4,778,787
[45] Date of Patent: Oct. 18, 1988

[54] METHOD FOR TREATMENT OF ANGINA AND MYOCARDIAL INFARCTIONS WITH OMENTAL LIPIDS

[75] Inventors: Nicholas Catsimpoolas, Newton Centre; Haralambos Gavras, Wayland; Christian C. Haudenschild, Newtonville; Michael I. Klibaner, Brookline, all of Mass.

[73] Assignees: Trustees of Boston University, Boston, Mass.; Angio-Medical Corporation, New York, N.Y.

[21] Appl. No.: 811,375

[22] Filed: Dec. 20, 1985

[51] Int. Cl.[4] .................. A61K 31/70; A61K 31/715; A61K 31/20
[52] U.S. Cl. .................................. 514/25; 514/54; 514/558; 424/95
[58] Field of Search ..................... 424/95; 514/25, 54

[56] References Cited

U.S. PATENT DOCUMENTS

| | | | |
|---|---|---|---|
| 2,788,308 | 4/1957 | Ochs | 514/553 |
| 2,845,381 | 7/1958 | Tindall | 514/178 |
| 3,017,325 | 1/1962 | Vogel | 514/185 |
| 3,047,470 | 7/1962 | Pruess | 435/60 |
| 3,271,394 | 9/1966 | Shen et al. | 544/143 |
| 3,318,901 | 5/1967 | Cusic | 435/101 |
| 3,321,484 | 5/1967 | Krimml | 548/402 |
| 3,341,410 | 9/1967 | Ochs | 514/164 |
| 3,395,223 | 7/1968 | Berger et al. | 424/196.1 |
| 3,518,243 | 6/1970 | Butti et al. | 538/395 |
| 3,522,229 | 7/1970 | Yamamoto et al. | 538/395 |
| 3,622,668 | 11/1971 | Moss | 514/168 |
| 3,672,954 | 6/1972 | Grippa | 435/269 |
| 3,767,683 | 10/1973 | Cusic | 260/397.1 |
| 3,809,760 | 5/1974 | Thely | 514/563 |
| 3,920,848 | 11/1975 | Jelenko | 514/552 |
| 3,949,073 | 4/1976 | Daniels et al. | 514/2 |
| 4,029,773 | 6/1977 | Beigler et al. | 514/23 |
| 4,211,782 | 7/1980 | Vane | 514/332 |
| 4,233,360 | 11/1980 | Luck et al. | 428/310 |
| 4,282,250 | 8/1981 | Papageorgiou | 514/547 |
| 4,333,940 | 6/1982 | Shepherd | 175/329 |
| 4,376,781 | 3/1983 | Lietti | 514/458 |
| 4,420,339 | 12/1988 | Kato | 106/124 |
| 4,427,650 | 1/1984 | Stroetmann | 424/46 |
| 4,442,655 | 4/1984 | Stroetmann | 53/428 |
| 4,447,418 | 5/1984 | Maddoux | 424/165 |
| 4,455,298 | 6/1984 | McFarlane | 424/95 |
| 4,456,596 | 6/1984 | Schafer | 514/25 |
| 4,476,119 | 10/1984 | della Valle et al. | 514/25 |

OTHER PUBLICATIONS

K. Huff, et al., J. Cell., Biol., 88:189–198, 1981.
A. Togari, et al., J. Neuro. Sci., 5:307–319, 1985.
L. Greene, et al., Pro. Natl. Acad. Sci., 73:2424–2428, 1976.
G. Landreth, et al., J. Cell Biol., 100:677–683, 1985.
Bremer, E. G., et al., (1984), J. Cell Biol., 259:6818.

*Primary Examiner*—John Rollins
*Attorney, Agent, or Firm*—Felfe & Lynch

[57] ABSTRACT

Angiogenesis healing factors residing in omentum-derived lipid fractions with or without gangliosides or their synthetic equivalents can be used to treat myocardial ischemic conditions including but not limited to myocardial infarction, angina, as well as in heart transplant, vascular grafts, and re-opened vessels leading to improved vascularization, perfusion, collagenization and organization of said lesions; the involved and adjacent tissues.

28 Claims, 30 Drawing Sheets

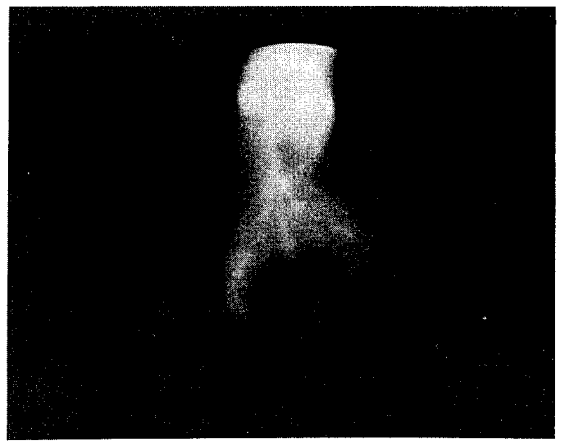
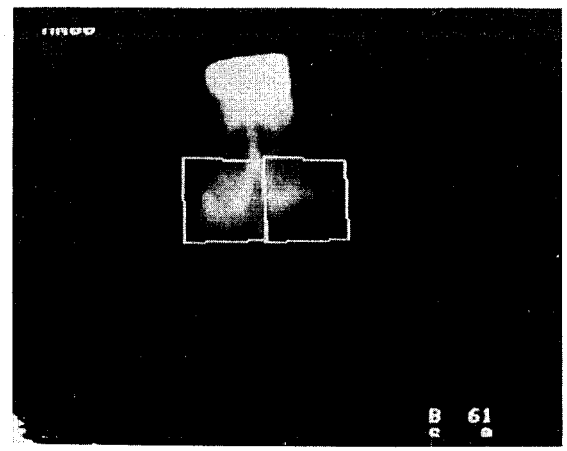
72 Hours
Right Leg
232288 cpm
Left Leg
179831 cpm
29.6 % increase
Fig. 18.

6 Days (post op)
RIGHT LEG        LEFT LEG
159,000 cpm      115,000 cpm
38.2% increase Day 9
RIGHT LEG        LEFT LEG
95909 cpm        57831 cpm
65.8% increase Control #10

Treated #11

Control #10

Treated #11

Control #10

Treated #12

Control #10

Treated #11

Control #7

Treated #8

Control Dog #10

Control #10

Experimental #12

Treated #11

Treated #12

METHOD FOR TREATMENT OF ANGINA AND MYOCARDIAL INFARCTIONS WITH OMENTAL LIPIDS

SUMMARY

Angiogenesis healing factor(s) residing in an omentum-derived lipid fraction are used to treat myocardial ischemic conditions including but not limited to myocardial infarction (MI), angina, heart transplants and hearts with vascular grafts or recanalized coronary arteries with the purpose of improving vascularization, perfusion and organization of the involved and adjacent tissues.

DESCRIPTION

Heart attacks are a major cause of death and the overall mortality rate during the first months after MI average 30%. Most of the deaths occur in the first 12 hours.

Myocardial infarction is ischemic necrosis due to occlusion or substantial narrowing of a coronary artery by thrombus, or by atherosclerosis, or by hemorrhage into an atherosclerotic plaque, or by spastic constriction, or by a combination of these mechanisms.

Treatment for myocardial infarction has largely been one of containment and stabilization for a patient. Symptoms are treated and no therapy is available to help rebuild the damaged vascular or myocardial system. Various discussions in medicine can be cited. As for example, Krupp et al. Current Medical Diagnosis and Treatment, 1985 Lange Medical Publications, Los Altos, Calif., as typical, discusses this on P. 121 et seq.

Current treatment consists of rest; sedation; pain-killers (analgesics); oxygen; anticoagulants and/or thrombolytic agents such as streptokinase or TPA (tissue plasminogen activator); systemic vasopressors; diuretics; local vasodilators such as nitroprusside, nitroglycerine, inotropic agents such as digitalis; aortic balloon counterpulsation as a circulatory assist and, recently, reopening of the acute occlusion by balloon catheters and similar devices (angioplasty), or bypass surgery. No therapy exists for cardiac rupture save surgery and that only in cases where the leak is slow. Sulfinpyrazone (Anturane) is shown to counter platelet aggregation and has an effect to prevent recurrent myocardial infarctions up to seven months. Beta-adrenergic blocking drugs also decrease the likelihood of reinfarction in the months following acute myocardial infarction; such drugs include limolol, propranolol, alprenolol and metoprolol.

Rehabilitation goals include early return to some physical and progressive activities, acceptable quality of life and possibly gainful employment.

Most of these current treatments are symptomatic and do not address the basic damage. Even the most modern interventive approaches (thrombolysis, angioplasty or bypass surgery) reperfuse inflow, i.e. the large vessels, but do not increase the capillary vessels or outflow or collateralization. Sometimes, increased inflow without appropriate capillary drainage leads to an undesirable condition known as "reperfusion damage". Methods and materials are needed to enhance and/or accelerate basic healing mechanisms to promote perfusion, neovascularization and scarring, collagen formation. This is the method of the invention wherein the above healing mechanisms including neovascularization as well are seen in mammalian myocardial infarctions.

The present invention uses systemic (and/or local) application of omentum-derived lipid fractions or the use of their bio- or organic-synthetic or purified analogues for the acceleration of vascularization, neovascularization, vascular collateralization, promotion of perfusion, and collagen formation or scarring, and organization (cellular and collagenous) of myocardiac ischemic lesions. This is a surprising result since lipid materials are more regarded as atherosclerotic agents. U.S. Pat. No. 4,296,100, issued Oct. 20, 1981 to Wayne P. Franco, reports on a protein fibroblast growth factor which is used by direct injection into the heart, and has what appears to be a preventive effect regarding the area affected by MI. In wound healing, one can see an agent which promotes healing after vascularization or there is dicussion of agents which may promote vascularization. It is surprising to see material as in the present invention which promotes both vascularization and cellular/collagenous organization in vivo especially as a local effect at the lesion site in response to systemic application.

The following 4 applications can be cited as examples for treatment of heart conditions:

1. Treatment of acute myocardial infarction with the goals of rapid and effective neovascularization of the lesion and adjacent border zones, salvage of a maximal number of partially injured heat muscle cells, rapid access of living repaired cells to the damaged tissue and accelerated formation of a mechanically stable scar.
2. Treatment of general myocardial ischemia (angina) by permanent increase of overall vascularization and collateralization allowing improved myocardial perfusion.
3. The improvement of vascularization and perfusion of transplanted hearts.
4. The improvement of the vascular beds supplied by coronary, aortic and peripheral vascular grafts and or reopened coronary arteries (by angioplasty, thrombolysis and similar interventive procedures) in order to minimize graft outflow obstruction and to increase the chance of salvaging the affected limbs or organs.

"Increased vascularization" can be defined by "increased number of effective (or open) large and small vessels, including capillaries, per unit volume of tissue".

"Increased perfusion" can be defined by "improved blood flow to, through and from a specific vascular bed". This can be achieved by better opening and accelerated flow through existing vessels, or by the formation of additional new vessels (angiogenesis), or both.

Increased myocardial vascularization is a desirable therapeutic goal since it leads to stimulation of small blood vessel growth and perfusion in:

(1) hearts with focally insufficient blood supply caused by severe narrowing of one or more coronary arteries or their major branches, typically by arteriosclerotic lesions and their complications (ischemic myocardium, angina patients) and,
(2) myocardial infarcts where the lack of sufficient coronary blood supply has led to focal myocardial cell death and,
(3) transplanted hearts where existing blood vessels may be damaged and,
(4) hearts with vascular by-pass grafts or reopened coronary arteries (by interventive procedures mentioned before), to assure optimal distribution of the restored blood flow (similar argument also in other organs and limbs supplied by vascular grafts).

The spontaneous healing of a myocardial infarct is associated with increased vascular perfusion and involvement of a number of living cells with specific functions in the sequence of repair. Such cells are mainly brought to the site through vessels include: polymorphonuclear leukocytes, macrophages, vascular cells (endothelium, pericytes, smooth muscle; involved in angiogenesis), and fibroblasts.

The specific aim is the enhancement of these vascular processes by systemic (or local) application of novel omentum-derived vascular growth factors, in order to improve the vascularization and perfusion of the diseased myocardium and its border areas, and to accelerate and promote in this manner the salvage of most possible contractible cells, the access of cells involved in organization and repair, and early formation of an organized collagenous replacement tissue of adequate tensile strength.

These results can be obtained by local, systemic or perfusion of the affected area with omentum-derived angiogenic lipid fractions.

The extraction of cat omentum is described in a copending U.S. application Ser. No. 642,624, now a U.S. Pat. No. 4,699,788, issued Oct. 13, 1987, which is hereby incorporated by reference. There is also a publication concerning angiogenesis factor from omentum "Lipid Angiogenesis Factor From Omentum" by Harry S. Goldsmith et al. (1984) J. Amer. Med. Ass'n. 252: 2034 which is hereby incorporated by reference. These is a further patent application "Composition Containing Lipid Molecules with Enhanced Angiogenic Activity" Ser. No. 782,724, filed Oct. 1, 1985, now U.S. Pat. No. 4,710,490, which is hereby incorporated by reference. The lipid preparation obtained from the omentum of animals was the result of an extraction using at least one organic solvent. The angiogenic material obtained by this process from the omentum is abundant in supply, and contains at least one potent angiogenic factor which will cause the development of numerous neovascular connections in living tissue. The lipid preparation itself is heterogeneous in composition and has been found to contain at least five lipid subfractions which interact with one another to provide the most potent angiogenic effect.

The angiogenic material is used in would healing experiments in a copending application by Robert Sinn and Nicholas Catsimpoolas Ser. No. 805,206, filed Dec. 4, 1985 and hereby incorporated by reference.

We also note the use of the angiogenic omentum material in bone healing in our copending application Ser. No. 811,894, filed Dec. 20, 1985, and in skin conditions Ser. No. 811,505, filed Dec. 20, 1985, hereby incorporated by reference.

EXAMPLE I

I. Obtaining the Chloroform Methanol Lipid Containing (CMFr) Fraction

Adult female cats weighing 2.4–3.2 kg. were anesthetized by an intramuscular injection of Ketamine at a preferred dosage of 7.0 mg/kg. Once anesthetized, a laparotomy was performed through a mid-line incision according to conventionally known surgical procedures. Omenta were surgically removed and placed into sterile plastic bags held at 4° C. for immediate processing. Simultaneously, subcutaneous fat was also removed and treated in a manner identical to the omental tissue for use in procedures as a non-omental lipid control. Using proper aseptic technique, the omenta were weighed, spread out onto a plastic surface and cut into individual pieces approximately four square centimeters in size using surgical scissors. These individual omental pieces, ranging in weight individually from 7 to 66 grams, were placed in a sterile Waring blender containing 300 ml of phosphate buffered saline (hereinafter "PBS") which was precooled to 4° C. The omental pieces were blended for five minutes at 20,500 rpm to yield an omental homogenate which was subsequently placed in sterile 250 ml plastic bottles and centrifuged at 1600 times gravity in a refrigerated centrifuge at 4° C. for twenty minutes. After centrifugation, three distinct and separable fractions were visible in the bottles: a pellet of mixed composition; a turbid homogenate containing substantially all the proteinaceous material, and a floating, cream colored, lipid cake. Each of these fractions was isolated individually.

The pellet of mixed composition was discarded completely. The turbid homogenate fraction was fully saturated (i.e. 100%) with aqueous ammonium sulfate which acted to precipitate the total protein in this fraction. Testing of the turbid homogenate fraction and the total protein precipitant (resuspended in PBS) by the cornea assay revealed that neither of these preparations had good angiogenic activity.

The lipid fraction isolated as a floating lipid cake was composed of two distinct layers: an upper foamy composition and a more dense, compact layer which was darker in color than the upper. Each layer was evaluated and found to contain an active angiogenic factor in substantial quantity. For this reason, each of these lipid layers individually and in combination comprise the active lipid fraction. The weight of the lipid cake comprising both layers was found to be approximately 93% of the total weight of the omentum from which it was derived and it is this lipid cake which is used to prepare the concentrated organic extract comprising the active angiogenic factor composition.

Active lipid fractions were extracted using the quantities and proportions of lipid cake given in Table I:

TABLE I

| Exp. No. | Total Omentum* | Lipid Cake* | Portion of Lipid Cake Extracted* |
|---|---|---|---|
| 1 | 31.2 | NR | 3.6 |
| 2 | 65.7 | 56.0 | 3.2 |
| 3 | 50.1 | 48.3 | 3.1 |
| 4 | 61.0 | NR | 7.1 |
| 5 | 38.0 | 37.0 | 3.5 |
| 6 | 39.5 | NR | 3.0 |
| 7 | 7.8 | 6.2 | 2.4 |
| 8 | 22.3 | 21.4 | 3.4 |

*Weight (gm)
NR = Not Reported

The indicated quantities of lipid cake were combined with approximately 21 ml of an organic solvent comprising chloroform and methanol (2:1, v/v) in an Eberbach 8575 microblender and homogenized for two minutes. The lipid/organic solvent homogenate was then centrifuged at 200 times gravity in a clinical centrifuge at room temperature for ten minutes to yield a clear, golden colored, supernatant and a particulate matter precipitate. The supernatant was isolated using coventional procedures and subjected to rotary evaporation at 37° C. under vacuum to completely remove the chloroform/methanol solvent. Other methods for solvent removal are known in the art and may be used in place of rotary evaporation. A viscous liquid was obtained which was then preferably suspended in approximately 4 ml of PBS for use in the cornea and cam assays.

II. Obtaining Purified Fractionates

The CMFr, obtained supra, was dissolved in a mixture of hexane (approx. 60 ml hexane for every 10 g of extract), and 0.66 volumes of 95% ethanol was then added. The phases were mixed thoroughly, and were allowed to separate. The upper phase (hexane), was re-extracted with 95% ethanol, and the resulting lower phase of the re-extraction was combined with the first ethanol fraction. The combined ethanol fractions were then re-extracted with hexane, and the resulting hexane layer combined with the first hexane fraction. Both phases were dried, to obtain "hexane upper phase material," and "ethanol lower phase material" (hexane-UP, and ethanol-LP, hereafter).

The ethanol-LP fraction was then subjected to Folch partition, following Folch, et al., *J. Biol. Chem.* 226: 497-509 (1957) (i.e., the fraction was dissolved in chloroform/methanol (2:1, 20 volumes, v/wt), and 0.2 volumes of water were added. Phases were thoroughly mixed, and allowed to separate). The upper phase of the Folch partition was removed, and the lower partition was washed with 0.4 volumes methanol/water (1:1). This produces an upper methanol phase, which is combined with the Folch upper phase, and then dried to obtain the portion known hereafter as "Folch UP." The lower portion is also dried, and is known hereafter as "Folch LP."

The Folch LP portion was dissolved in chloroform, and was then subjected to chromatography on a silicic acid, Unisil column, as described by Vance, et al., *J. Lipid Res.* 8: 621-630 (1967). The column was eluted successively with 20 column volumes of chloroform, acetone/methanol, (9:1), and methanol. This successive elution separates neutral lipids (chloroform), glycolipids (acetone/methanol), and phospholipids (methanol).

The Folch UP portion was dissolved in approximately 3 ml/mg of methanol/water (1:1), and was then applied to a C18 reversed-phase cartridge, as described by Williams, et al., *J. Neurochem.* 35 (1): 266-269 (1980), and the cartridge was then washed with four volumes of methanol/water (1:1) to obtain "non-lipid UP material" after drying, and four volumes of chloroform/methanol (2:1), to obtain "lipid UP material" after drying.

Lipid UP material was then dissolved in methanol/chloroform/water (60:30:8), and was applied to a DEAE-Sephadex acetate column, following Christie, *Lipid Analysis,* Pergamom Press, 2nd edition, pp. 109-110 (1982). This column was then eluted with 10 volumes of the methanol/chloroform/water mixture used originally, to obtain what is referred to as "neutral lipid upper phase fraction," or "neutral lipid UP." Extraction with methanol/chloroform/0.8 sodium acetate (60:30:8) obtained ganglioside fractions. Both fractions were evaporated to dryness, and the glucoside fraction was desalted, using a C18 reversed phase cartridge.

The chloroform-methanol fraction was extracted with 1.0% acetic acid in a volume ratio of 1:10 (w/v) by stirring with a magnetic stirrer for 10-12 minutes. The extract was centrifuged at 2000 rpm for 5 minutes in 200 ml bottles. The top layer, i.e., the acetic acid-insoluble fraction was then removed. The acetic acid soluble fraction was combined with an equal volume of chloroform and was centrifuged as above to obtain a clean separation of the two phases. Each phase was backwashed twice with the opposite solvent and all chloroform phases were pooled. Evaporation of the chloroform yielded the "acetic acid soluble" fraction.

Affinity chromotography (heparin and gelatin binding) of the Folch UP and "PBS homogenate" fractions were performed as follows:

Heparin-Sepharose CL-6B beads or Gelatin-Sepharose beads (approximately 3 gm each) were washed with 450 ml water in a sintered glass filter. The sepharose beads were suspended in water and packed into a 2.5×9 cm chromatography column. Excess water was drained off and the dry sample (e.g., Folch-UP) was suspended in 0.01 phosphate buffer, pH 7.0 and applied to the column. Elution was performed with the same buffer (total 100 ml at a flow rate of 2 ml per minute). This was followed by a washing with 100 ml of water to remove salts from the column. Final elution of the heparin or gelatin binding material was performed with 50 ml of 0.5% acetic acid. After evaporation of acetic acid the material was resuspended in phosphate buffer for testing.

The chloroform/methanol (2:1 v/v) lipid fraction was further characterized as to its component parts or subfractions using silica gel or iatrobead liquid chromatography. For these chromatographic fractionations the procedures described in A. Kuksin, *Chromatography Part B'* (E. Heftmann, editor), Elsevier, New York, 1983, were used. In our method, 5.0 ml of the chloroform/methanol lipid extract was placed in a chromatography column containing silica gel (100-200 mesh Sigma Chemical Company) which was previously equilibrated with chloroform. Using the silica gel columns, elutions was performed in sequence using 100 ml aliquots of the following solvents: chloroform; ethyl acetate; ethyl acetate/methanol (3:1); methanol/water (4:1) followed by 200 ml of a solvent mixture comprising chloroform/methanol/-acetic acid/water (25:15:4:2). Five individual elution fractions were obtained (I-V).

Gel permeation chromatography was performed on a Sephadex LH-20 column. One hundred mg of the chloroform-methanol extract, or of the ethanol-LP were placed on the column and elution was corned out with a chloroform-methanol (1:1) solvent. Fractions were collected and the solvent was evaporated for testing.

III. Analysis of the Fractions

The lower phase glycolipids were examined by HPTLC with chloroform/methanol/water (60:35:8) as the developing solvent and visualized with the orcinol spray reagent as described by Svennerholm, *J. Neurochem.* 1:42 (1956). They were also analyzed by HPLC as their perbenzoyl derivatives as previously reported by Ullman, et al., *J. Lipid Res.* 19: 910-913 (1978). The upper phase complex neutral glycolipid fraction was examined by HPTLC and by immunoblotting with Forsmann and SSEA-1 antibodies. The major component of the upper phase complex neutral glycolipid fraction was further purified by preparative TLC or by chromatography on an Iatrobead column (1×50 cm, 60 u) eluted with hexane/isopropanol/water mixtures as taught by Kannagi, et al., *J. Biol. Chem.* 237(24) 14865-14874 (1982); and Hakomori, et al., *J. Biol. Chem.* 259(7) 4672-4680 (1984).

The ganglioside fraction was treated with 0.25N sodium hydroxide in methanol for 2 hrs at 37° C., neutralized with glacial acetic acid and desalted with a C18 reversed-phase cartridge. The alkali treated ganglioside fraction was then subjected to chromatography on a DEAE-Sephadex column and eluted with 0.02M, 0.08M and 0.05M ammonium acetate in methanol to obtain mono-, di-, and polysialo-ganglioside fractions, respectively. See Ledeen, et al., *Methods in Enzymol.* v. 83, part D, pp. 139–191 (1982). The ganglioside fractions were separated into individual components by chromatography on a 0.4×50 cm, 10 uM particle, Iatrobead column eluted with chloroform/methanol/water (65:35:8). Fractions of 1.2 ml were collected, aliquots examined by HPTLC and fractions containing single components appropriately pooled. The non-lipid material was extracted with methanol, centrifuged and the supernatant removed. The insoluble residue was dissolved in water, and the water and methanol soluble fractions examined by HPTLC in several solvent systems.

Purified gangliosides were dried under nitrogen, and 300 ul of 0.05M sodium acetate buffer, pH 5.5, containing 0.025% $CaCl_2$ added. *V. cholerae* neuramindase (100 ul, 0.1 units, where ul=microliter) was added and the sample incubated for 3 hrs at 37° C. The reaction was stopped by the addition of 2 ml chloroform/methanol (2:1) and the mixture was placed over a reversed phase cartridge and the non-lipid components eluted with water. Any remaining gangliosides and lipid reaction products were eluted with methanol and chloroform/methanol and examined by HPTLC. The liberated sialic acids were also examined by TLC as their trimethylsilyl derivatives following Ledeen, supra.

For sugar and fatty acid analysis, the glycolipids were subjected to methanolysis in anhydrous 0.75N HCl in methanol following Ledeen, supra, and Kozulec, et al., *Analytical Biochem* 94: 36–39 (1979). The fatty acid methyl esters were analyzed by TLC. The methyl glycosides were analyzed as their trimethylsilyl derivatives on the same OV-1 column as described by Kozulec, supra. For HPTLC analysis of the lower phase neutral glycolipids, the fraction was perbenzoylated with benzoyl chloride in pyridine and the benzoylated glycosphingolipids separated and quantitated by HPLC on an uncoated Zipax column with gradient elution and 230 nm detection as previously described by Ullman, supra. For direct probe mass spectrometry, glycolipid or ganglioside samples (5–50 ug) were trimethylsilylated in 25 ul of pyridine/hexamethyldisilane/trimethylchlorosilane/N,O-bistrimethylsilyltrifluoro acetamide. Anywhere from 1 to 5 ug (where ug=microgram) of the derivative was placed in a sample cup and the probe was heated from 100° to 350° C. at a rate of 30°/min. The mass spectra were obtained with a Finnigan model 4500 quadrupole mass spectrometer equipped with Teknivent, model 56K data system. It was operated with an ionizing current of 0.5 ma and an ionizing voltage of 70 eV. The ionizer temperature was 150° C. Repetitive scans of the mass range from 100 m/e to 950 m/e were acquired at 5 sec intervals.

Glycolipids were chromatographed on aluminum-backed HPTLC plates with chloroform-methanol-water (60:35:8), dried, then dipped in 0.05% polyisobutyl methacrylate in hexane as described by Brockhause et al, *J. Biol. Chem.* 256: 13223–13225 (1981). The plates were then soaked in phosphate buffered saline containing 1% bovine serum albumin for 2 hours before similar exposure to antibody for 2 hours at 40° C. The plate of upper phase neutral glycolipid was treated with Forssman monoclonal antibody IgM, purchased from American Type Culture Collection (TIB 121). The TLC plates of the disialoganglioside fraction was treated with GD3 monoclonal antibody IgM prepared by the inventors. After washing in PBS the plates were exposed to goat anti-mouse IgM conjugated to horseradish peroxidase for 2 hours at 4° C. After washing in PBS, the plates were developed with 33 mN 4-chloronaphthol in 0.02M Tris-HCl buffer containing 20% methanol and 0.025% $H_2O_2$.

IV. Characteristics of the Fractions

Figure 2:
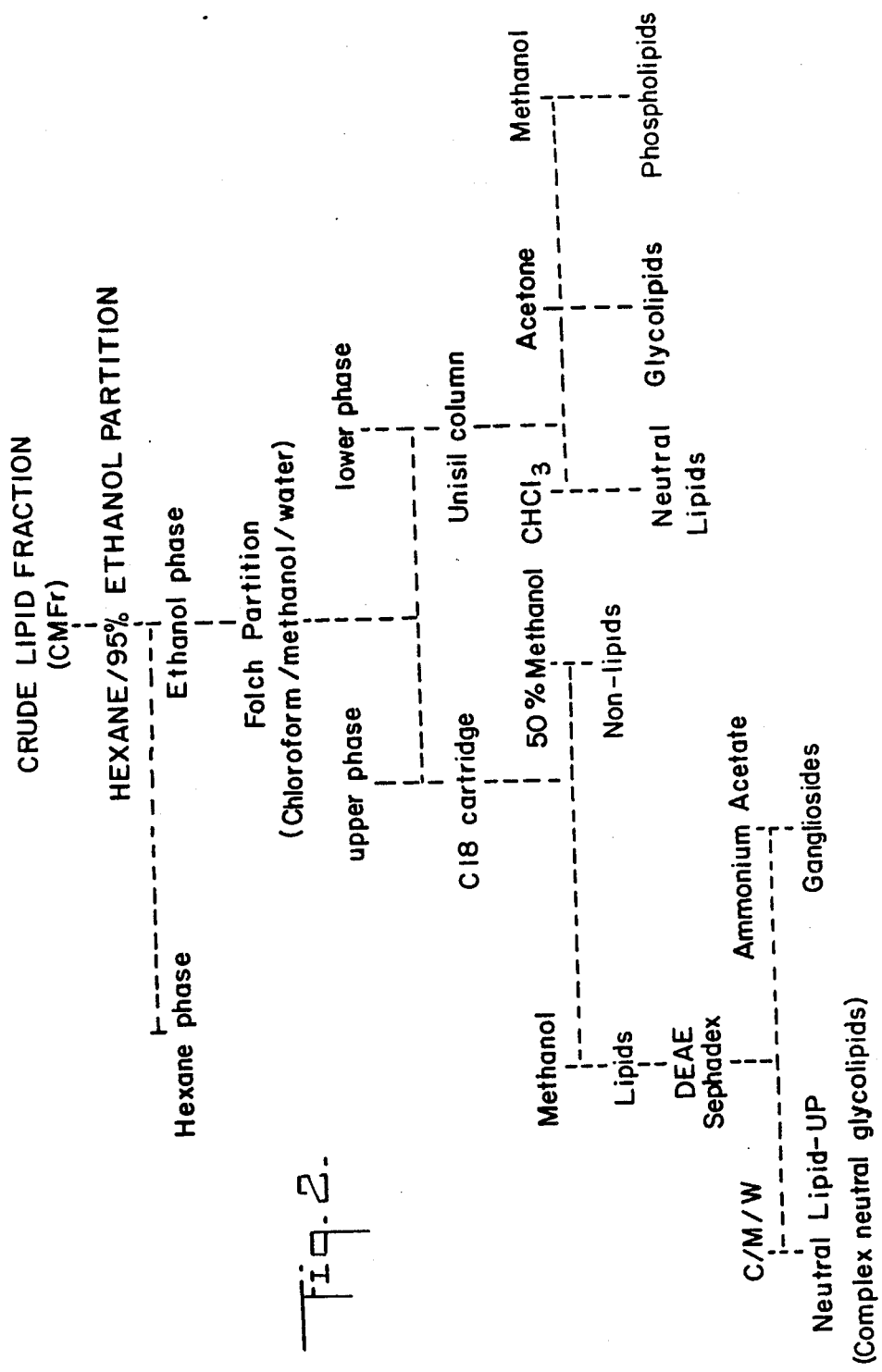

Feline omentum was homogenized, centrifuged and the floating lipid cake was extracted with chloroform/methanol and further fractionated as shown in FIG. 2. The hexane phase contained approximately 98% of the material in the CMFr and was shown to consist primarily of triglycerides, as determined by TLC. Alkaline methanolysis and GC/MS analysis of the resulting fatty acid methyl esters revealed that 14:0, 16:0, 16:1, 17:0, 18:0, 18:1 and 18:2 were the major triglyceride fatty acids (i.e., the first number indicates that carbon chain length of the fatty acid, the second the number of unsaturated bonds).

The ethanol phase material was subjected to Folch solvent partition and the lower phase lipids, which constituted 80% of the ethanol phase lipids, were fractionated on a Unisil column. The neural lipid fraction recovered from the Unisil column also consisted primarily of triglycerides and small amounts of cholesterol and free fatty acids were detected by TLC analysis. The acetone glycolipid fraction was examined by TLC and components migrating as hexosylceramide, lactosylceramide, globotriaosylceramide and globoside were present. Quantitative analysis of these glucolipids by HPTLC is described infra. The methanol phospholipid fraction was examined by TLC and components migrating as phosphatidylserine, phosphatidylcholine and sphingomyelin were present.

Approximately 20% by weight of the ethanol-phase material was recovered by the Folch-UP. This Folch-UP material was applied to a reversed-phase cartridge and the non-lipid fraction eluted with methanol-water and the lipids eluted with chloroform/methanol. The lipid-UP material, was applied to a DEAE column and the neutral lipid fraction, which was not retained by the column, was collected and found to constitute 40% of the lipid-UP material. Upon examination by HPTLC this fraction was found to contain primarily a glycolipid migrating below globoside, and small amounts of more complex glycolipids.

The ganglioside fraction was eluted from the DEAE column with ammonium acetate in methanol and desalted with the use of a reversed phase cartridge. Examination by HPTLC revealed the presence of resorcinol components migrating as GM3, GM1, GD3 and several minor polysialoganglioside components. The further purification and identification of these gangliosides is described infra.

The non-lipid upper phase fraction (non-lipid-UP) was taken to dryness and extracted with methanol. The majority of material was not methanol soluble and the suspension was centrifuged and the supernatant removed. The insoluble material was readily soluble in water. These fractions were examined by TLC and the water soluble fraction showed only one ninhydrin positive band. The bulk of this water soluble material appeared to be salt. The methanol soluble material contained at least six orcinol and ninhydrin positive components and a GC/MS analysis, after trimethylsilylation, indicated this material was a complex mixture of sugars, amino acids, peptides and glycopeptides. Weight distribution of the fractions from the omentum crude lipid extract is shown in Table II.

Figure 3:
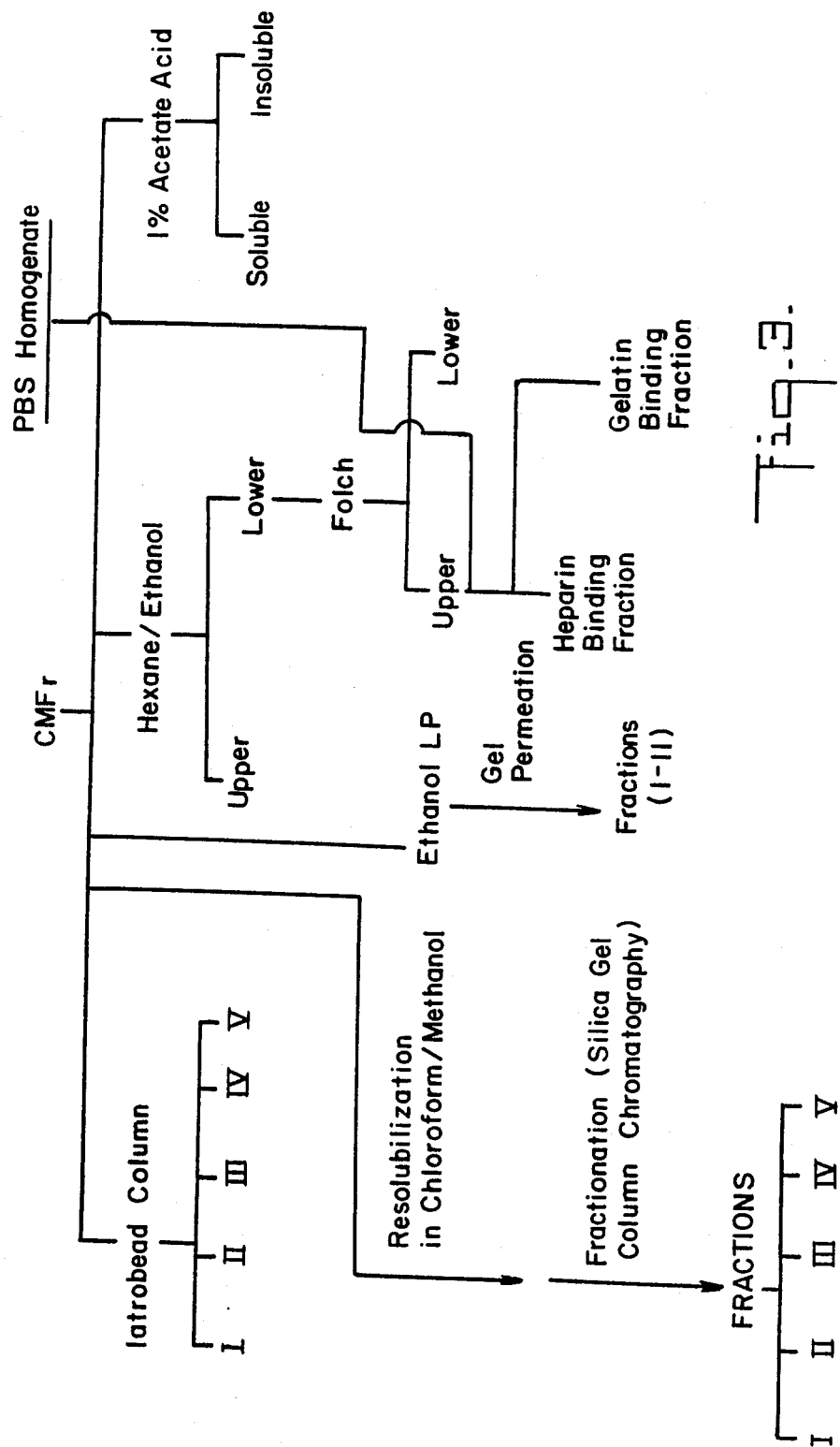

Aliquots of the glycolipid fraction were benzoylated with benzoyl cloride in pryidine and the perbenzoylated derivatives analyzed by HPLC with 230 nm detection. The results are shown in FIG. 3. These data show that the percent distribution of glycolipids in this fraction as GlcCer (Nfa), 26%; GalCer (Nfa), 9.6%; GlcCer (Hfa)+GalCer (Hfa)+GaOse2Cer (Nfa), 12%; LacCer, 11%; GbOse3Cer, 10%; GbOse4Cer, 26%.

The upper phase neutral lipid fraction was examined by HPTLC and found to consist of about 90% of an orcinol positive material migrating slightly more slowly than the globoside standard, as well as small amounts of 3 to 4 more polar orcinol positive components. Immunoblotting with Forsmann and SSEA-1 antibody indicated the major component was Forsmann positive and no SSEA-1 positive components were present. The major component was further purified by chromatography on an Iatrobead column and subjected to methanolysis and component analysis by GC/MS. Hexose ratios were found to be Glc/Gal/NaCGal 1:2:2. Fatty acids were present. The intact glycolipid was also silylated and examined by direct probe mass spectrometry. The spectra, show in FIG. 3, indicated the presence of terminal hexosamine, internal hexose residues, the presence of C-18 sphingosine and fatty acids. Taken together these data indicate that the glycolipid is the Forsmann pentaglycosylceramide. Although position and configuration of linkages have not been directly determined, the antibody reactivity and glycolipid analytical data strongly support this structure.

The ganglioside fraction was treated with mild alkali to destroy any ester linkages that may have been present and separated into mono, di and polysialoganglioside fractions by DEAE-Sephadex chromatography. The monosialoganglioside fraction was shown by HPTLC to consist primarily of components migrating as a triplet of bands corresponding to the mobility of the GM3 standard and a small amount of material migrating as GM1. The monosialoganglioside fraction was further purified by chromatography on an Iatrobead column and the fractions containing only components migrating as GM3 were pooled. This material was treated with neuraminidase and the lipid product was characterized as lactosylceramide by HPTLC and direct probe-MS. The liberated sialic acid was shown by GC analysis to consist only of N-acetylneuraminic acid. The intact ganglioside was subjected to methanolysis and the sugars and fatty acids examined by GC analysis. The ratio of Glc/Gal was found to be 1:1 and the fatty acids consisted of primarily of 16:0, 18:0, 18:1, 20:0, 22:0, 23:0, 24:0 and 24:1. The preparation was also examined by direct probe mass spectrometry as the trimethylsilyl ether derivative. A mass spectra similar to that given by ganglioside GM3 standard (sialyl[2-3]galalctosyl[1-4]glucosy[1-1]ceramide).

The disialoganglioside fraction was shown by HPTLC to consist primarily of a component migrating as GD3. This material was further purified by chromatography on an Iatrobead column and the fractions containing only a single component migrating as GD3 were pooled. The preparation was subjected to methanolysis and the methyl glycosides and fatty acid methyl esters examined by GC/MS. The ratio of Glc/Gal was found to be 1:1 and the major fatty acid components were 16:0, 18:0, 18:1. 24:0, 24:1. The material was treated with neuraminidase and the lipid product identified as lactosylceramide by HPTLC and direct probe MS analysis. The liberated sialic acid was shown to consist only of N-Acetylneuraminic by GC analysis. Direct probe MS of the TMS derivative gave spectra consistent with GD3. The material was also shown by immunoblotting to react with a monoclonal antibody prepared in this laboratory with demonstrated reactivity with GD3.

The polysialoganglioside fraction was shown to contain components migrating on HPTLC as ganglioside GD1a, GT1b, but insufficient quantities were obtained for further analysis.

V. Angiogenesis

The angiogenic activity of the lipid preparations described in FIG. I and of the Silica Gel chromatography fractions I-V were tested by the rabbit cornea test in the following manner: a series of New Zealand white rabbits were anesthetized with intravenous pentobarbitol (30 mg./Kg). From each preparation shown in Table I, a single 50 microliter injection of the aqueous lipid suspension was made through a 25 gauge needle placed intrastromally into the cornea of each eye. The corneas of the animals were examined grossly and with an operating microscope on the second, fourth, sixth, eighth, and tenth day following ocular injection. Blood vessel growth and the presence of any corneal edema and/or inflammation was noted. On the tenth day after examination visually, the rabbits were individually sacrificed and histological slides, stained with hematoxylin and eosin in the conventional manner, were obtained from six micrometer thick sections cut from the formalin fixed enucleated eyes. Photo records of positive rabbit eyes were recorded.

The angiogenic response was graded as follows: 0, identified no angiogenesis and a clear cornea; 1+, identified dilation of scleral vessels with red coloration noted at the limbus; 2+, identified several individual blood vessels migrating from the limbus two thirds of the way to the injection site; 3+, identified multiple blood vessels extending from the limbus to the injection site involving 10–20% of the cornea; 4+, identifies dense blood vessel formation extending from the limbus to the injection site involving at least 30–40% of the cornea.

For comparison purposes, an aqueous suspension of the omental lipid cake and an aqueous preparation of the subcutaneous non-omental fat were also prepared and tested. The non-omental fat preparation was made by combining a three gram portion of the fatty subcutaneous tissue with 4 ml of PBS and homogenizing this mixture using the Eberbach microblender for two minutes at 4° C. Similarly, an aqueous suspension of the omental lipid cake was prepared by homogenizing four gram portions of the lipid cake with 4 ml of PBS in the microblender for two minutes at 4° C. The homogenate of the whole omentum prior to centrifugation into proteinaceous fractions and lipid fractions was also evaluated. The results are as shown in Table II below.

TABLE II

| Test Sample | | Angiogenic Activity (per 50 microliter) |
|---|---|---|
| 3 | Extracted | |
| 4 | lipid preparation | |

TABLE II-continued

| | Test Sample | | Angiogenic Activity (per 50 microliter) |
|---|---|---|---|
| 5 | in aqueous | | |
| 6 | medium - | No. 1 | 4+ |
| 7 | | No. 2 | 4+ |
| 8 | | No. 3 | 3+ |
| 9 | | No. 4 | 4+ |
| 10 | | No. 5 | 3+ |
| 11 | | No. 6 | 4+ |
| 12 | | No. 7 | 4+ |
| 13 | | No. 8 | 4+ |
| 14 | PBS homogenate | | |
| 15 | of lipid cake | No. 1 | +1 |
| 16 | | No. 2 | +1 |
| 17 | | No. 3 | +1 |
| 18 | PBS homogenate | | |
| 19 | of whole omentum | No. 1 | +1 |
| 20 | | No. 2 | +1 |
| 21 | | No. 3 | +1 |
| 22 | PBS homogenate | | |
| 23 | of non-omental | | |
| 24 | fatty tissue | No. 1 | 0 (inflammation) |
| 25 | | No. 2 | 0 (inflammation) |
| 26 | | No. 3 | 0 (inflammation) |
| 27 | PBS alone | No. 1 | 0 |
| 28 | | No. 2 | 0 |
| 29 | | No. 3 | 0 |

The data indicates that excellent angiogenic activity was observed after a single 50 microliter central corneal injection of the chloroform/methanol lipid extract CMFr. In comparison, only minimal angiogenic activity was noted with the PBS homogenate of the total omentum and with the PBS homogenate of the total omentum and with the PBS homogenate of the lipid cake prior to extraction. Note, however, that a heparin binding component was concentrated by affinity chromatography from the PBS homogenate which showed good angiogenic activity with the CAM assay (see Table III). No angiogenesis at all occurred in those instances following injection of PBS alone or the subcutaneous non-omental fat PBS homogenate. A complication however, noted in the data of Table II, was that the injected subcutaneous fat taken from the cat abdominal wall caused severe inflammation of the cornea within two days after corneal injection.

Figure 4:
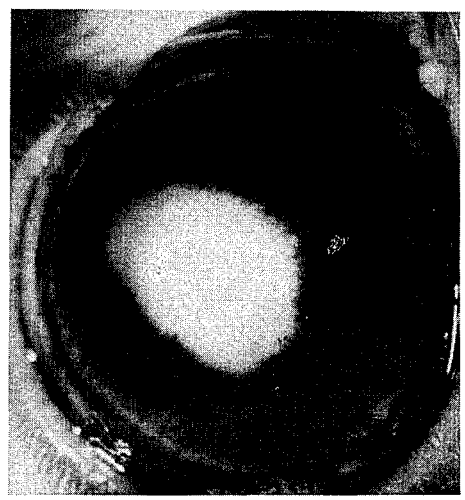
Figure 5:
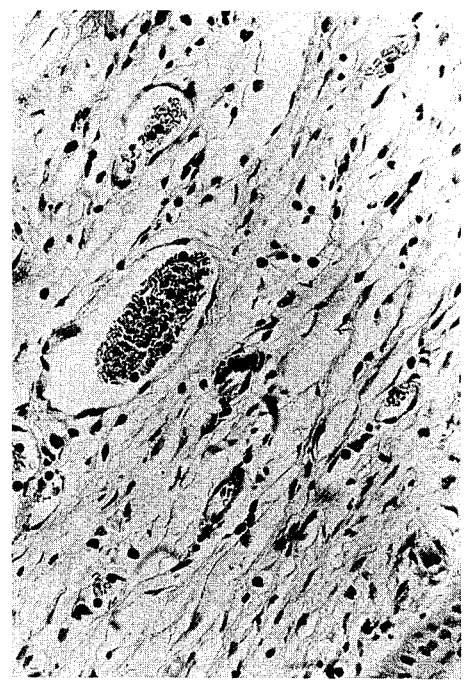
Figure 6:
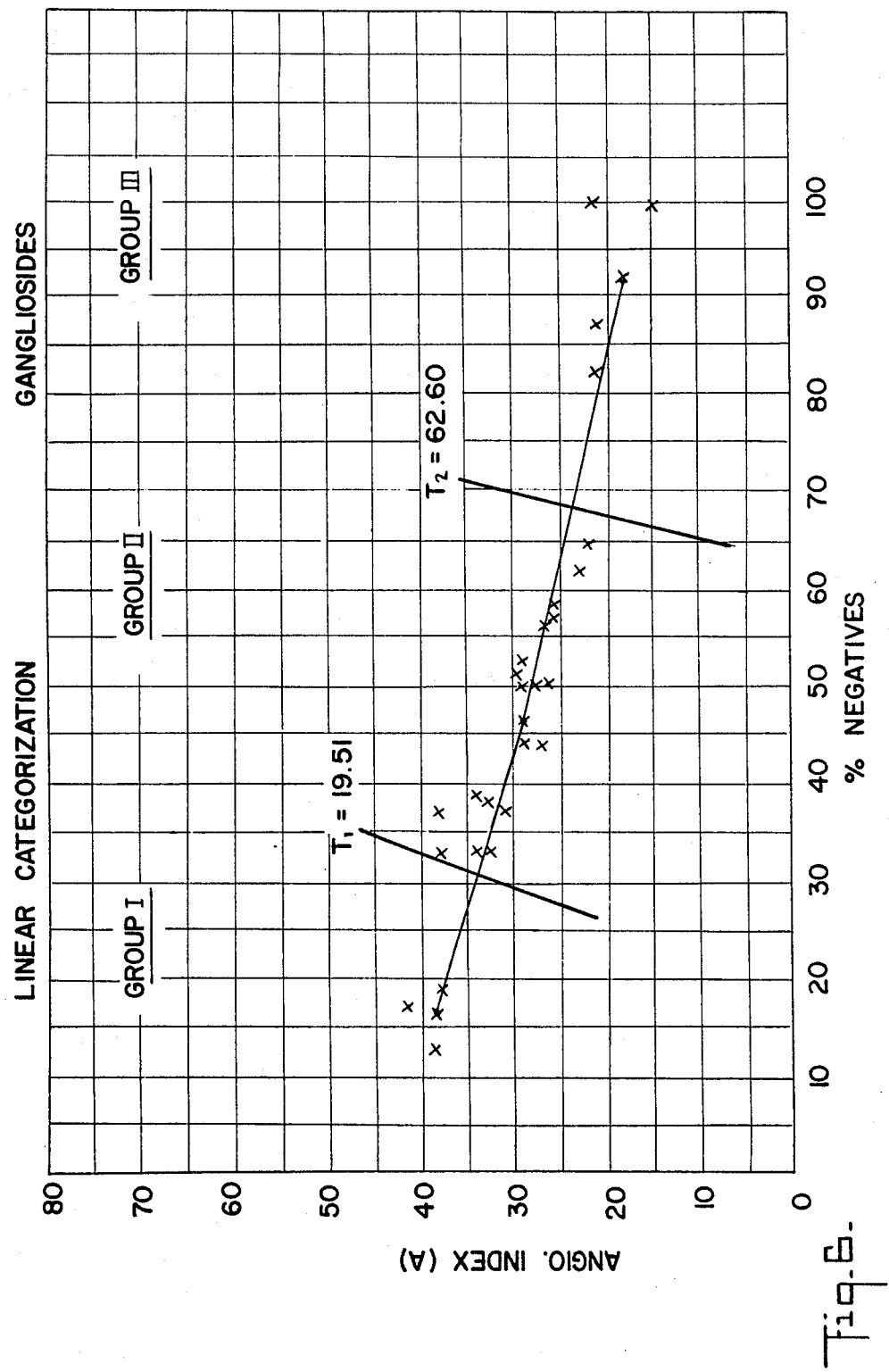
Figure 7:
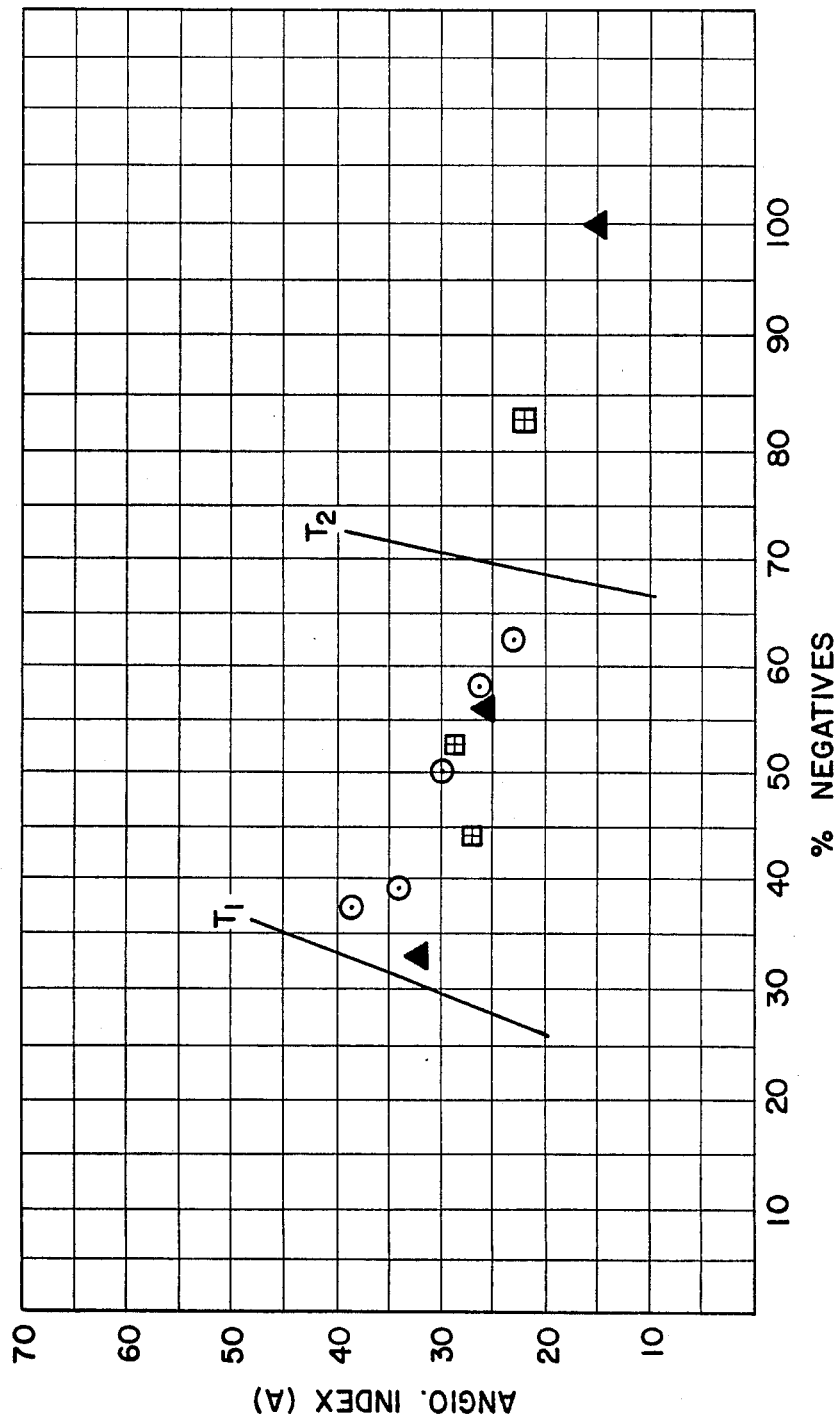
Figure 8:
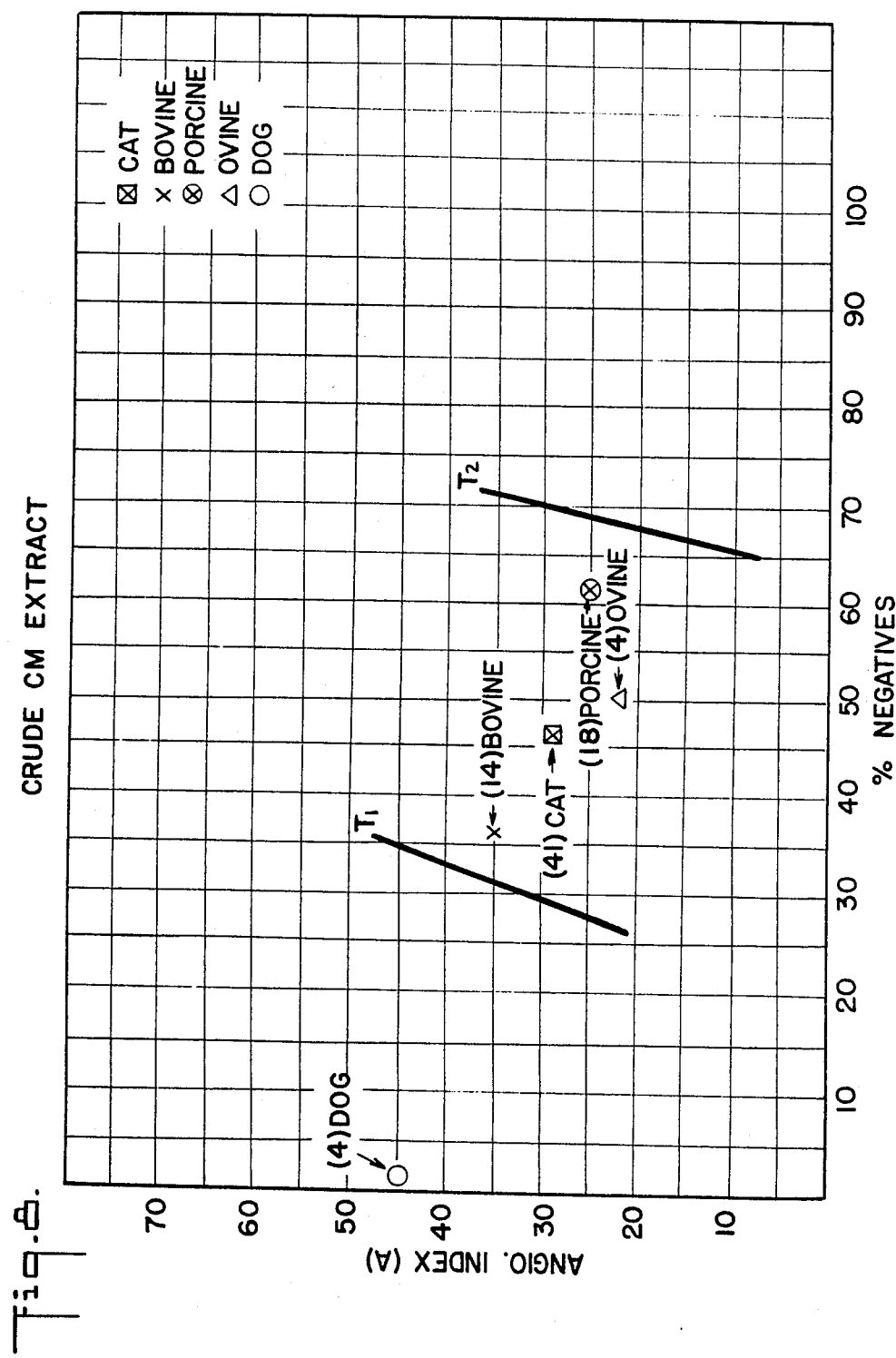
Figure 9:
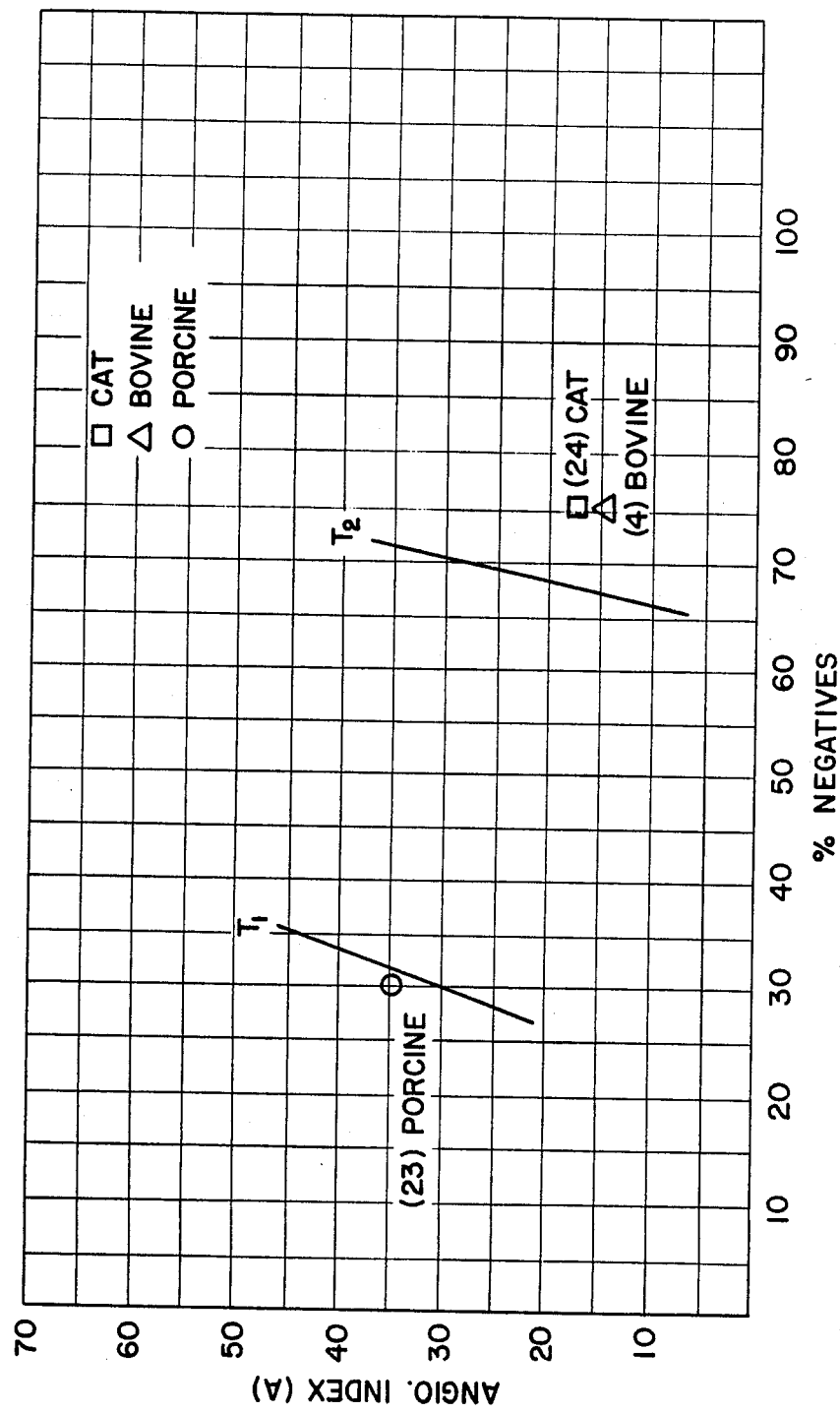
Figure 10:
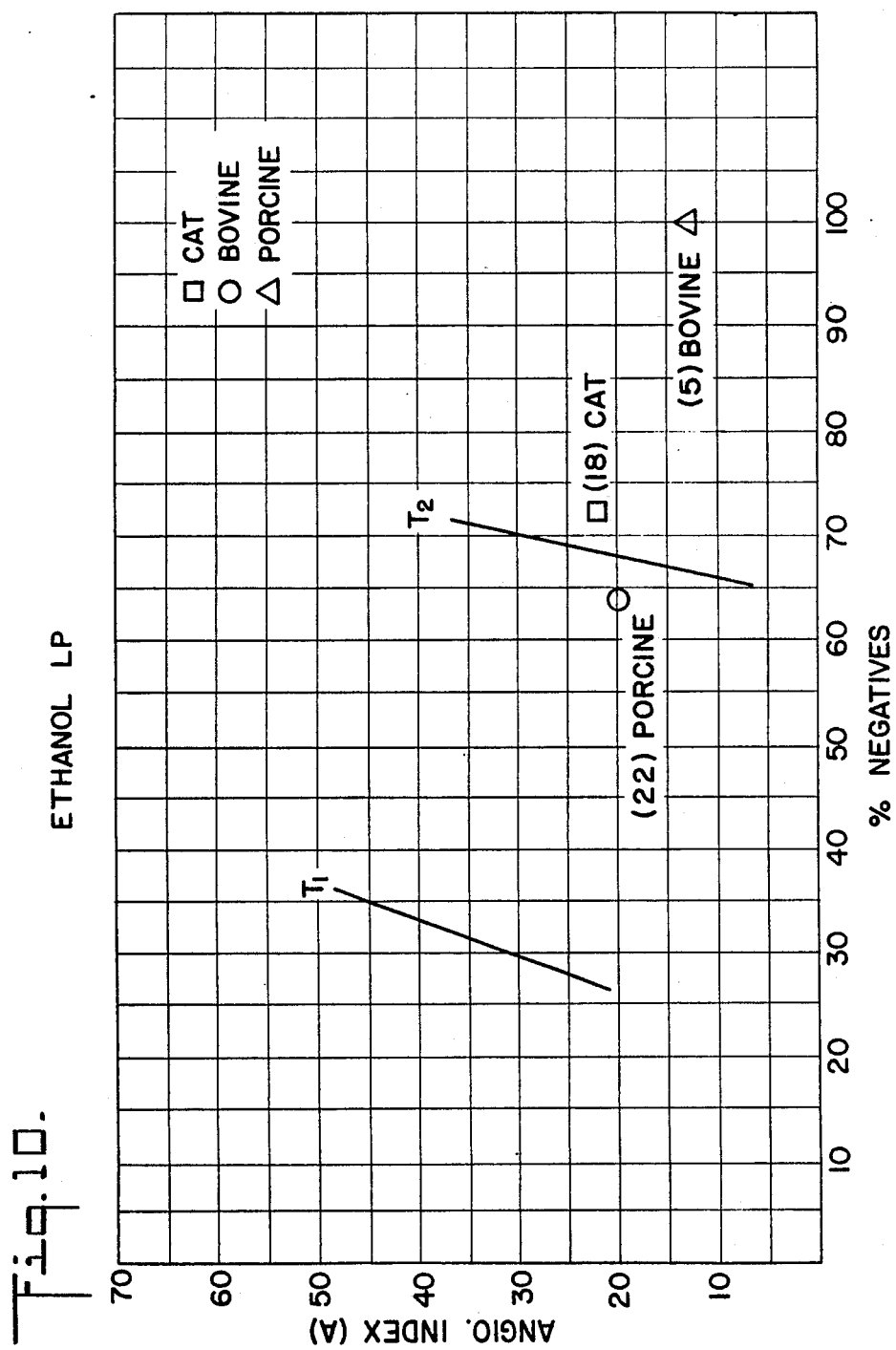
Figure 11:
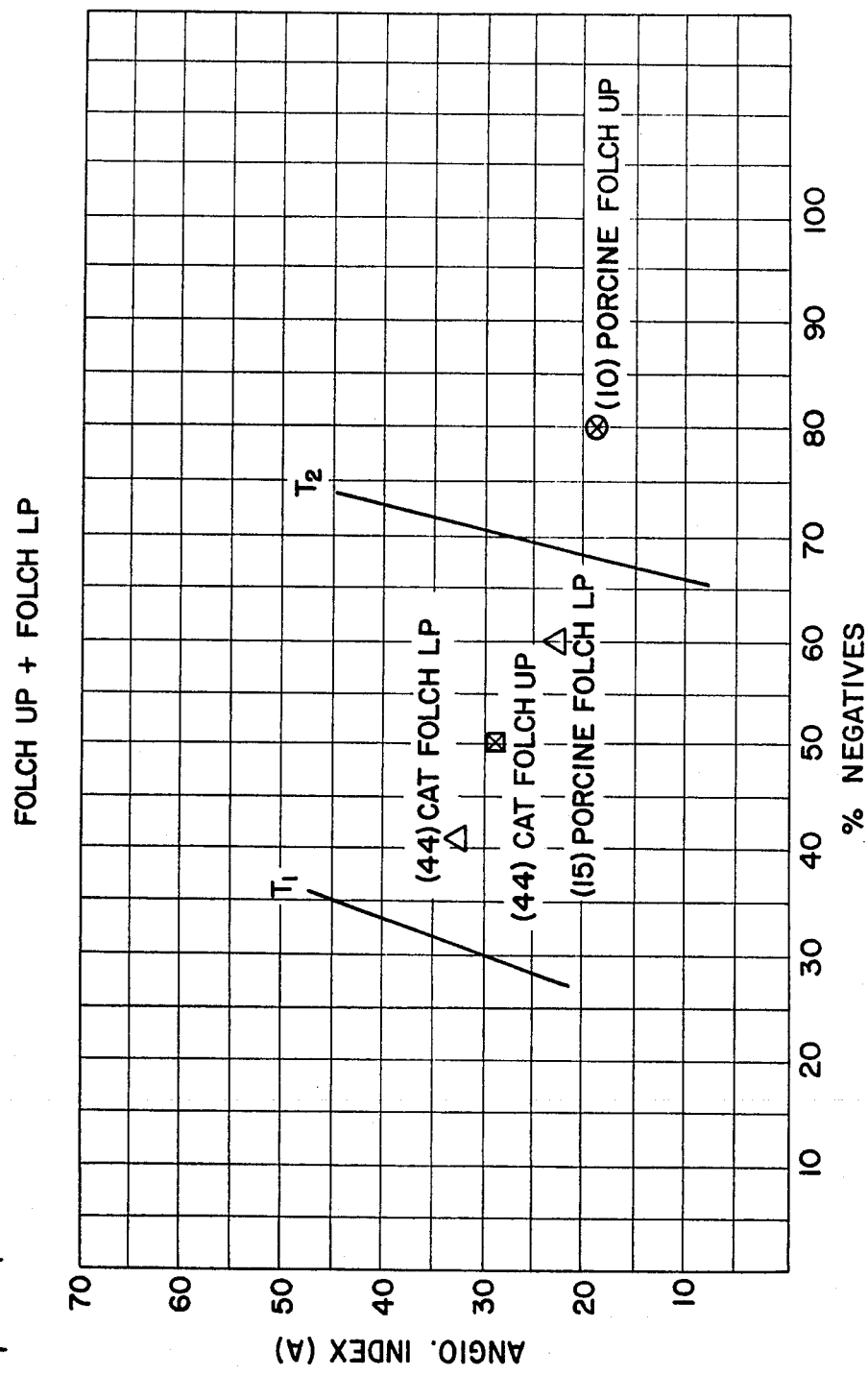
Figure 12:
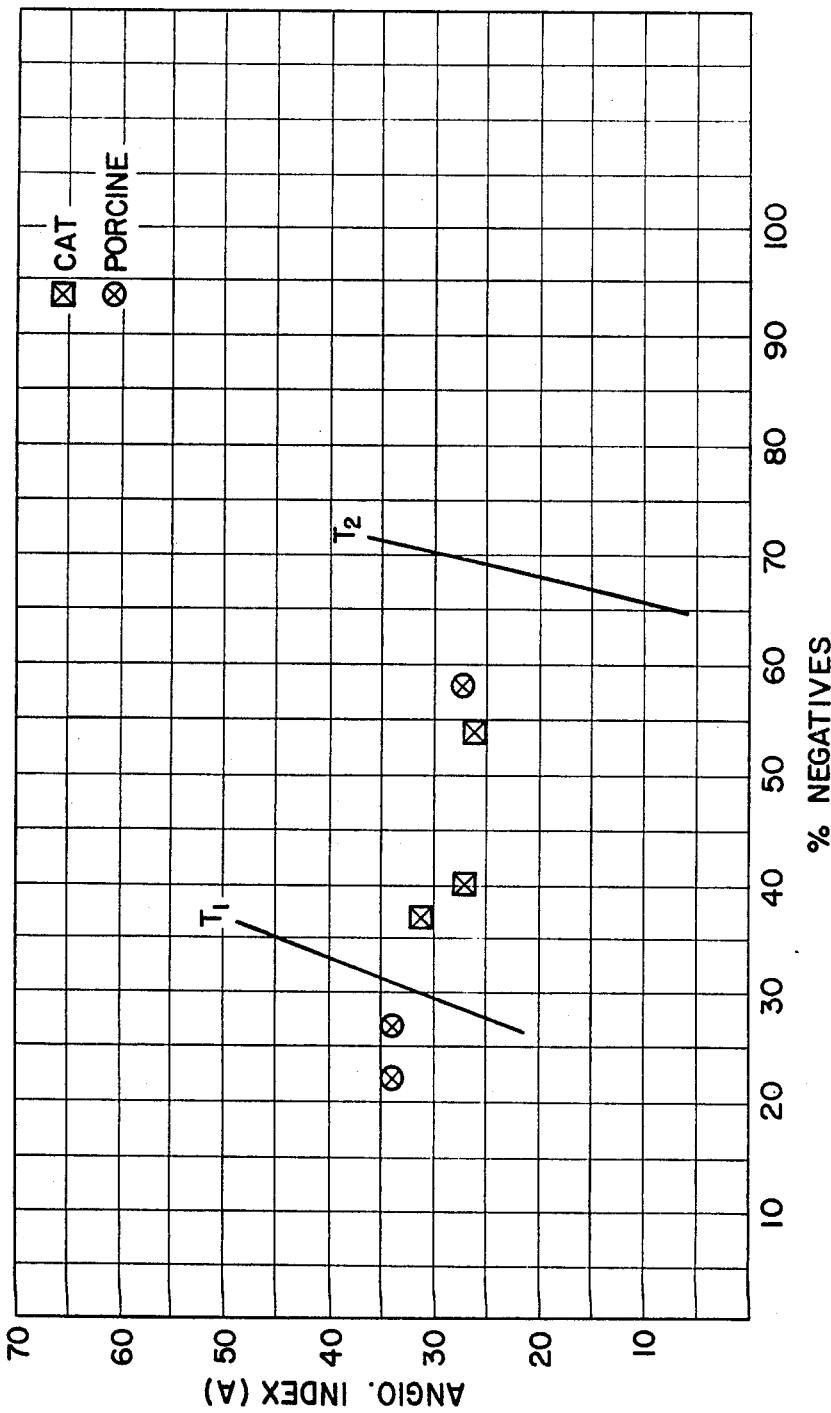
Figure 13:
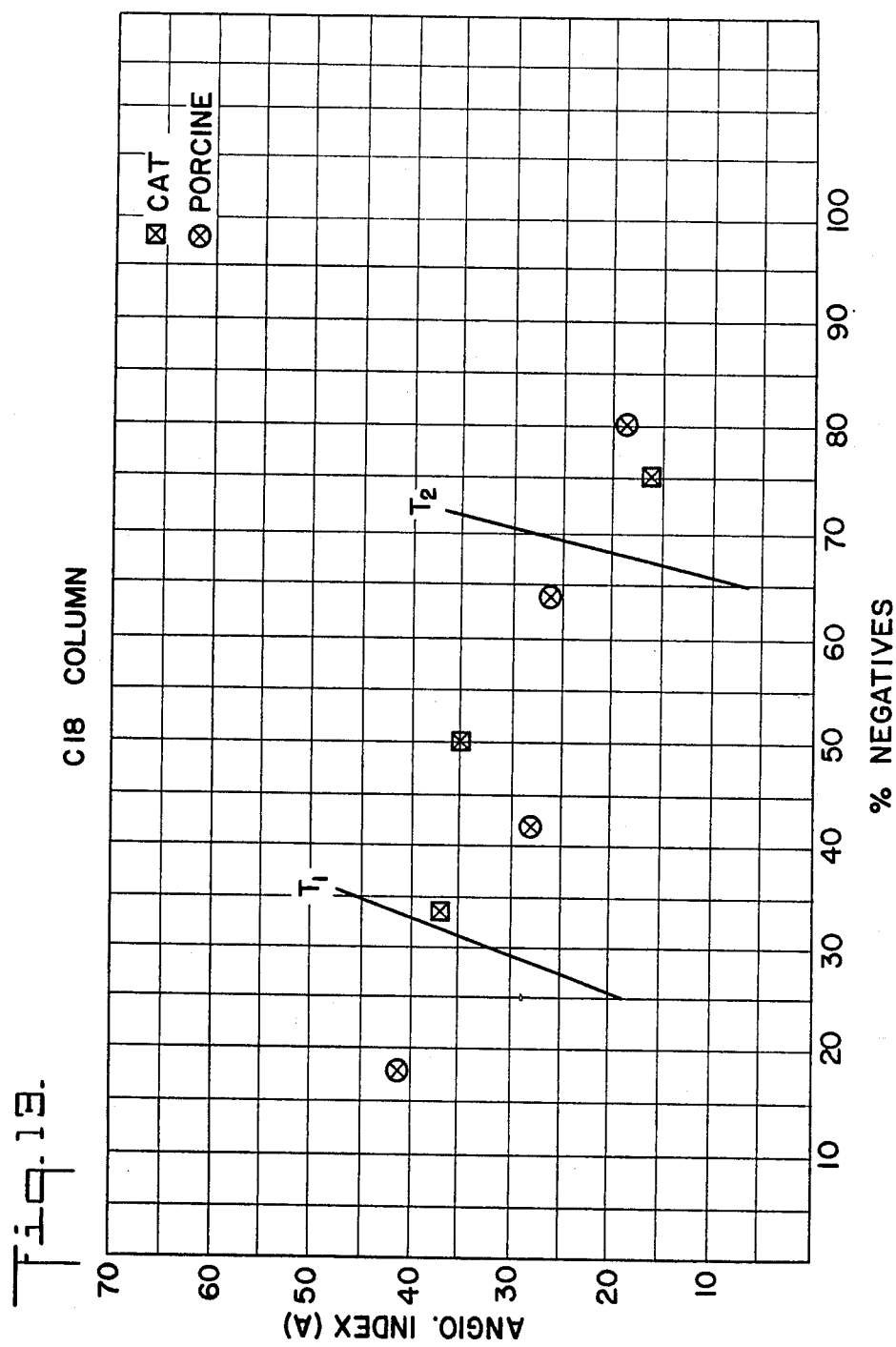
Figure 14:
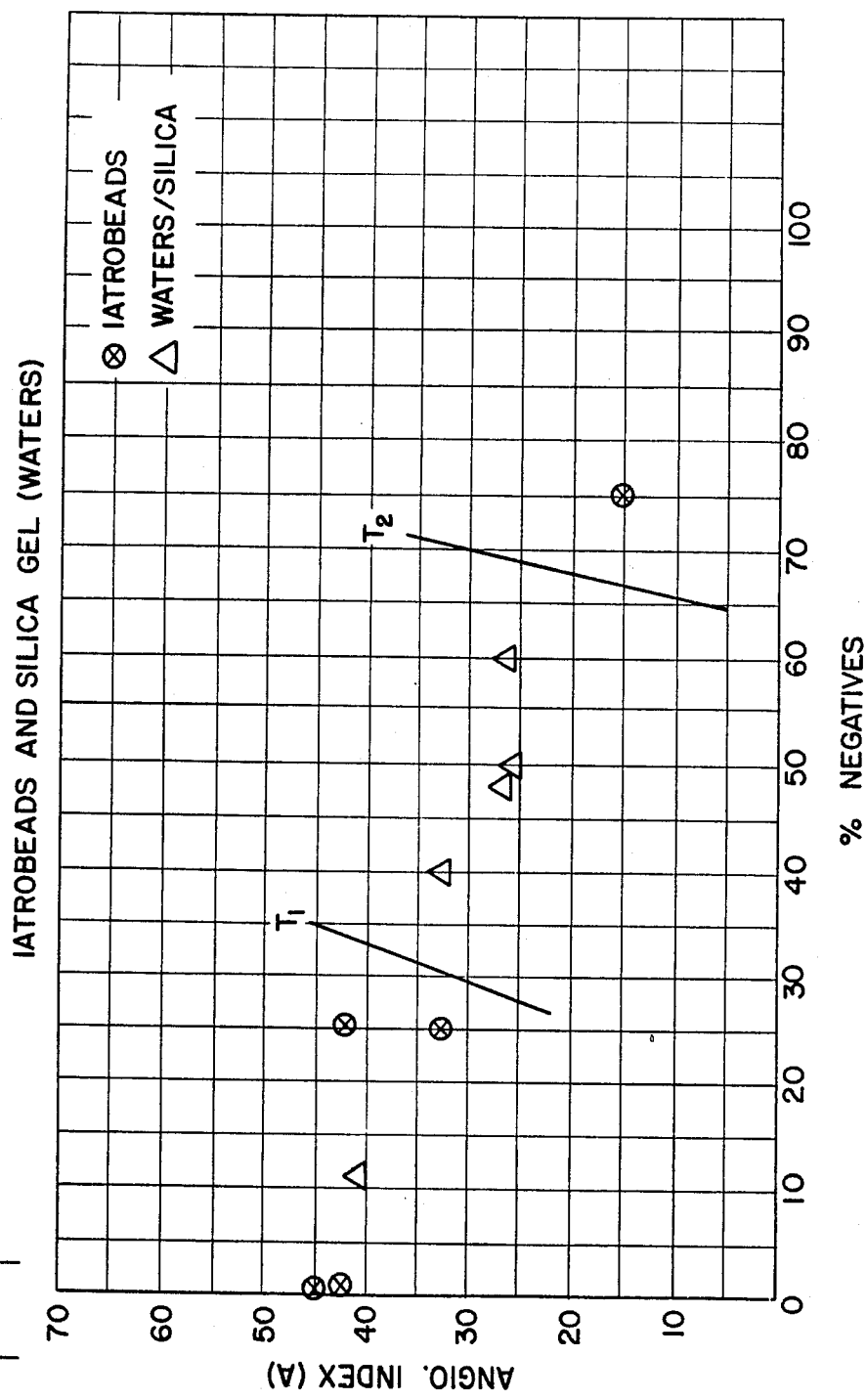
Figure 15:
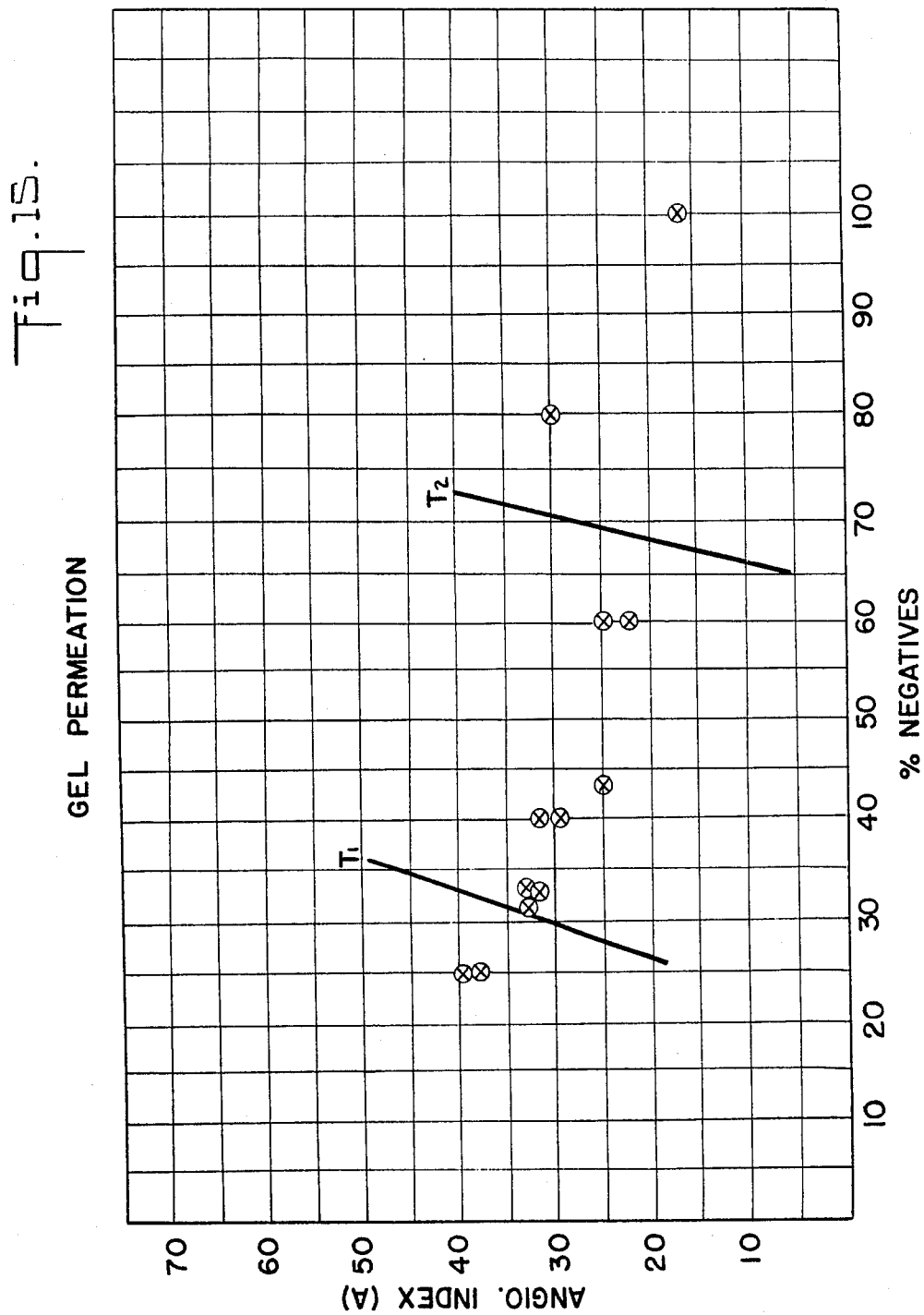

The course of the angiogenic response in the cornea to the injected aqueous suspended chloroform/methanol lipid preparation followed a consistent pattern of rapid development and intense activity. Following injection of the extracted lipid fraction, a mild corneal inflammatory reaction was observed within twenty-four hours which subsided within forty-eight hours. This initial inflammation is characterized by slight clouding of the cornea with minimal erythema in the scleral area which was often accompanied with a slight discharge from the eye. A pannus, the appearance of a curtain of blood vessels around the margin of the cornea, with interstitial blood vessel formation became grossly evident 3 to 4 days following the injection. By the seventh to tenth day, the blood vessels had formed a dense and richly structured network within the cornea. This is illustrated by the photograph in FIG. 3. Histological examination of the enucleated eyes harvested on the tenth day showed multiple capillaries within the corneal stroma; a photograph of the histological section illustrating such multiple capillaries within the stroma is shown in FIG. 4.

It is of particular note that the solvent extracted lipid fraction in aqueous medium initiates and sustains angiogenesis after only a single 50 microliter dose injection. Although the mechanism of this angiogenic process and response is presently unknown, it is apparent that the injection of the extracted lipid fraction from the omentum initiates and develops new blood vessel formation which becomes organized into dense, well structured, vascular networks in seven to ten days.

As shown in FIG. 3 further fractionation of the CMFr was performed by silica gel chromatography. Subsequent testing of each of the five lipid subfractions, with the cornea assay showed angiogenic activity to be present only in subfraction V with a noticeable angiogenic effect from any of the subfractions I-IV. The overall activity of subfraction V however, was measurably less than the chloroform/methanol lipid extraction preparation originally obtained. It was subsequently found that subfactors I-IV, although having no angiogenic activity in and of themselves, when combined with subfraction V act to enhance and increase the activity and potency of the angiogenic composition as a whole.

The experiments set forth supra show that the CMFr exhibits angiogenic activity. Further experiments were then performed, using additional fractions prepared following the outline of FIG. I. The experiments consisted of performing CAM assays, described infra. This leads to the derivation of the "Angiogenic Index", which is a measure of the effect the fractions had in the CAM assays. An additional value, the "Discrimination Unit", is also derived. Both of these are explained infra.

The experiments described were not confined to the omental fractions obtained by the experiments described supra. Once the general molecular composition of the more effective fractions was determined to contain lipid-containing molecules, especially gangliosides, additional lipid-containing molecules which are known to the art, were used. It was unexpectedly found that many of these materials also possessed strong, unexpected angiogenic activity. Additionally, experiments were performed using commercially available gangliosides, in new combinations. Again, unexpected angiogenic properties were found. Of even greater interest is the fact that compositions with mixtures of different gangliosides had greater than additive angiogenic effect.

VI. CAM Assays

Angiogenic properties of extracts, fractionates, and compositions were determined by subjecting these to Chick Embryo Chorioallantoic Membrane Assays ("CAM assays").

The CAM assay uses fertilized chicken eggs, and involves the following steps:

Preparing the Eggs: By using a power drill, a 2 cm square of shell is removed from the fertilized egg on day 4 of incubation. The opening is now referred to as a "window". Cellophane tape tightly seals off the window to the outside environment. The eggs are then put in the 37° C. incubator for another 4 days.

Making the Discs: On the 8th day after incubation, 0.4 g of agarose and 10 ml of PBS are mixed and heated to 100° C. in a small glass vial and subsequently mixed at 50° C. with a 2% BSA solution (in PBS). The mixture (2% agarose plus 1% BSA in PBS) is kept warm in a water bath. Using a pipet 20 to 40 ml of the testing solution (i.e., extract, fractionate, or composition) is mixed with a drop of the agarose mixture by constant stirring. After the large disc is hardened by gelation, it is subdivided into 4 smaller discs.

Placing the Discs on the Membrane: On the 8th day after incubation, the discs are placed inside the eggs on the CAM; choosing areas on the CAM with various degrees of blood vessel development. The selected area is approximately 1 cm away from the chick embryo but not so far away that the disc will lie beyond the CAM or stick to the inside shell wall. The eggs are then incubated for another 4 days. All instruments used are previously soaked in 98% ethanol.

Plastic Discs: Plastic discs were prepared using a hole puncher. After placing 2.5 ml of the test solution on each disc, the solution is allowed to dry over a warm plate. Additional 2.5 ml aliquots of the test solution may be added to the disc and dried between applications. After the disc is prepared, it is placed on the CAM as described supra.

Rating the Effects: Upon the 12th day of incubation, the discs are located inside the eggs and the windows are made larger by breaking off bits of the shell with a pair of forceps.

The eggs are then examined under the light microscope. The vascularization in the rest of the egg is compared to that surrounding the disc. Degrees of neovascularization in the direction of the disc is determined and compared with the effects of the discs in other eggs. The effects of each disc is rated on a scale of 1 to 5, as follows:

1 = one or two small areas of increased branching around the disc; essentially negative.

2 = three or more small areas of increased branching around the disc; a weak response.

3 = formation of "wheel spoke effect," which is self explanatory; increased branching around the disc; a moderate response.

4 = "wheel spoke effect" with increased branching around the disc, to a degree greater than in "3"; a strong response.

5 = "wheel spoke effect" with extensive branching around the disc; a very strong response.

Plus and minuses are also used, with each numerical value, so a CAM assay could have a value ranging from 1-(no response whatsoever) to 5 (exceptionally strong response, with extensive branching).

Based upon the foregoing scoring system, the ANGIOGENIC INDEX ("A" Index or "A" in the following tables) is determined. The A Index allows for comparative analysis of samples, in terms of angiogenic activity.

The Angiogenic Index is defined as:

$$100 \times \frac{\text{Total of scores on individual assays}}{\text{Maximum score possible}}$$

For example, in a sample containing 12 CAM assays, if 7 are "weak," 1 is "moderate," none are "strong," and 4 are "negative" the A Index would be calculated as follows:

$$A = \frac{7(2) + 1(3)}{12 \times 5} \times 100 = 28.33$$

Table III sets forth data obtained by analyzing extracts, and solvent partition components obtained using the procedures set forth in FIGS. I, II and III. The terminology used is the same as that used in the Figures.

The samples were obtained from feline, bovine, porcine, and canine omenta, as indicated.

TABLE III

| COMPOUND | EGGS | A | % NEG | W | M | S |
|---|---|---|---|---|---|---|
| EXTRACTION | | | | | | |
| Cat CMFr | 41 | 28.98 | 46.34 | 17 | 4 | 1 |
| Bovine CMFr | 14 | 35.27 | 35.71 | 5 | 4 | 0 |
| Porcine CMFr | 18 | 24.9 | 61 | 7 | 0 | 0 |
| Ovine CMFr | 4 | 23.35 | 50.00 | 2 | 0 | 0 |
| Canine CMFr | 4 | 45.05 | 0 | 3 | 1 | 0 |
| CatPBS supernatant | 15 | 19.12 | 73.33 | 4 | 0 | 0 |
| 1% HAc sol, UP | 18 | 28.17 | 44.44 | 6 | 4 | 0 |
| 1% HAc insol, LP | 10 | 8.72 | 70.00 | 1 | 2 | 0 |
| Cat subcut. fat | 6 | 20.03 | 83.33 | 0 | 1 | 0 |
| Porcine subcut. fat | 8 | 33.43 | 37.50 | 5 | 0 | 0 |
| Cat lipid cake | 5 | 13.36 | 100 | 0 | 0 | 0 |
| CMFr supernatant (cat) | 16 | 34.7 | 38 | 9 | 1 | 0 |
| CMFr pellet (cat) | 19 | 39.0 | 32 | 9 | 4 | 0 |
| CMFr supernatant (porcine) | 7 | 32.4 | 43 | 4 | 0 | 0 |
| CMFr pellet (porcine) | 8 | 40.1 | 25 | 5 | 1 | 0 |
| SOLVENT PARTITION | | | | | | |
| Cat-Hexane UP | 24 | 16.7 | 75 | 6 | 0 | 0 |
| Bovine-Hexane UP | 4 | 15.05 | 75 | 3 | 1 | 0 |
| Porcine-Hexane UP | 23 | 35.4 | 30 | 16 | 0 | 0 |
| Cat-Ethanol LP | 18 | 21.9 | 72 | 5 | 0 | 0 |
| Bovine-Ethanol LP | 5 | 13.36 | 100 | 0 | 0 | 0 |
| Porcine Ethanol LP | 22 | 19.4 | 64 | 7 | 1 | 0 |
| Cat-Folch UP | 44 | 28.8 | 50 | 13 | 9 | 0 |
| Porcine-Folch UP | 10 | 18.7 | 80 | 1 | 1 | 0 |
| Ovine-Folch UP | 4 | 18.40 | 100 | 0 | 0 | 0 |
| Dog-Folch UP | 4 | 23.40 | 100 | 0 | 0 | 0 |
| Cat Folch LP | 44 | 33.2 | 41 | 16 | 8 | 2 |
| Porcine Folch LP | 15 | 22.7 | 60 | 6 | 0 | 0 |
| Ovine Folch LP | 4 | 10.00 | 100 | 0 | 0 | 0 |
| Dog Folch LP | 4 | 38.40 | 25 | 3 | 0 | 0 |
| C18 COLUMN ELUATES | | | | | | |
| Cat, C18 Lipid | 4 | 35.05 | 50 | 1 | 1 | 1 |
| Porcine, C18 Lipid | 14 | 25.8 | 64 | 5 | 0 | 0 |
| Cat C18 nonlipid | 8 | 15.88 | 75 | 1 | 1 | 0 |
| Porcine, Lipid UP, base trt | 5 | 18.72 | 80 | 1 | 0 | 0 |
| Cat, Lipid UP base trt | 10 | 38.70 | 20 | 8 | 0 | 0 |
| Cat, C18 nonlipid MeOH sol 11 | 11 | 46.70 | 18 | 9 | 0 | 0 |
| Porcine, C18 nonlipid MeOH 11 | 11 | 40.7 | 18 | 9 | 0 | 0 |
| Porcine, C18 nonlipid H2O | 12 | 27.8 | 42 | 7 | 0 | 0 |
| Cat, C18 nonlipid (sol.) | 10 | 40.1 | 10 | 8 | 1 | 0 |
| DEAE COLUMN | | | | | | |
| Cat, Total Gangs. | 12 | 27.8 | 50 | 3 | 3 | 0 |
| Cat monosialgang. | 18 | 34.1 | 39 | 10 | 1 | 0 |
| Porcine, Monosialogang. | 29 | 23.2 | 62 | 11 | 2 | 2 |
| Cat, disialogang. | 15 | 15.1 | 100 | 0 | 0 | 0 |
| Porcine, disialogang. | 28 | 25.8 | 57 | 10 | 2 | 0 |
| Cat, trisialogang. | 17 | 21.6 | 82 | 3 | 0 | 0 |
| Porcine, trisialogang. | 35 | 30.2 | 49 | 12 | 0 | 0 |
| Cat, Neutral gang. Forssman | 49 | 29.0 | 49 | 25 | 0 | 0 |
| Porcine, Neutral Gang. | 14 | 33.4 | 50 | 0 | 0 | 0 |
| Cat, Non-lipid, DEAE neutral | 15 | 23.6 | 67 | 5 | 0 | 0 |
| Cat, Non-lipid, neutral, H2O sol. | 14 | 24.3 | 57 | 6 | 0 | 0 |
| Cat. Nonlipid, neut. MeOH sol. | 14 | 33.8 | 36 | 8 | 1 | 0 |
| Cat, Mono, di,tri-sial gang. | 23 | 38.9 | 13 | 19 | 1 | 0 |
| Porcine, Mono, di, tri-sialo | 26 | 21.8 | 65 | 9 | 0 | 0 |
| Cat, mono, di-sialogang | 9 | 34.1 | 33 | 6 | 0 | 0 |
| Porcine,mono, disialogang. | 18 | 28.6 | 44 | 10 | 0 | 0 |
| Cat, mono, trisialogang. | 16 | 37.6 | 19 | 13 | 0 | 0 |
| Porcine, mono, trisialogang. | 26 | 27.0 | 50 | 13 | 0 | 0 |
| Cat, di, trisialogang. | 8 | 30.9 | 37 | 3 | 2 | 0 |
| Porcine, di,trisialogang. | 27 | 27.0 | 56 | 12 | 0 | 0 |
| Cat, monosialogangl. | 16 | 20.9 | 87 | 2 | 0 | 0 |

TABLE III-continued

| | EGGS | A | % NEG | W | M | S |
|---|---|---|---|---|---|---|
| Forssman | | | | | | |
| UNISIL COLUMN | | | | | | |
| CAT, LP, CHCL$_3$ | 22 | 30.0 | 36 | 13 | 1 | 0 |
| Porcine LP, CHCl$_3$ | 9 | 34.1 | 22 | 7 | 0 | 0 |
| CAT, LP, Acetone:MeOH | 39 | 35.1 | 23 | 29 | 1 | 0 |
| Porcine LP, Acetone:MeOH | 12 | 26.7 | 58 | 5 | 0 | 0 |
| Cat, LP, Methanol | 26 | 33.1 | 23 | 20 | 0 | 0 |
| Porcine, LP, Methanol | 11 | 34.0 | 27 | 8 | 0 | 0 |
| IATROBEADS (CHROMATOGRAPHY) | | | | | | |
| FRACTION NO | | | | | | |
| I | 4 | 45 | 0 | 3 | 1 | 0 |
| II | 4 | 15 | 75 | 1 | 0 | 0 |
| III | 4 | 41.75 | 25 | 2 | 1 | 0 |
| IV | 4 | 43.4 | 0 | 4 | 0 | 0 |
| V | 4 | 33.35 | 25 | 2 | 1 | 0 |
| GEL PERMEATION | | | | | | |
| I | 5 | 32.08 | 40 | 4 | 0 | 0 |
| II | 7 | 24.77 | 43 | 3 | 1 | 0 |
| III | 6 | 33.40 | 33 | 2 | 2 | 0 |
| IV | 4 | 29.44 | 80 | 1 | 0 | 0 |
| V | 5 | 25.36 | 60 | 2 | 0 | 0 |
| VI | 5 | 29.40 | 40 | 3 | 0 | 0 |
| VII | 5 | 22.72 | 60 | 2 | 0 | 0 |
| VIII | 6 | 32.27 | 33 | 3 | 1 | 0 |
| IX | 3 | 17.87 | 100 | 0 | 0 | 0 |
| X | 3 | 33.40 | 33 | 1 | 1 | 0 |
| XI | 4 | 40.05 | 25 | 1 | 2 | 0 |
| AFFINITY CHROMATOGRAPHY | | | | | | |
| Heparin-binding from Folch UP (cat) | 14 | 29.1 | 50 | 6 | 1 | 0 |
| Heparin-binding from PBS homogenate (FIG. 1) (cat) | 4 | 46.8 | 0 | 3 | 1 | 0 |
| Gelatin-binding from Folch UP (cat) | 4 | 31.7 | 50 | 1 | 1 | 0 |

Table IV, which follows, contains data similar to that in Tables I–III. The samples, however, are all ganglioside materials. The first group is ganglioside obtained from cat omental extracts. The ganglioside were separated into mono, di and tri-sialyated components, and were also mixed, in 1:1, or 1:1:1 ratios. Similar analyses were performed with porcine omenta-derived glycosides.

The "Supelco" group presents analysis for known, commercially available gangliosides, (entries 1–4 of this group). Entries 5–8, however, represent new compositions of gangliosides.

This table also presents a value for the materials, the "DU" or Discriminator Value."

In order to determine the "DU" value, the A Index value is taken as well as the percent negative Means values $s_I$ and $S_I$ the compounds of a class I, and $s_{II}$ and $S_{II}$ values of a class II. These numbers, $s_I$, $S_I$, $s_{II}$ and $S_{II}$ determine centroids of distribution of each class of compounds. Using this, values $W_1$ and $w_2$ and $X_{1T}$, $X_{2T}$, "weight coefficients" are determined via $$w_1 = s_{II} - s_I \quad X_{1T} = (S_{S11} + S_I)/2$$
$$w_2 = S_{II} - S_I \quad X_{2T} = (S_{11} = S_1)/2$$

$$DU = S\frac{w_1}{(w_1^2 + W_2^2)^{\frac{1}{2}}} + S\frac{w_2}{(w_1^2 + w_2^2)^{\frac{1}{2}}}$$

and $$T = X_{1T}\frac{w_1}{(w_1^2 + w_2^2)^{\frac{1}{2}}} + X_{2T}\frac{w_2}{(w_1^2 + w_2^2)^{\frac{1}{2}}}$$

The smaller the DU value, the greater the angiogenic properties of the sample. A ranking of DU values by compound, from best to worst is presented in Table V.

TABLE IV

| Compound | Major Component(s) | Eggs | DU | A | % Neg | W | M | S |
|---|---|---|---|---|---|---|---|---|
| Cat Omentum | | | | | | | | |
| Acidic DEAE gangl | | 12 | 39.17 | 27.8 | 50% | 3 | 3 | 0 |
| Monosialogangl. | GM3 | 13 | 26.77 | 34.1 | 39% | 10 | 1 | 0 |
| Disialogangl. | GD3 | 15 | 94.59 | 15.1 | 100% | 0 | 0 | 0 |
| Trisialogangl | | 17 | 75.63 | 21.6 | 82% | 3 | 0 | 0 |
| Mono, Di, Tri, (Mix) | | 23 | 0.54 | 38.9 | 13% | 19 | 1 | 0 |
| Mono, Di (Mix) | | 9 | 21.06 | 34.1 | 33% | 6 | 0 | 0 |
| Mono, Tri (Mix) | | 16 | 6.66 | 37.5 | 14% | 13 | 0 | 0 |
| Di, Tri (Mix) | | 8 | 25.84 | 30.9 | 37% | 3 | 2 | 0 |
| Neutral gangl Forssman | | 49 | 37.85 | 29.0 | 49% | 25 | 0 | 0 |
| Mono, Forssman (Mix) | | 16 | 80.67 | 20.9 | 87% | 2 | 0 | 0 |
| Brain GM1 | GM1 | 8 | 23.56 | 38.4 | 37% | 2 | 3 | 0 |
| Brain GM3 | GM3 | 14 | 38.77 | 29.1 | 50% | 6 | 1 | 0 |
| Supelco (Brain) | | | | | | | | |
| Purified Mix Gangl. | | 12 | 21.45 | 32.8 | 33% | 7 | 1 | 0 |
| Monosialogangl. | GM1 | 12 | 47.28 | 26.2 | 58% | 5 | 0 | 0 |
| Disialogangl. | GD1a | 9 | 21.51 | 32.6 | 33% | 6 | 0 | 0 |
| Trisialogangl. | GT1b + GD1b | 18 | 33.67 | 27.1 | 44% | 10 | 0 | 0 |
| Mono/Di (Mix) | | 6 | 19.90 | 37.9 | 33% | 4 | 0 | 0 |
| Mono/Tri (Mix) | | 5 | 93.27 | 21.4 | 100% | 0 | 0 | 0 |
| Di/Tri (Mix) | | 6 | 4.36 | 38.9 | 17% | 5 | 0 | 0 |
| Mono/Di/Tri (Mix) | | 6 | 10.56 | 41.2 | 17% | 4 | 1 | 0 |
| Porcine Omentum | | | | | | | | |
| Monosialogangl | | 29 | 52.0 | 23.2 | 62% | 11 | 2 | 2 |
| Disialogangl | | 28 | 46.44 | 25.8 | 57% | 10 | 2 | 0 |
| Trisialogangl | | 25 | 40.74 | 28.9 | 52% | 12 | 0 | 0 |
| Mono, Di, Tri (Mix) | | 26 | 55.28 | 21.8 | 65% | 9 | 0 | 0 |
| Mono, Di (Mix) | | 18 | 33.21 | 28.6 | 44% | 10 | 0 | 0 |
| Mono, Tri (Mix) | | 26 | 34.41 | 27.0 | 50% | 13 | 0 | 0 |
| Di, Tri (Mix) | | 27 | 45.13 | 27.0 | 56% | 12 | 0 | 0 |

TABLE V

GANGLIOSIDES ANGIOGENIC POTENCY

| RANK | DU | COMPOUND |
|---|---|---|
| 1 | −10.56 | Supelco, Mono/Di/Tri Mixture |
| 2 | 0.54 | Cat Om., Mono/Di/Tri Mixture |
| 3 | 4.36 | Supelco, Di/Tri Mixture |
| 4 | 6.66 | Cat Om., Mono/Tri Mixture |
| 5 | 19.90 | Supelco, Mono/Di Mixture |
| 6 | 21.06 | Cat Om., Mono/Di Mixture |
| 7 | 21.45 | Supelco, Purified mixed gangliosides |
| 8 | 21.51 | Supelco, Disialo |
| 9 | 23.56 | GM1 |
| 10 | 25.84 | Cat Om., Di/Tri Mixture |
| 11 | 26.77 | Cat Om., Monosialo (GM3) |
| 12 | 33.21 | Porcino, Om. Mono/Di Mixture |
| 13 | 33.67 | Supelco Trisialo |
| 14 | 37.85 | Cat Om., Neutral Gangl. Forssman |
| 15 | 38.77 | GM3 |
| 16 | 39.17 | Cat Om., Acidic DEAF gangl |
| 17 | 40.74 | Porcine Om., trisialogangl |
| 18 | 45.13 | Porcine Om., Di/Tri mixture |
| 19 | 46.44 | Porcine Om, Disialogangl |
| 20 | 47.28 | Supelco monosialogangl. |
| 21 | 52.00 | Porcine Om., disialogangl |
| 22 | 55.28 | Porcine Om., Mono/Di/Tri mixture |
| 23 | 75.63 | Cat Om., Trisialogangl. |
| 24 | 80.67 | Cat Om./Mono/Forrsman Mixture |
| 25 | 93.27 | Supelco Mono/Tri Mixture |
| 26 | 94.59 | Cat Om., Disialogangl |

These results show that, while the CMFr does possess angiogenic activity vis a vis the CAM assay, the additional fractionates obtained following the process outlined in FIG. II, possess greater Angiogenic properties. For example, by reference to Table III, Cat CMFr (the first entry) has an A value of 28.98, but 46.34% of the tests were negative. The purer, monosialoganglio-sides obtained on DEAE column, in contrast, show an A value of 34.1, with only 39% negative. In contrast, non-lipid fractions, also from DEAE columns, show 23.6 and 67% negative—a drop, in spite of purification. Finally, for this comparison, a mix of mono, di, and tri sialogangliosides from Cat omentum shows values of 38.9 and only 13% negative.

Additional comparisons can be drawn from the data in Table III. The DU value, displayed in Tables IV and V, is a useful shorthand for showing actual effectiveness, as it takes into account not only the A value, but the percentage negative. The lower the DU value, the more effective the material tested. Hence, by referring to Table VII, it can be seen that the novel mixture of known gangliosides (Supelco mono-, di- and tri-sialogangliosides), and the fraction containing feline mono-, di-, and tri-sialogangliosides, are the most effective compositions.

Figure 16:
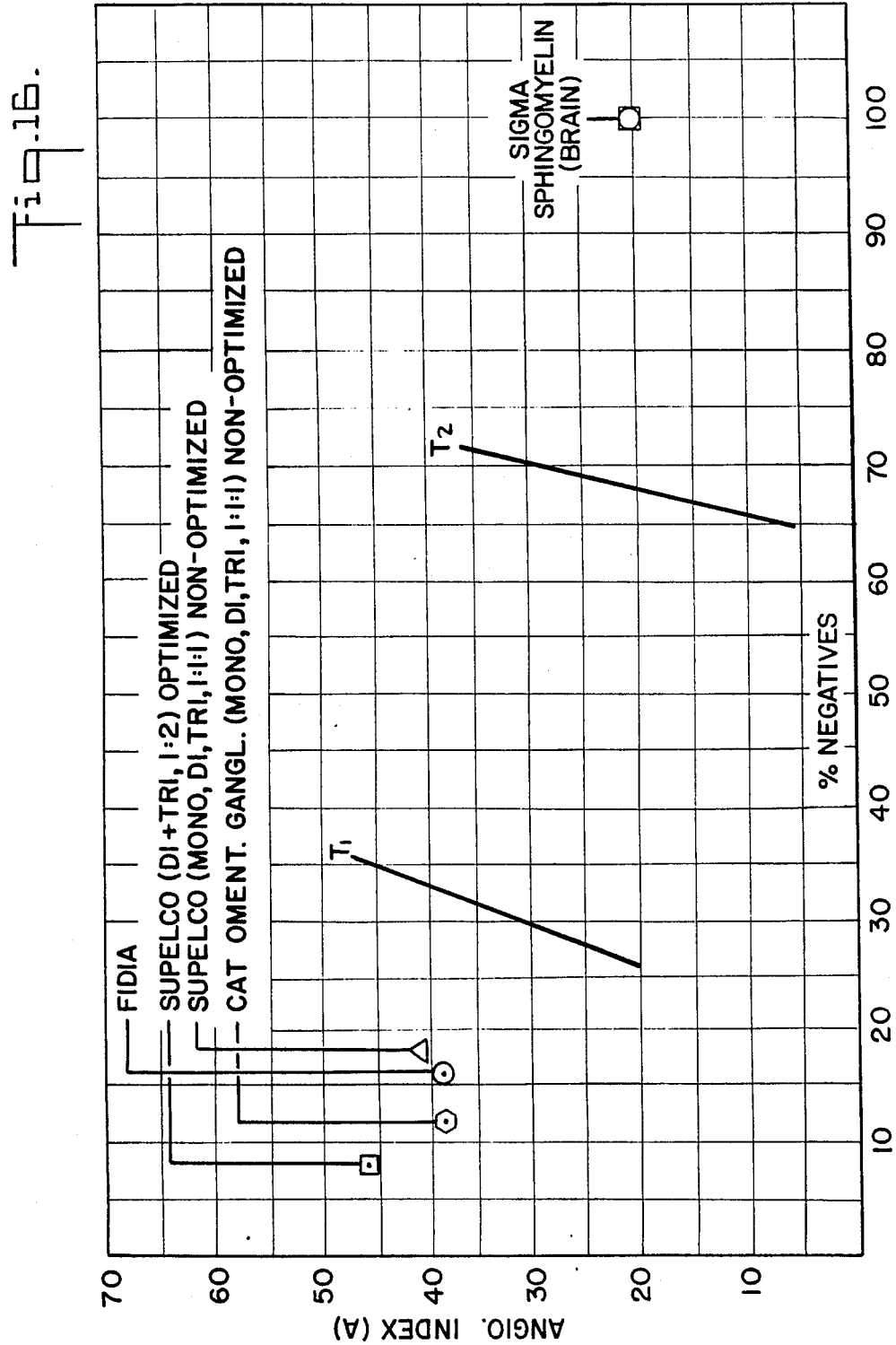

These results may also be shown graphically, as will be seen by referring to FIGS. 6-16. These Figures are linear categorization graphs) for various substances. In linear categorization, as applied herein, Angiogenic Index is platted against the percent negative. A "centroid" or "mean" point is obtained for each group of materials so platted, and the T value is obtained from a comparison of every two groups of compounds. This T value is then an index to which compositions are more effective than others. FIG. III establishes these guidelines for T values, using all samples tested. Subsequently, in FIGS. 7-16 different groups are plotted against the T values. Anything plotting to the left of $T_2$ shows promise as an angiogenic composition. FIG. 16 shows the best compositions.

Figure 17:
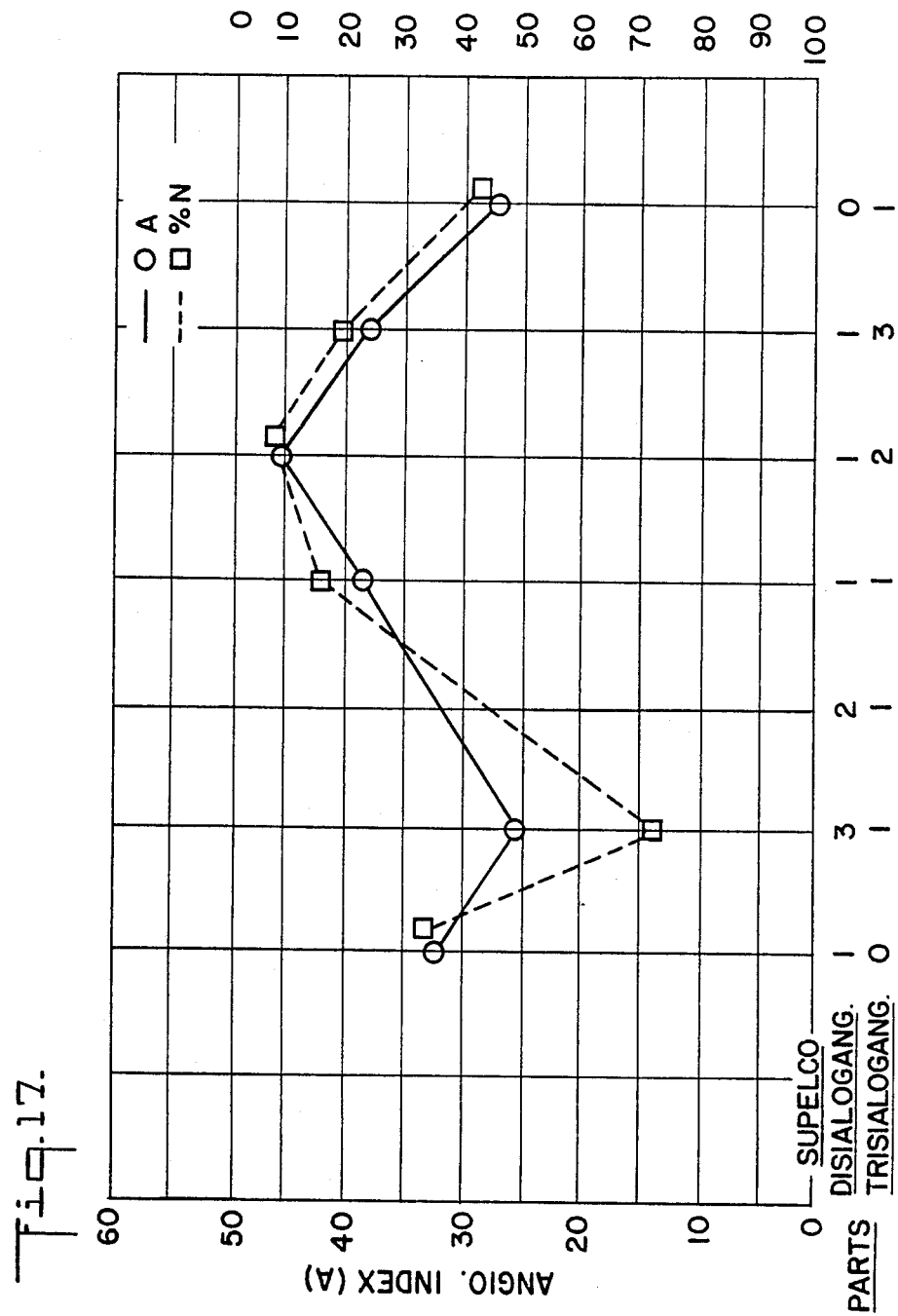

FIG. 17 is included to show a graph of the Angiogenic index plotted against an inverted negative percentage standard, using novel mixtures of known di- and trisialogangliosides. The graph demonstrates that the best mixture is di- and tri-sialogangliosides, in a 1:2 ratio. This graph is interesting because the curves obtained are strinkingly similar to those obtained, when antigen-antibody complexing is plotted. This suggests that a complexing reaction not unlike precipitant and agglutination type reactions characteristic of antigen-antibody systems is taking place.

The following experiments show that the CMFr, described supra, has in vivo efficacy in angiogenesis. The experiments are reported in Ser. No. 642,624, filed Aug. 20, 1984. As will be seen, by reference to Tables III–VII, the CMFr has a lower Angiogenic Index, and a higher Discrimination Unit value than do the additional fractions and mixtures tested in similar fashion (i.e., the CAM assay). One skilled in the art will see, therefore, that it would be expected that these experiments may be repeated with the additional fractions, with expected superior results.

Other commercially available lipid compounds purchased primarily from the Supelco and Sigma Chemical companies, or supplied by individual investigators were tested for the ability to induce angiogenesis in the CAM. These results are presented in Table VI.

TABLE VI

| COMPOUND | EGGS | A | % NEG | W | M | S |
|---|---|---|---|---|---|---|
| GLYCOLIPIDS AND GANGLIOSIDES | | | | | | |
| Cerebrosides (Supelco) | 16 | 36.3 | 38 | 9 | 1 | 0 |
| Gangliosides (Fidia Cronassial 20) | 18 | 38.6 | 17 | 14 | 1 | 0 |
| Gangliosides (Supelco) | 15 | 34.3 | 33 | 8 | 2 | 0 |
| Globoside (Supelco) | 17 | 34.6 | 29 | 10 | 2 | 0 |
| Steryl glucoside (Supelco) | 16 | 43.0 | 19 | 11 | 2 | 0 |
| Ceramides (Supelco) | 17 | 32.2 | 41 | 8 | 2 | 0 |
| Digalactosyl-diglyceride (Supelco) | 14 | 37.2 | 29 | 10 | 0 | 0 |
| Monogalactosyl diglyceride (Supelco) | 4 | 27.6 | 43 | 4 | 0 | 0 |
| Ceramide galactoside (Supelco) | 20 | 27.0 | 60 | 7 | 1 | 0 |
| Purified mixed gangliosides (Supelco) | 19 | 28.8 | 42 | 10 | 1 | 0 |
| Ceramides, Type III (Sigma) | 18 | 31.9 | 44 | 10 | 0 | 0 |
| Cerebrosides, Type I (Sigma) | 19 | 30.2 | 53 | 8 | 1 | 0 |
| Ceramides, Type IV (Sigma) | 16 | 30.5 | 37 | 10 | 0 | 0 |
| Cerabrosides, Type II (Sigma) | 13 | 30.3 | 38 | 8 | 0 | 0 |
| Sulfatides (Sigma) | 7 | 28.7 | 57 | 3 | 0 | 0 |
| Sulfatides (Supelco) | 6 | 30.0 | 50 | 3 | 0 | 0 |
| Glucocerebrosides (Sigma) | 7 | 26.7 | 43 | 4 | 0 | 0 |
| Ceramide trihexoside (Supelco) | 4 | 38.4 | 25 | 3 | 0 | 0 |
| Steryl glucoside (Supelco) | 6 | 46.8 | 0 | 5 | 1 | 0 |
| GANGLIOSIDES | | | | | | |
| GM1 | 8 | 38.4 | 37 | 2 | 3 | 0 |
| GM1 purified | 15 | 32.5 | 27 | 11 | 0 | 0 |
| GM3 | 14 | 29.1 | 50 | 6 | 1 | 0 |
| GM3 Purified | 17 | 29.1 | 47 | 8 | 1 | 0 |
| Made-up mixture GM1:GM3 (1:1) purified | 18 | 36.7 | 33 | 11 | 1 | 0 |
| PHOSPHOLIPIDS | | | | | | |
| Phosphatidyl-inositol (Sigma) | 10 | 28.7 | 60 | 4 | 0 | 0 |
| Sphingomyelin (brain) | 8 | 20.9 | 100 | 0 | 0 | 0 |

TABLE VI-continued

| COMPOUND | EGGS | A | % NEG | W | M | S |
|---|---|---|---|---|---|---|
| (Sigma) | | | | | | |
| Phosphatidylcholine (Sigma) | 10 | 33.4 | 40 | 6 | 0 | 0 |
| Phosphatidylinositol (Supelco) | 6 | 29.0 | 67 | 2 | 0 | 0 |
| Phosphoinositides (Sigma) | 3 | 31.1 | 33 | 2 | 0 | 0 |
| Phosphatidylinositol 4,5 diphosphate (Sigma) | 7 | 31.5 | 43 | 4 | 0 | 0 |
| Phosphatidyl inositol -4-monophosphate (Sigma) | 6 | 28.9 | 50 | 3 | 0 | 0 |
| Sphingomyelin (egg yolk) | 6 | 22.2 | 83 | 1 | 0 | 0 |
| Lysophosphatidyl choline stearoyl (Sigma) | | | 100% death rate | | | |
| NEUTRAL LIPIDS / NEUTRO LIPIDS | | | | | | |
| Mono, Di, and Tristearin (1:1:1) (Sigma) | 3 | 20 | 67 | 1 | 0 | 0 |
| Mono, Di, Triolein (1:1:1) (Sigma) | 2 | 0 | 100 | 0 | 0 | 0 |
| Tristearin (Sigma) | 21 | 36.5 | 43 | 8 | 3 | 1 |
| Triolein (Sigma) | 4 | 45 | 25 | 0 | 3 | 0 |
| Monostearin (Sigma) | 4 | 50.0 | 0 | 2 | 2 | 0 |
| Monoolein | 4 | 50.0 | 0 | 2 | 2 | 0 |
| Distearin (Sigma) | 3 | 26.7 | 67 | 0 | 1 | 0 |
| Diolein (Sigma) | 3 | 13.3 | 100 | 0 | 0 | 0 |
| Tripalmitin (Sigma) | 4 | 5 | 100 | 0 | 0 | 0 |
| Cholesterol palmitate (Sigma) | 3 | 0 | 100 | 0 | 0 | 0 |
| Triarachidin (Sigma) | 4 | 41.7 | 0 | 4 | 0 | 0 |
| Paraffin oil (Fisher) | 4 | 40 | 0 | 4 | 0 | 0 |
| STEROIDS | | | | | | |
| Ergosterol (Supelco) | 14 | 37.7 | 36 | 6 | 3 | 0 |
| Desmosterol (Supelco) | 4 | 26.7 | 50 | 2 | 0 | 0 |
| Lanosterol (Supelco) | 8 | 28.4 | 38 | 5 | 0 | 0 |
| Stigmasterol (Supelco) | 6 | 37.9 | 33 | 4 | 0 | 0 |

One skilled in the art will see that additional tissues, characterized by the presence of lipid and or ganglioside containing molecules, may be analyzed in this fashion to obtain potentially active fractions lipid containing and/or ganglioside-containing mammalian tissues, such as the liver, brain, epithelial tissue, and so forth, as well as plant tissues, especially seeds. Plants are known as good sources of lecithins, and angiogenically active bio- or organo synthesized lecithins may be found. Synthetically produced lipids may be used also. Other mammalian omental sources such as porcine, bovine, ovine or equine can be used as well.

A set of experiments was performed to demonstrate the neovascularization effects of the non-aqueous lipid preparation at a site where the normal vascularization in the tissue was purposely destroyed. Adult female cats were anesthetized with an intramuscular injection of Ketamine using a dosage of 7 ml/Kg. Each cat was placed in a supine position and an incision made between the knee and the inguinal crease of both hind legs. The femoral arteries were isolated, ligated, and removed between the groin and the first deep femoral branch (Hunter's canal). The incision was closed and each cat subjected immediately to an intravenous injection of stannous chloride/Technitium-99 which attaches to and radioactively labels the red blood cells in the tissue. The location and quantity of this radionuclide can be identified using a Gamma camera scan. In this matter, blood vessels and capillaries carrying the radioactively tagged red blood cells are specifically visualized.

The stannous chloride/phosphate preparation contained 10 mg of sodium pyrophosphate, 30 mg of sodium trimetaphosphate, and 0.95 mg stannous chloride. This preparation was reconstituted by adding 2.0 ml of PBS and 1.0 ml of this solution was injected intravenously into the bronchial vein of the cat. Twenty minutes later, an intravenous dose of 10 m Curries of Technisium-99 m was injected to radiolabel the red blood cells in that tissue area. Nuclear imaging scanning and digital integration of blood flow was observed and followed.

After the cats had been surgically prepared, a "baseline" scan for background radioactivity of the surgical sites was made, followed by injection of between 6-7 ml of the chloroform/methanol extracted and evaporated viscous liquid lipid suspended in PBS intramuscularly in equal amounts into two preselected and marked sites on the right leg in the area where the femoral artery was removed. A placebo injection containing only PBS was made into two similarly identified and marked sites on the left leg. Under normal circumstances, the recognized response of the body to this kind of surgery will be to try and establish collateral blood circulation to the injured tissues by forming new capillaries and blood vessels in the area where the femoral artery was severed. By following and comparing the rate and degree of new blood circulation in each leg following the surgery, a direct and verifiable assessment of the angiogenic properties and potency of the chloroform/methanol extracted lipid preparation was accurately made.

Figure 19:
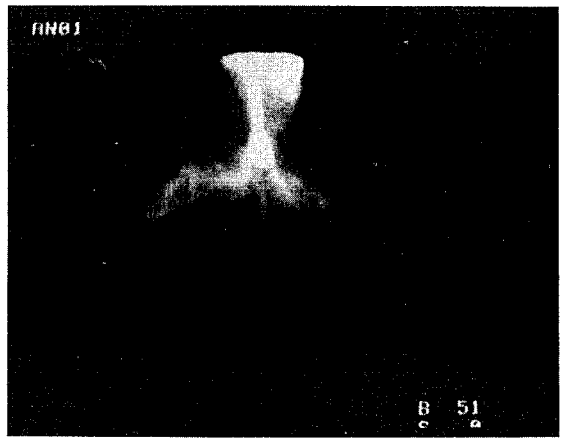
Figure 20:
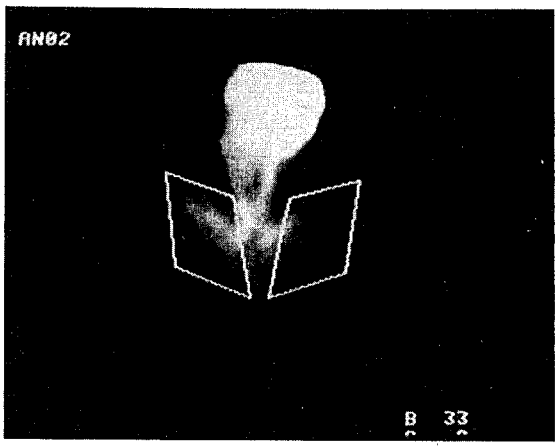
Figure 21:
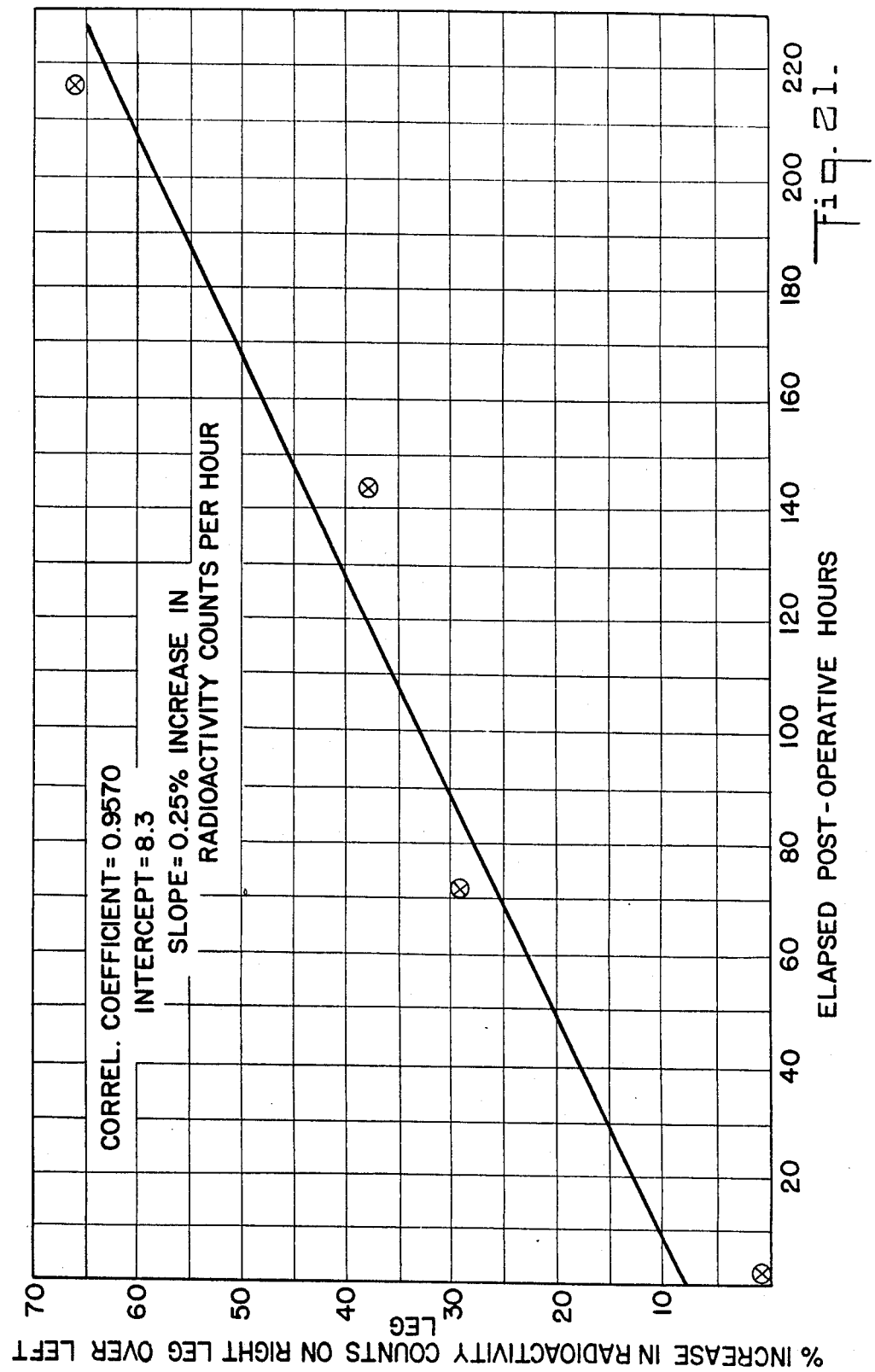

Subsequent intravenous injection of the stannous chloride/Technitium-99 m preparation was made into the preselected sites on each leg and each leg was subjected to nuclear scan at three, six, and nine days after the operation. The results of these nuclear scans are shown in FIGS. 18-20 which exemplify the effects of the lipid fraction for neovascularization in a representative cat. The data shows that the increase in blood vessel formation in the right leg of this cat (injected with the omental lipid preparation) and substantially higher integrated radioactivity counts then the left (control) leg. At seventy-two hours post surgery, a 29.6% difference in radioactivity was observed; at six days post operative time, a 38.2% increase in radioactivity was observed in the right leg in comparison to the left; and after nine days the rate of neovascularization in the right leg showed a 65.8% increase over that in the left leg. The photographs of FIGS. 18-20 provide visual evidence of the substantial differences in new blood vessel formation using the chloroform/methanol extracted lipid fraction. A graph illustrating a linear increase of radioactivity (in counts) comparing the lipid injected leg vascularization to the vascularization of the saline injected leg is provided in FIG. 21. The data reveals a rate of 0.25% per hour increase of neovascularization in the right leg compared to the left. This clearly shows the angiogenic effect of the lipid fraction as evidenced by the substantial increase in new blood vessel formation and vascular organization and structure in the right leg. This data however, overlooks the possibility of a common systemic effect by using the lipid extract preparation which was shown to be in effect by the following additional control experiment.

Figure 22:
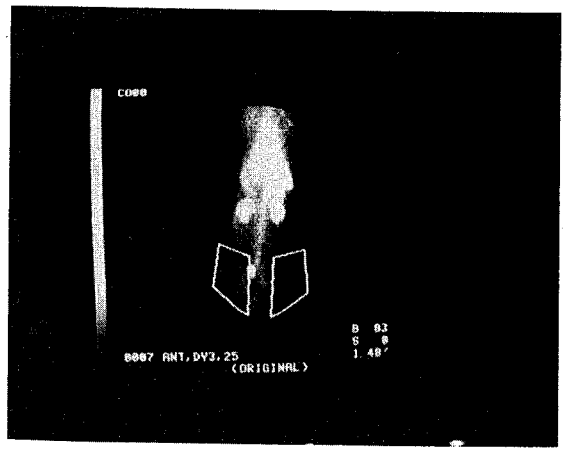
Figure 23:
Figure 24:
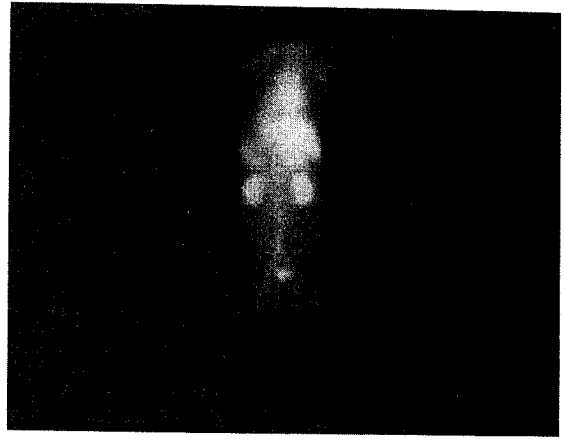

In this additional control, another cat was surgically operated upon to remove the femoral arteries as described above. But, in this instance, no injection of any kind was given. Gamma camera scans made at three and six day intervals post operatively are shown in FIGS. 22-24. The scan of the right and the left leg is shown in FIG. 22 in which no discernable difference in new blood vessel collateral circulation is visible after three days duration. FIG. 23 shows an anterior view of one leg on the sixth day post surgery and FIG. 24 shows the posterior view on the same day. The scan indicated no difference in counts between the two legs at any time post surgery and a much lesser degree of neovascularization in comparison to the earlier experiment. In fact, the neovascularization was noticeably less in this additional experiment than in the left (control) leg in the earlier work. In view of this and the fact that in the previous experiment that the left leg of the cat (injected control) exhibited a relatively higher degree of neovascularization (although substantially lesser than in the right leg), there is a basis for believing that part of the lipid preparation in the right leg was probably transferred systemically to the left leg in the earlier experiments.

The in vivo experiments, usng CMFr, may be repeated with the different materials obtained following hexane/ethanol extraction. As a comparison between these fractions and CMFr may be made from the data in Tables III–VII, supra, one skilled in the art will conclude that these purified extracts would result in even more rapid, and better angiogenesis. Compositions which possess angiogenically active lipid containing molecules have been obtained from mammalian tissues. The compositions, in therapeutically effective amounts, have been shown to affect angiogenic activity in a way not previously expected. Tissues similar to omentum, such as lipid containing mammaliam tissue and plant tissue, may be expected to have angiogenically active molecules as well. Synthetic lipids, based upon the structures of the molecules shown to be angiogenically active, are foreseen as well.

Other organic solvents can be used to extract omentum as well.

It is also possible to extract omentum using other organic solvents to obtain active angiogenic fractions. We also note the use of supercritical gas extraction for omentum factors as described in our co-pending application Ser. No. 793,622, filed Oct. 31, 1985 and hereby incorporated by reference.

Here a supercritical fluid (SCF) $CO_2$ is used to extract omentum. An SCF has increased solvation power at temperatures above the critical pressure (Pc) and critical temperature (Tc). Polar materials such as gangliosides remain in the residue while the extract contains the more non-polar or lipid materials such as triglycerides. For example, temperatures used are 38°–39° C. and pressures are 3500 psig. Thus these conditions can avoid with toxic materials extraction, toxic or inefficient extraction or use of expensive and time-consuming extractions and materials.

It is also possible to use detergents to isolate lipids from omentum. Lipids are displaced from homogenized cell membranes, or other complexes involving proteins, by amphipathic detergent molecules which render the proteins "soluble" in aqueous media. The released lipid material is recovered by flotation after centrifugation.

A list of possible detergents is given in Tables A and B below. These are used in concentrations ranging from 0.1 to 2.0% (w/v) and a pH from 7.0 to 8.0.

Cryogenic techniques can also be used such as subdivision of omentum in liquid nitrogen with subsequent use of the above or other extraction techniques. This is the subject of our copending application Ser. No. 811,507, filed Dec. 12, 1985.

TABLE A

DETERGENTS WITH FLEXIBLE HYDROPHOBIC REGIONS

| Detergent type | Structural formula | Formal (and trivial) name |
|---|---|---|
| Strongly ionic | (long alkyl chain)–O–S(=O)(=O)–O⁻Na⁺ | Sodium dodecylsulphate |
| | (long alkyl chain)–N⁺(CH₃)₂–CH₃ Br⁻ | Cetyltrimethylammonium bromide |
| "Weakly" ionic | (long alkyl chain)–N(CH₃)–C(=O)–CH₂–COO⁻Na⁺ | Sodium dodecyl-N—sarcosinate (sarkosyl) |
| Zwitterionic | (long alkyl chain)–N⁺(CH₃)₂–CH₂–CH₂–CH₂–S(=O)(=O)–O⁻ | Sulfobetaine (Zwittergent)[a] Palmitoyllysolecithin |
| | (long alkyl chain)–C(=O)–O–CH₂–CH(OH)–CH₂–O–P(=O)(O⁻)–O–CH₂–CH₂–N⁺(CH₃)₃ | |
| "Weakly" Zwitterionic | (long alkyl chain)–N(CH₃)₂→O | Dimethylalkylamine oxides (Ammonyx LO)[b] |

TABLE A-continued
DETERGENTS WITH FLEXIBLE HYDROPHOBIC REGIONS

| Detergent type | Structural formula | Formal (and trivial) name |
|---|---|---|
| Non-ionic | ~~~~~~~O—[CH$_2$—CH$_2$—O]$_n$H | Polyoxyethylene alcohol (Brij series, Lubrol W. AL. P series) |
| | ~~~~~⌬—O—[CH$_2$—CH$_2$—O]$_n$H | Polyoxyethylene nonylphenol (Triton N series Igepal CO series Surtonic N series Emulgen series) |
| Non-ionic with branched hydrophobic region | (branched)—⌬—O—[CH$_2$—CH$_2$—O]$_n$H | Polyoxyethylene p.t.octyl phenyl (Triton X series Igepal CA series Nonidet P40) |

[a] Available from Calbiochem-Behring, Serva.
[b] Available from Onyx Chemical Co., 190 Warren Street, Jersey City NJ 07032 U.S.A.

TABLE B
DETERGENTS WITH RIGID HYDROPHOBIC REGIONS

| Detergent type | Structural formula | Formal (and trivial) name |
|---|---|---|
| Strongly ionic | [steroid structure with OH, HO, OH and COO$^-$Na$^+$] | Sodium cholate |
| 'Weakly' ionic | [steroid structure with OH, HO, OH and C(=O)—NH—CH$_2$—CH$_2$—S(=O)$_2$—O$^-$Na$^+$] | Sodium taurocholate |
| Zwitterionic | [steroid structure with HO, OH and C(=O)—N—(CH$_2$)$_3$—N$^+$(CH$_3$)$_2$—(CH$_2$)$_3$—S(=O)$_2$—O$^-$] | CHAPS[a] |
| Non-ionic | [steroid glycoside structure with 2 Galactose, 2 Glucose, 1 Xylose, OH, OH] | Digitonin |

[a] 3-[(3-cholamidopropyl)dimethylammonio]-1-propanesulphonate, available from Calbiochem-Behring, Serva.

In practice, the compositions can be administered in any of the standard ways known to the art of pharmacology with appropriate carriers, combinations, inert substances, solvents and the like. These methods include intradermally, intravenously, intramuscularly, orally, and topically. The amount, or dose, will of course vary from patient to patient.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

EXAMPLE II

To test the possibility that angiogenic extract can promote healing and angiogenesis of a recent myocardial infarct (MI), the following experiments were done.

Twenty-four adult dogs on whom experimental acute MI was produced by balloon occlusion (n=3) or ligation (n=21) of the left anterior descending coronary artery. The angiogenic extract feline CMFr (n=12) or a control salinee solution (n=12) was injected IM daily, starting on day 1 of the MI and continuing for a total of 10 days.

After 4-5 days acclimatization, the following procedure was performed under sterile conditions: The heart was exposed by thoracotomy after anesthesia with IV pentobarbital 75 mg/kg, and the dog was ventilated with room air by respiratory pumps. In the first three dogs, after the pericardium was opened, a 3-5 mm balloon occluder (R. E. Jones) was placed along a dissected portion of the anterior descending coronary artery distal to the first diagonal branch. The chest was then closed and all catheters were exteriorized. The dogs were allowed 2 weeks convalescence while receiving a normal diet supplemented by tablets of NaCl 1 g/day to prevent sodium depletion. On the morning of the experiment, 2 cc of feline CMFr angiogenic extract or normal saline were injected interamuscularly. Two to three hours later, the balloon occluder was fully inflated to induce myocardial infarction in both controls and animals receiving the angiogenic extract.

In the next 21 dogs, acute myocardial infarction was induced by silk ligatures placed on the left anterior descending coronary artery according to the two-stage Harris technique [Circulation 1: 1318 (1950)]. The artery was dissected and ligatures were placed at the proximal and distal end of the vessel. A small clamp was attached and left hanging for ten minutes from the distal end to narrow the vessel without occluding it totally. After 10 minutes the ligatures were tied to occlude the vessel completely. The chest was then closed as above and all catheters were exteriorized. In these animals there was no need for a 2-week waiting period, so that the acute experiment began immediately.

The extract or saline injection was given daily by intramuscular injection (2 cc) for the next 10 days. At the end of the 10 day period, the dogs were sacrificed with an injection of pentobarbital, and hearts were removed for pathologic examination. Hearts were cut into transverse sections approximately 1 cm thick. Slices were examined and photographed to record the fresh appearance of the infarcted and non-infarcted areas. All slices were then incubated for 15 min at 35° C. in a phosphate buffered solution of nitro-blue tetrazolium (NBT), which produced an intense blue stain in undamaged parts of the heart, clearly outlining the areas of ischemic injury. These slices were rephotographed and then fixed in buffered formalin for further histological processing. The developed color macrophotographs were projected onto the magnetic tablet of a Zeiss MOP II image analyzer, where the infarcted vs. non-infarcted areas were traced and the volume of infarcted tissue was calculated as a percentage of the total ventricular muscle volume. In those with infarcts involving 9% or more of the ventricular myocardium, hematoxylin- and eosin-stained sections were prepared from NBT-stained (A) and unstained (P) regions of the myocardium and of the lateral and septal border zones (LB, SB) to permit microscopic assessment of signs of injury, angiogenesis, penetration of infarcted areas with living cells, cellular organization, collagen formation and other criteria of the progression and degree of healing.

Histologic stains used include:

Hematoxilin/Eosin (HE):

Staining viable cell nuclei blue, cytoplasm pink, dead cells intense red ("eosinophilic"), red cells red, and collagen light pink.

Fibrin-Trichrome, modified(F):

Staining viable nuclei purple, viable cytoplasm red, dead cells grey, red cells yellow, fibrin bright red and collagen green.

Below in Table VII is seen the estimate of infarct size for each dog.

TABLE VII

| ESTIMATE OF PERCENT INFARCT VOLUME | | |
|---|---|---|
| DOG # | ID # | % INFARCT |
| 1 | 9638 | 19% |
| 2 | 10585 | 4%+ |
| 3* | | |
| 4* | | |
| 5 | 10597 | 7%+ |
| 6 | 10594 | 9% |
| 7 | 10598 | 23% |
| 8 | 10595 | 16% |
| 9 | 514 | 13% |
| 10 | 333 | 18% |
| 11 | 683 | 21% |
| 12 | 633 | 19% |
| 13 | 323 | 20% |
| 14 | 71098 | 12% |
| 15 | 11024 | 6%+ |
| 16 | 10824 | 16% |
| 17 | 75356 | 15% |
| 18 | 11378 | 2%+ |
| 19 | 11653 | 31% |
| 20 | 10852 | 13% |
| 21 | 10557 | 21% |
| 22 | 10665 | 19% |
| 23 | 77745 | 9% |
| 24 | 11045 | 19% |

*Dogs 3 and 4 died spontaneously before the 10 day period, no tissue was taken.
+Infarct size less than 9%.

Histological Observations

All hearts were coded and sent for blind histologic study to determine experimental vs. control. The specific histologic criteria which was used in the assessment of would healing in infarcted dog hearts (10 days after coronary artery ligation): perfusion, vascularization, and collagen organization:

(1) PERFUSION: A search was made for fresh, non-hemolized, non-clotted blood distributed along old vascular channels in the necrotic center of the infarct area. Their presence indicated that blood supply had been re-established in tissue which (by definition) had died because of a temporary absence of blood flow. A vascular distribution pattern (as opposed to plain diffuse bleeding) was important since living regenerating cells were seen located along such vascular channels, if they are perfused. Large amounts of vascular channels filled with fresh blood within the necrotic area and deep penetration of this area with viable regenerating cells was considered a positive criterium for optimal or even accelerated wound healing.

(2) VASCULARIZATION: The density and maturity of blood vessels in the granulation tissue at the border zone between necrotic and living heart muscle cells was assessed. A high density of vessels with many vascular profiles showing a multilayered vessel wall and foci of capillaries displaying a hemangioma-like pattern were considered positive indicators of the vascular component of wound healing, or angiogenesis.

(3) COLLAGEN ORGANIZATION: At the border of the infarcts, the regenerating tissue appeared very cellular; as cells produce collagen, these areas become more fibrilar than cellular and acquire tensile strength in this way. Predominance of highly organized fibrillar areas over cellular ones in the periphery of the infarct was evaluated as an indicator of an advanced component of the wound healing process.

These criteria were used only in the context and as a part of an overall pathologic-anantomic evaluation of the healing process by two experienced cardiovascular specialists.

The non-edited transcripts of the original pathology reports are as follows including a gross description of same with some description of gross photos of the hearts, together with a series of microscopic descriptions referring to a series of micrographs, (dogs 1-8), microscopic descriptions (dogs 9-24).

Each individual section and then the overall impression for the entire hearts were rated as follows based upon degree of perfusion, neovascularization and collagenization:

(1) poorest healing, must be untreated
(2) no convincing change, most likely untreated
(3)— some change, but could well be within usual variations, probably untreated
(3) completely equivocal cannot tell whether treated or untreated
(3)+ changes allow educated guess only, maybe treated
(4) advanced healing by serveral criteria, likely to be treated
(5) impressive acceleration, must be treated

PATHOLOGIC-ANATOMICAL EVALUATION DOG HEARTS

Dog 1 9638

Dog 1

Gross Description

Fresh heart with balloon in situ in LAD.
Surface smooth and glistening.
Pale area in anterior LV and apex.
On section there is a well demarcated anterior-lateral infarct which is unusually red, does not stain with nitro blue tetrazolium (NTB) and involves an estimated 19% of the muscular volume. (i.e. 19% of total cross-sectional area on wall 61 cm slices through both ventricles were non-blue=non viable.)

Gross Photos

1. Front view, fresh heart
2. Fresh slices through both ventricles
3. Same, after NTB reaction (blue=non-infarcted, brownish-red=infarcted)
4. Same, after fixation and removal of specimens for histology:
P=non-infarcted area (posterior)
L=border zone (lateral)
A=middle of infarct (anterior)

Microscopic Description

Specimen P (posterior)
  Photo 5: longitudinal sections show slightly congested, but otherwise normal myocardium.
  Photo 6: cross sections show same.
  Photo 7: high power of NTB positive viable myocardium. The NTB stains only the most superficial cells.
Specimen L (lateral)
  Photo 8: few fibrocellular patches present.
Specimen A (anterior)
  Photo 9: low power: necrotic myocardium, hemorrhagic infarct border, and peripheral fibrocellular organization.
  Photo 10: center of infarct showing necrotic muscle with extensive hemorrhage, no cellular organization.
  Photo 11: hemorrhagic and congested interface between dead muscle and organizing fibroblasts.
  Photo 12: detail, center of infarct, no viable tissue, no organization, much hemorrhage and hemolysis.
  Photo 13: detail of fibroblastic organization.
  Photo 14: arterioles, microhemorrhage, necrotic myocardium and organizing fibroblasts.
  Photo 15: longitudinal sections through partially wavy, necrotic myocardial cells, with inflammatory cells, extravasated blood, and occasional fibroblasts, close to center of infarct.

Dog 2 10585

Dog 2

Gross Description

Fresh heart, balloon in situ in LAD.
No significant epicardial changes.
Slices show small patchy areas which are only partially NTB negative, in a circular, mid-muscular pattern and on a papillary muscle. Estimated 4% of all cross-sectional areas are NTB negative (i.e. non-viable).

Gross Photos

1. Frontal view of fresh heart.
2. Fresh slices, homogeneously brown (whitish patch on largest slice is part of valve ring at base of heart).
3. Same, after NTB stain. Non-stained areas barely visible.
4. Same, after fixation and removal of samples for histology (from slice just above blue labels).
Weaker NTB staining visible at few places.

Microscopic Description

Specimen P (posterior)
  Photo 5: cut surface of essentially normal myocardium showing the positive NTB reaction (viable cells, bluish reaction product) in the uppermost cell layer.
  Photo 6: cross section through essentially normal myocardium. Red "dots" represent capillaries which are filled and occasionally overfilled with red cells indicating mild congestion.

Photo 7: same as 6, longitudinal sections.

Specimen L (lateral)

Photo 8: low power overview showing large area of slightly congested but otherwise normal myocardium.

Specimen A (anterior)

Photo 9: low power overview of essentially normal myocardium.

Photo 10: high power shows occasional eosinophilic (pinker) myocardial cells, indicating individual cell damage.

Dog 5 10597

Dog 5 (7% NTB)

Gross Description

Fresh dog heart with ligated LAD.
Small scar at ligation site.
Patchy paleness of anterior apical surface, with dull surface areas.

Gross Photos

1. Fresh heart, front view, ligature scar visible in LAD. Note pale, dull patches on anterior and apical ventricular surface.
2. Rear view of fresh heart.
3. Fresh slices through myocardium. Note that anterior (A) and posterior (P) sides are not always oriented in the same direction.
4. NTB reaction on fresh slices. A=front anterior; P=posterior.
5. Same, after fixation and removal of histologic specimens.
   P=posterior
   L=lateral
   A=anterior

Microscopic Description

Specimen P (posterior)

Photo 6: essentially normal myocardium longitudinally sectioned with arterioles and capillaries.

Photo 7: high power cross-section of same.

Photo 8: high power longitudinal section of same. Note mitosis (?endothelial) at arrow.

Specimen L (Lateral)

Photo 9: acute and chronic pericarditis, epicardial fat, nerve, and vessel, unaffected subepicardial myocardium.

Photo 10: oblique section through essentially normal myocardium. Note the capillary pattern.

Photo 11: essentially normal myocardium, longitudinal

Specimen A (anterior)

Photo 12: acute and chronic pericarditis with extensive vascularization. Normal coronary artery. Organizing myocardial infarct.

Photo 13: necrotic myocardium (red patches), cellular organization with fibroblasts, blood vessels, and some collagen (pink). Calcification (blue patches). Endocardium at arrow.

Photo 14: detail of mostly cellular (fibroblastic) organization. Remaining necrotic myocardium at arrow. Microhemorrhages in center (individual extravascular red cells).

Dog 6 10594

Dog 6 (9% NTB)

Gross Description

Fresh, relatively small dog heart, ligature in situ at LAD.
Petedinal epicardial hemorrhages along LAD.
Pale, dull patches on anterior surface toward apex.

Gross Photos

1. Front view of fresh heart, with LAD ligated.
2. Rear view of same.
3. Fresh myocardial slices.
   A=anterior, P=posterior
4. NTB reaction on fresh slices.
   Note clear demonstration of infarct.

Microscopic Description

Specimen P (posterior)

Photo 5: essentially normal myocardium, longitudinal.

Photo 6: single small focus of fibrosis and necrotic myocardial cells.

Specimen L (lateral)

Photo 7: cross-section through viable myocardium of lateral left ventricular wall. Positive NTB reaction visible as blue cellular stain in corner. Capillaries are prominent and filled or overfilled with red cells (red dots). Arteriols show thickened (hyperplastic) walls.

Photo 8: Markedly thickened arteriolar wall and capillary congestion.

Photo 9: extensive smooth muscle hyperplasia of arterial wall, and congested capillaries. Cross-sectional muscle cells essentially normal.

Specimen A (anterior)

Photo 10: acute and chronic pericarditis, normal coronary artery, totally infarcted myocardium.

Photo 11: enter of infarct, thin necrotic myocardial fibres (without nuclear staining), minimal reaction except for few disintegrated polymorphonuclear leukocytes in blue periphery. No vascularization in this control area.

Photo 12: peripheral area of infarct with necrotic myocardium partially infiltrated by polymorphs. Organizing granulation tissue is mostly cellular (fibroblasts) with some early collagen and usual extent of vascularization.

Photo 13: necrotic myocardium near center of infarct, few disintegrating polymorphs, some extravascular red cells, no new vessels.

Photo 14: very active and cellular organizing area at infarct periphery. Few necrotic muscle cells, predominance of activated fibroblasts, red cells inside and outside of capillaries, few polymorphs.

Photo 15: very fibrous area of organization, mostly collagen. Predominant cells are activated fibroblasts. Vessels are thick walled arterioles and venules, without much congestion and without prominent capillaries.

Dog 7 10598

Dog 7 (23% NTB)

Gross Description

Fresh dog heart with ligated LAD. Microhemorrhages, superficial paleness and dullness along LAD.

Apical yellow area demarcated with red, hemorrhagic border zone.

Gross Photos

1. Front view, fresh specimen with ligature of LAD and epicardial, apical, and anterior changes.
2. Rear view, some lateral apical paleness. Whitish cloudiness of pericardium.
3. Fresh myocardial slices. Note the extent of the mottled yellow-red infarcted area.
4. NBT reaction. Note total infarction (yellow-red), mildly ischemic (?) zones (brownish-blue), and normal zones (blue). Only total infarct was measured.
5. Same after fixation and removal of histologic specimens.

Microscopic Description

Specimen P (posterior)
 Photo 6: unaffected myocardium, longitudinal.
Specimen L (lateral)
 Photo 7: acute and mild chronic periconditis, normal coronary vessel, fibrous and cellular organization, hemorrhagic border zone, few polymorphs, and necrotic myocardium in typical layering.
 Photo 8: typical view of border zone between dead muscle (red) and reactive organizing granulation tissue. A few vessels penetrate into the dead tissue (arrow) but not into its full depth. There is little polymorph reaction (i.e., no remarkable bluish border zone) and at this place, vascularization of granulation tissue is not overwhelming. There is little extravasation of red cells and no hemorrhagic or congested border zone.
 Photo 9: different organizing area shows less necrotic muscle, more vascularization, more hemorrhage than area on photo 8; there is also a focus of calcification (blue).
 Photo 10: totally necrotic myocardium, near center of infarct, with a few disintegrating polymorphs, sparse round cells, extravascular red cells, and the most advanced viable blood vessels.
 Photo 11: necrotic muscle at organizing zone, partial fibroblastic organization, partial hemorrhages into dead tissue.
 Photo 12: similar to photo 11, with focus of calcification. Red cells are in- and outside of blood vessels.
 Photo 13: typical active cellular organization at border of necrotic myocardium. Extravasation of individual red cells is clearly visible. Remaining necrotic muscle cells are surrounded by active fibroblasts.
 Photo 14: detail of calcification and bleeding within organizing tissue.

Dog 8 10595

Dog 8 (16% NTB)

Gross Description

Fresh dog heart with LAD ligature. Epicardial hemorrhages; pale and dull surface anterior and apical.

Gross Photos

1. Front view, fresh specimen, with LAD ligature, dull, pale surface anterior-apical, and red subepicardial bleeding.
2. Posterior view, pale lateral apex.
3. Fresh myocardial slices. A=anterior side (with infarct).
4. NTB reaction on fresh myocardium. A=anterior (with infarct).
5. Same, after fixation and removal of histologic specimens:
 A=anterior
 L=lateral
 P=posterior

Microscopic Description

Specimen P (posterior)
 Photo 6: essentially normal myocardium cross-sectioned.
Specimen L (lateral)
 Photo 7: essentially normal myocardium, low power, with penetrating artery, arterioles, and capillaries.
Specimen A (anterior)
 Photo 8: border of necrotic and organizing tissue within infarcted area. Typical fibrocellular organization, moderately vascular, no bleeding; very few polymorphs
 Photo 9: pericardium, with acute and chronic pericarditis. Note round cell infiltrate, marked vascularity, and underlying necrotic myocardium.
 Photo 10: organizing tissue with unusual prominence of arterioles and other blood vessels.
 Photo 11: Focus of calcification in advanced, collagenous and cellular fibrotic organizing tissue, consistent with early scar formation.

Dog 514

DOG 9

Slide 933: Posterior control segment
 unremarkable myocardium
 no special vascular pattern
Slide 932: Anterior, center infarct
 total infarct, with good perfusion of old channels, but atypical pattern and no reaction by living cells
 Eval: equivocal
Slide 934: Lateral border
 very cellular reaction, with good ingrowth of viable cells into dead area
 perivascular areas show mature collagen
 many polys present
 large patches of reactive fibroblastic cells also embedded within adjacent noninfarcted myocardium
 Eval: increased activity, likely to be treated
Overall Evaluation: likely to be treated. (Note: mostly based on border zone; center of infarct less convincing in review.) Rating=4

Dog 333

DOG 10

Slide 935: Posterior, control segment without infarct
 normal myocardium
Slide 936: Lateral border
 infarcted part not on slide
 myocardium unremarkable
 Eval: not applicable
Slide 937: Center infarct, anterior
 dead area poorly perfused
 cellular ingrowth not much advanced
 areas with collagen rare, immature vascularity of granulation tissuue varied
Eval: must be control
Overall evaluation: Untreated; must be control.
Rating=1
Dog 683

DOG 11

Slide 938: Posterior control segment unremarkable, intact myocardium. No special vascular pattern
Slide 939: Lateral wall, border zone
active perfusion
dead muscle entirely penetrated by living cells following channels
high cellularity and vascularity of regenerating tissue
most advanced collagen is in thick bundles with relatively few remaining cells, but areas in between are still very cellular; small focus of calcification
Eval: definitely treated
Slide 940: Anterior, center infarct
extensive reperfusion pattern of old channels
living cells penetrating deeply into dead area
"picture book" intensive regeneration pattern
some, but not all, regenerating areas with high vascularity and mature vessels
collagen advanced only in periphery; some of the dead muscle has also a greenish tint on this stain
Eval: definitely treated
Slide 956: Recut; septal border zone, slice #4
very active regeneration, qualitatively similar to 939
Eval: treated
Slide 957: Slice #5, center infarct (anterior) recut
very active breaking pattern
has areas of vascularity resembling the pattern of hemangiomas
Eval: treated
Slide 958: Addition cut, slice #6, anterior (center infarct)
similar to 939, with some more dead material
Eval: treated
Overall evaluation: Definitely treated (most active within this group of five dogs #s 9–13). Rating=5
F Dog. 333

DOG 12

Slide 941: Posterior control segment: unremarkable
Slide 943: Anterior, center infarct
some areas with very good perfusion of old channels, but others insufficient; more polys and unclear dust than usual both in channels and periphery
regenerating cells present, but not following channels very far
new vessels present
some thick strands of collagen close to dead tissue
Eval: equivocal
Slide 942: Lateral border
small area with extensive infiltrate of inflammatory round cells and high vascularity, but not much repair
Eval: not typical, questionable. Inflammation?
Slide 959: Lateral border of infarct, slice #4
extensive acute and chronic pericarditis
advanced healing, very cellular and very vascular
yet necrotic, partially perfused areas immediately adjacent
collagen reasonably advanced, but green is overstained at places
Eval: may be treated
Slide 960: Septal border, slice 4
florid pericarditis
active healing pattern, but still relatively large necrotic areas.
Eval: may be treated, but inflammation obscures picture.
Slide 961: Center infarct, anterior, slice 2
large dead area, often poorly perfused
many polys, and unclear dust
regeneration only in a small rim, not very active
large thrombosed vessels in center
Eval: inflammatory, no effect of treatment recognized
Slide 962: Center infarct, anterior, slice 1
very necrotic, little recognizable activity
Eval: probably not treated
Overall evaluation: probably not treated. Rating=2
Note: on review of additional sections (after disclosure of code) the activity may have been underestimated originally; the specimen is unusual and difficult to read because of the presence of many more acute inflammatory cells than usual. Sections 943 and 960 would probably be evaluated as showing treatment effects if reviewed again as unknowns.
Dog 323

DOG 13

SLIDE 944: Posterior left ventricle: non-infarcted control section
unremarkable
Slide 945: Lateral border, left ventricle
patchy, often band-like interruption of necrotic areas by regenerating tissue
perfusion of old channels so-so
maturity of regenerating tissue and collagen average
vascularity high
Eval: may be treated
Slide 946: Anterior, center of infarct
relatively consistent perfusion pattern in all necrotic areas, but not too impressive in detail
good follow-up with sickle cells
vascularity and collagen maturation average
Eval: possibly treated, but little effect
Slide 963: Lateral border, slice #4
moderate, average regenerative reaction
Eval: equivocal
Slide 964: Septal border, slice 4
intensive cellular and vascular reaction
collagen not advanced, however
perfusion of dead material average, but many individual islets of viable cells are present
Eval: maybe
Slide 965: Anterior, center infarct, slice 5
some areas with impressive penetration by viable cells
otherwise equivocal
Eval: average
Slide 966: Anterior, infarcted, slice #6
good penetration by viable cells
good perfusion
very cellular repair, without much mature collagen
vascularity average
Eval: may be treated Overall evaluation: considered treated but with weak effect (educated guess). Rating=3+
A anterior (and number of slice)
S septal
SB septal border
LB lateral border x photo
Dog: 71098, 12% Infarct Dog 14

1001 A3
  Not all of section infarcted
  No dead tissue, no revitalized channels; polys scarce
  Loose early fibrosis, vascularity not impressive.
1002 lateral L3
  Essentially normal myocardium; no infarct, no reaction.
  see LB lateral border
1003 septal S3
  No infarct
1004 A2
  Small areas of total, non-removed infarct
  Channels partially utilized
  Mostly cellular reaction, with macrophages
  Vascularity of reaction is moderate overall
  Collagenization moderately advanced
  Perfusion relatively poor
1005 Lateral border LB2
  Very little dead material left
  Little utilization of channels in dead material
  Good cellular granulation tissue, but not impressively vascular
  Poor following of channels by fibroblasts, but there is some interlacing in the viable muscle areas
  Collagenization not far advanced.
1006 Apex A1
  Not infarcted
1007 Liver
  Congestion
  Mild focal fatty change or glycogen
1008 Muscle injection site
  Perfectly normal skeletal muscle
1009 Muscle control
  Normal skeletal muscle, poor section
Overall impression of dog 14: must be a control. Rating=1.
Dog: 11024, 16% Infarct Dog 15

1010 Anterior A3
  Sizable dead area, with slightly above average usage of old channels
  Advanced collagenous organization from the epicardium (grossly white rim) interdigitating with live and dead muscle fibers
  Scattered foci of myxomatous loose early connective tissue way within dead area, with occasional microhemorrhage into it, and faint green early collagen.
  Neovascularization in these areas prominent, with collagen around each arteriole
  Eval: shows signs of treatment
1011 LB lateral border
  Small rim of cellular and loose collagenous organization
  Some macrophages
  Vascularization not impressive
  Adjacent muscle unremarkable
  Very few individual dead fibers
  Eval: not impressive in overall "effect" but too small an area
1012 Septal border 3, SB3
  Good layering from dead muscle to cellular to fibrous regeneration to normal muscle
  Channel re-utilization prominent in dead area
  Cellular reaction vigorous, but not far extending
  Relatively well formed collagen, not overwhelmingly however
  Vascularity not impressive, about average
  Green overstained
  Eval: equivocal
1013 Anterior A2
  Mostly dead muscle with small (white) rim pericardial.
  Prominent channel reperfusion
  Vigorous cellular regeneration, but not too much interdigitation
  Advanced, mature collagenous organization subepicardial
  Prominent vascularization in one corner
  Eval: very likely treated
1014 Anterior A1
  Few scattered dead fibers left, no old channels
  Very dense cellularity around dead material
  Advanced and highly organized fibrocellular regeneration with mature collagen
  Small rim with original viable muscle
  Vascularity in cellular areas impressive, but seems already to disappear in the most collagenous parts
  Epicardial advanced collagenous scar.
  Eval: advanced healing, likely treated
1015 Liver
  Uniformly fatty liver (or glycogen?) with much acute congestion
1016 Muscle, injection site
  Part skeletal muscle, part fat
  No reaction
1017 Muscle, control
  Identical to above, also with fat
Overall eval Dog 15: likely to be treated Rating=3+
Dog: 10824, 16% Infarct Dog 16

1018 A3 anterior
  Much dead material
  Moderate channel reperfusion
  Interdigitation of regenerating cells along channels present, but not overwhelming
  Regenerating tissue more cellular than fibrotic
  Vascularity average at best
  Eval: may or may not be treated
1019 LB3
  Poor sections, recut
  Effect does not seem extraordinary
  Little dead material
  Much fibrosis, relatively loose, with average amount of vessels and cells
  Eval: insufficient
1020 SB3
  Impressive reperfusion of small dead area
  Loose to medium organized regenerating tissue
  Small foci of above average vascularity
  Maturation of collagen not impressive
  Eval: some signs of treatment, but weak
1021 A2 anterior Large necrotic zone with good reperfusion (of dead channels) by living cells. Few polys.
Cellular organizing tissue with slightly increased vascularity; some very prominent thick-walled arterioles
Collagen development moderate to advanced
1022 A1 Anterior
  Cellular regenerating tissue interlacing with normal fibers. No dead material
  Overall organization advanced, with many prominent thick-walled arterioles
  Foci of very mature collagen and decreased cellularity
  Vessles good for photo on "fibrin" stain and somewhat less on PTAH photo
  Eval: some signs of treatment
1023 Liver
  Extensive congestion both hemolytic and fresh blood
  All cells ballooning (fat or glycogen or both)
1024 Muscle injection site
  Negative
1025 Muscle control
  Negative. A large artery and a nerve also entirely normal.
Overall eval Dog 16: likely treated, but not with maximum effect Rating=3+
Dog: 75356, 15% Infarct

Dog 17

1026 A3 anterior
  Small areas of dead muscle very actively perfused; subdivided into patches by actively growing regenerative tissue; also appears loosened.
  Active and very vascular regenerating tissue, with far advanced fibrous organization at several places, and very cellular and vascular spots elsewhere
  One place looks like a hemangioma.
  x photo
  Eval: definitely treated
1027 Lateral border LB3 (third slice)
  Similar to 1026, with some intact muscle which shows no altered number and distribution of vessels.
  It's all in the regenerating tissue, starting from the pre-existing vessels and the epicardium
  Eval: definitely treated
1028 SB3 septal border
  Interesting area of fragmentation of dead material by perfused and nonperfused channels
  Vigorous active vascular regeneration tissue with several collagenized areas and very prominent vessels
  Thick-walled arterioles prominent
  Again noninvolved muscle absolutely unremarkable
  whole HE fibrin stain good
  Eval: as above
1029 Posterior P3
  Some subepicardial patches of fibroblasts (age? general ischemia?, activation by treatment of spontaneous ischemic lesions?
1030 A2
  Large infarcted area in the active reperfusion and good interdigitation of live regenerating cells
  Microhemorrhage present
  photo
  Vascularity of surrounding advanced regenerating tissue increased
  Patches of mature collagen very small, peripheral
  Eval: definitely treated
1031 A1
  Patchy dead zones; perfusion of channels present, but not as regular as other slides
  Good interdigitation between breaking necrotic material and regenerating live cells and vessels
  Some mature collagen, but mostly cellular
  Eval: treated
1032 Liver
  Pronounced clearing and ballooning of cells
1033 Muscle injection site
  No significant reaction
Overall evaluation of Dog 17: definitely treated, with good effect, Rating=5
Dog: 11378 2% Infarct

Dog 18

1034 A3
  Perfusion of old channels positive
  Necrotic material breaking up
  Active, vascular regenerating tissue with advanced organization
  Eval: treated
1035 Lateral border third slice LB3
  Similar; little dead tissue; vessels not so impressive
  Eval: treated (probably)
1036 Septal border
  Looks like a hemangioma, although some might be microhemorrhage
  One spot (arrow): dense accumulation of vessels without blood
  photo
1037 A2
  As in A3, all criteria of treatment are present
  Eval: treated
  photo
1038 A1
  It really looks as if the vessels break up the little remaining dead material; neither polys nor macrophages are prominent
  Enzymes stains a must
  Eval: treated, definitely
1039 Liver
  Very congested and partially hemorrhagic, but little of the ballooning clear cell phenomena
1040 Muscle, injection site
  Somewhat widened interstitium, otherwise normal
1041 Muscle control same
Overall evaluation Dog 18: treated with good, but not great, effect, Rating=5.
Note: Gross infarct size too small, but could this be an additional effect of treatment? (Must know infarct size at beginning of experiment)
Dog 11653, 31% Infarct!

Dog 19

A1 Anterior, slice one (center of infarct)
  Necrotic zone with subendocardial and subepicardial granulation tissue
  Dead: large channels perfused, but not capillaries
  Granulation tissue not advanced, not overly vascular
  Fibroblasts not penetrating far into nercrosis along channel Polys few, subepicardial, not reaching necrosis well Collagen reasonably well developed, only perivascular and subendocardial Fibrin: (on PTAH) some fibrinous pericarditis, not much intravascular Eval: unremarkable healing pattern, poor perfusion A2 Anterior, slice two (center of infarct)

Very similar to A1; mostly necrotic with very small rim of granulation tissue.

Some calcification

Poor penetration of dead tissue by cells; neither much polys nor much fibroblasts No good perfusion pattern; some intravascular fibrin present Eval: poor healing, insufficient reaction, must be control A3 Anterior, slice three Like A1 and A2. Some interstitial fibrin.

Eval: control

SB3 Septal border, third slice

Extensive, non-perfused necrosis, few polys, some disintegrating to "nuclear dust".

Patches of granulation tissue which contain quite dense, relatively mature vessels, however.

Sharp demarcation to totally inert, normal muscle, no increased vascularization nor perfusion in live part of border zone (best on PTAH)

Collagen not advanced; some fibrin in dead side vessels of border

Eval: poor healing, despite some dense mature vessels

B3 Lateral free wall with infarct border zone

A single field within dead tissue shows increased perfusion, rest is poorly perfused and poorly penetrated by live cells; especially few polys.

There is some interdigitation between necrotic material and granulation tissue, but not impressive Vascularity of granulation tissue is moderate Collagen is mature only around a large preexisting vessel, reaction overall is still very cellular, with little collagen Sharp border to living muscle, which looks normal Eval: little effect Overall Dog 19: control (even considering that this animal had the largest infarct so far). Rating=1.

Dog: 10852, 13% infarct

Dog 20

A1 Anterior, slice one

Little necrotic tissue, completely interdigitating with living cells, vessels, but little blood (good for photo of this aspect)

Quite vascular granulation tissue, more cellular than collagenous

A very vascular spot of loose fibrosis totally surrounded by normal tissue (microinfarct?)

Collagen far advanced and dense even in close vincinity of the few remaining dead fibers→ photo Eval: much activity and advanced healing A2 Anterior, slice two Perfused necrotic tissue with good ingrowth of individual live cells, cell cords and vessels Advanced collagenation Very vascular with varied stages of vascular wall maturation; no unusual dense accumulation spots however A3 Anterior, slice three (this level corresponds to the one used in earlier evaluations)

Totally dead areas hard to find; almost all is either perfused or interupted with regenerating cells Active looking granulation tissue Collagen is dense only at subendocardial and perovascular places, but faint positive stains penetrate throughout necrotic area Occasional perivascular fibrin around vascular channels passing through dead material Eval: not likely treated SB3 Septal border Wide area of extensive interdigitation of dead and regenerating tissue, very vascular Remainders of dead tissue look perfused although no capillary pattern can be recognized Selected areas show "crowding" of vessels, thin- and thick walled ones ("hemangiomatous"?)

Very questionable increase in perfusion of live muscle

Areas with mature collagen easy to find

Eval: treated

LB3 Lateral border, slice three

Similar to SB3

Every capillary profile in the live tissue has a red cell in it; maybe increased perfusion? without increased vessels there?

Collagen quite mature; at places also surrounds individual living muscle fibers! Follows vessels and cells far into necrosis Eval: advanced response Overall Dog 20: very likely treated Rating=4

Gavra's 10557, 21% Infarct

Dog 21

A1 Anterior, slice one

Large thrombus (mural) with organizing fibrin

No capillary pattern in necrotic areas

Average activity of granulation tissue

Collagen not very dense

Vascularity dense, but not very mature, in several areas

Eval: equivocal

A2 Anterior, infarct center

Necrotic material partially perfused, but large areas totally cut off

Unnusual amounts of polys penetrating much more than fibroblasts do

Granulation tissue active, but not overly vascular

Perivascular fibrin in some large dead channels within necrotic tissue

Eval: weak reaction; more dissolving than regenerating

A3 Anterior, slice three, infarct center

Large necrotic area, poorly perfused, with minnimal rim of subendocardial granulation tissue Vascularity poor: penetration by vessles, cells minimal. No interdidpitations. Collagen weak. One clotted ateriole.

Eval: poor response; no effect what so ever

SB3 Septal border, slice three

Poor perfusion of necrotic material, much nuclear dust from polys instead

Small rims of poorly interdipitating and poorly
    vascular granulation tissue
  Eval: healing and organization not advanced
LB3 Lateral border, slice three
  Impressive cellularity of granulation tissue, but
    little vascularity and little maturation
  Several spots of very loose fibrosis with very small
    capillaries
  Eval: healing and organization not advanced
Overall Dog 21: unimpressive, probably control Rating=2
Dog 10665, 19% Infarct

Dog 22

A1 Anterior, center infarct, slice one
  Small specimen, not much necrotic tissue
  Reutilization of old channels not impressive
  →but fibroblastic penetration along old channels
    deep into dead tissue is noticeable
  Eval: could be treated
A2
  Much interstitial blood, fresh, but not in channels
  More polys than usual
  Fibroblastic ingrowth only focally
  Some larger vessels have polys in the wall (vasculitis)
  Eval: equivocal
A3
  Relatively large necrotic zone without perfusion
  Fibroblastic ingrowth at border good
  Many vessels with vasculitis and thrombosis, fresh
  Granulation tissue cellular and reasonably vascular
  Collagen moderately well developed along vessels
  Subepicardial bleeding present
  Eval: equivocal and distorted by ?infection
SB3
  Dead areas with good reperfusion
  Active interdigitation of reactive live tissue and
    dead area
  Granulation tissue very vascular at places
  Areas with advanced collagen organization are
    present but not predominant
  Eval: advanced healing
LB3
  Some reutilization of channels present
  Fibroblast penetration not deep
  Healing tissue organization moderate, with average
    vascularization
  Collagen not advanced; most regenerating areas
    still very cellular
  Eval: weak change if any
Overall Dog 22: weak change; treated but probably
  with little effect. Rating=3+
Dog 77745, 9% Infarct

Dog 23

A1 Anterior, slice one, center infarct
  Very few, small islands of necrotic tissue left
  Vascular channels within dead tissue do not have
    reperfusion patterns, but infiltrating living cells
    instead (endothelium and fibroblasts, not polys)
  Granulation tissue very vascular, with may mature,
    arteriole-type vessels
  New: between granulation tissue and preexisting
    live muscle cells, there is a layer of ballooning
    muscle cells (hydropic change)
  Collagen is very mature, highly organized
  Eval: advanced healing (but small infarct!)
A2
  Vascular channels in necrotic area well reutilized;
    live cells following closely, but there is still a
    dead center with only a few polys
  In two areas, vascularization in the regenerating
    tissue is almost hemangiomatous, but also with
    microhemorrhage.
  Granulation tissue activity high, much cellular, but
    also with areas of mature collagen
  Eval: very advanced
A3
  Somewhat larger necrotic islands with extensive
    old-channel-perfusion-pattern, closely followed
    by live regenerating cells
  The penetration of dead tissue with live regenerating tissue is one of the best seen in all dogs so far
    (→Photo; recut HE since some of these penetration areas could be cut better)
  very active, very vascular granulation tissue
  one focus of calcification (A3)
  vascularity is truely unusual!
  Eval: definately treated
LB3
  Only small focus of granulation tissue looking active
  Questionable increase in vascularity of adjacent
    intact muscle
  Eval: not enough for infarcted area (or healing so
    advanced that it's reflected in the reduced infarct
    size?)
SB3
  Recut and photo! Can't imagine a more desireable
    effect in advanced healing than this.
  Photo
Overall Dog 23: if this was not treated, my criteria
  have to be revised. Rating=5
Gavra's: 11045, 19% Infarct

Dog 24

A1 Anterior, slice one, infarct center
  Large necrotic zone, poorly perfused
  Only occasional polys and nuclear dust
  Only few red blood cells between fibers are fresh,
    rest is old ("ghosts")
  Cellular ingrowth very limited
  Many vessels in granulation tissue are thrombosed
  New tissue mostly cellular with poor collagen organization and multiple foci of calcification
  Poorly organizing fibrinous pericarditis also present
  Much fibrin everywhere in border zone (recent and
    phot) (PTAH overstained, repeat)
  Eval: delayed healing, complications by clotting
A2
  Similar to A1; rim with granulation tissue small and
    immature, only subepicardial
  Cellular ingrowth only 0.5 mm and only along
    larger vessels not well interdigitating (photo)
  Much fibrin in larger channels
  PTAH shows impressive fibrin clot in a larger
    artery
  Eval: delayed healing; possibly perfusion blockage
A3
  Same as A1 and A2 or worse, with early calcification
  Good quality HE for photo of epicardial rim of
    granulation tissue and calcium Thrombosed vessels present, thrombi less than 10, but more than 2 days old
Small island of vascular cells and fibroblasts close to center of necrosis, very immature
Eval: poor healing; thrombotic complications LB3 Lateral border, third slice
Partial fresh perfusion of necrotic material
Ingrowth present but not impressive
Most advanced areas are more cellular than collagenous; much calcification
Preserved muscle shows hydropic changes in borderzone and also subepicardial; otherwise unremarkable and not overly vascularized
Marked chronic and acute pericarditis, with involvement of a few muscle layers underneath
Eval: delayed healing; complication possibly due to infection SB3 Septal border, third slice
Essentially like previous slides, but not epicardium present, and not as much fibrin
Rim with granulation tissue and infiltrating live cells ranges between 0.3 mm and 0.7 mm, much smaller than in other dogs
Eval: delayed, poor healing Overall Dog 24: control, with additional complications (thrombotic and possibly infection) Rating=1

The above pathology reports were graded 1 to 5, with grades 1 and 2 indicating lack of or minimal healing (i.e., suggestive of control treatment), grades 4 and 5 indicating advanced or accelerated healing (i.e., suggestive of effective experimental treatment) and grades 3, 3− or 3+ indicating equivocal results. The grading or rating was done by a pathologist (CH) (Dr. Christian Haudenschild of Boston University School of Medicine) unaware of the treatment received by the dog, and was matched afterward by H. Gavros with the actual treatment. Matching was considered "correct" if experimental dogs were graded 4 or 5 and control dogs were graded 1 or 2, and "mismatched" when the opposite happened. Those graded 3, 3− or 3+ from either group were considered "equivocal". According to this procedure:

Dogs #10, 19, 24 (control and dog #14 (experimental) were graded 1.
Dogs #6, 7, 21 (control) and dog #12 (experimental) were graded 2.
Dogs #1, 13, 22 (experimental) and dog #16 (control) were graded 3.
Dogs #8 and 20 (experimental) and dog #9 (control) were graded 4.
Dogs #11, 17, 23 (experimental) were graded 5.
Dogs #2, 5, 15, and 18 were discarded because their infarcts were too small (see table VII above). Dogs #3 and 4 died before the end of the study.

In total, twenty-four dogs were operated on. Two died, and four were discarded because the infarct was too small. Of the remaining 18, ten were experimental and 8 were controls. Out of these 18, eleven matched correctly (5 experimental and 6 controls), three mismatched (2 experimental and 1 control), and four were equivocal (3 experimental and one control).

| Results: | Correct | Incorrect | Can't Tell |
|---|---|---|---|
| (1) or (5) | 6 | 1 | |
| (2) or (4) | 5 | 2 | |
| (3)− or (3)+ | 2 | 1 | |
| 3 | | | 1 |
| Totals | 13 | 4 | 1 |

Results are seen also for rating by another pathologist Dr. Michael Klibaner (MK) of Boston University in the same manner.

These examples are for illustrative purposes only and are not meant to limit the invention.

EXAMPLE III

VASCULARIZATION OF A HUMAN MYOCARDIAL INFARCT

Four Hematoxilin/Eosin sections from different zones at 40x of the heart of a 78 year old human patient who had several infarcts (FIGS. 25a, b, c, d) show that the mechanisms of vascularization are indeed part of the infarct healing in humans and that regions lacking angiogenesis also lack all signs of subsequent healing mechanisms such as cellular organization and collagenization. This patient has not been treated with the omental extract (CMFr).

Figure 25A:
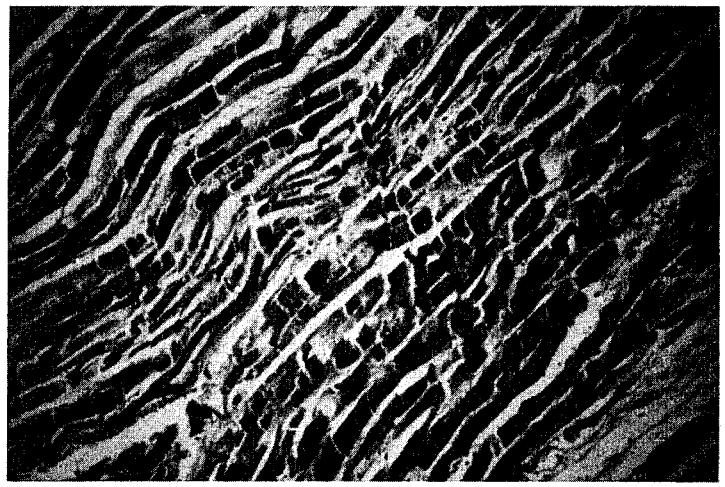

FIG. 25(A) Human myocardial infarct. Necrotic center zone, not vascularized.

In surviving patients, such areas can remain present for a long time. Without vascularization, cells which would dissolve or phagocytize these dead muscle cells arrive late or not at all; regenerating cells also have little access to nonvascularized areas.

Figure 25B:

FIG. 25(B) Human myocardial infarct. Necrotic zone, vascularized.

In the vicinity of blood vessels, abundant blood-borne round cells can be seen as blue dots between the dead heart muscle cells. In surviving patients, such cells would be followed later by regenerating cells which lay down collagen to form a scar of sufficient mechanical strength.

Figure 25C:
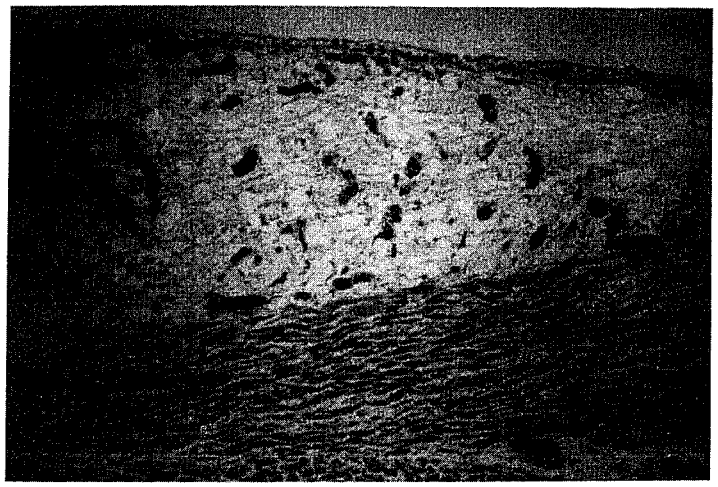
Figure 25D:
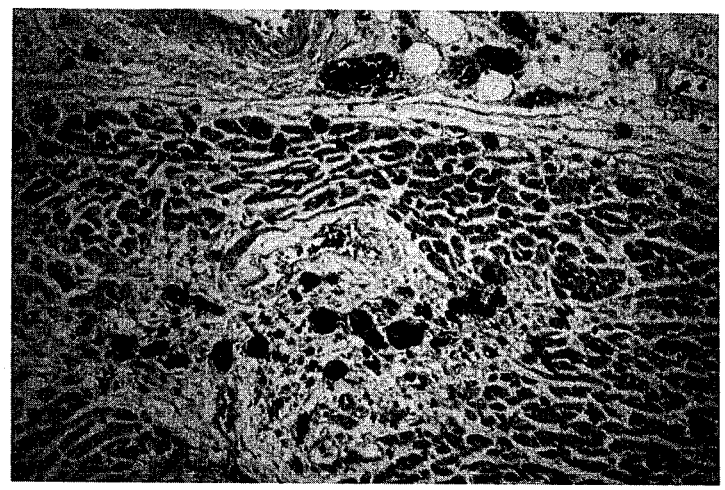

FIG. 25(C) Human myocardial infarct. Vascular reactive epicardium.

The epicardium, a thin covering layer of the heart muscle, reacts to an underlying infarct with new vessel growth such as seen in this micrograph: tortuous channels filled with red blood cells within loose tissue represent new blood vessels. Such vessels can be the source of revascularization of the infarcted heart muscle. The epicardium, lining the space around the heart, shares this potential for vascularization with similar layers lining other spaces around lungs or intestines. In the latter, the peritoneal space, the omentum as well as the serosa layer around the peritoneal organs react strongly and quickly with neovascularization.

25(D) Spontaneous vascularization in human myocardial infarct of microscopic size.

In the round area in the center of this micrograph, a few heart muscle cells have been lost. This focus is small enough to be rapidly and entirely filled with new vessels, which are not only spaced more densely, but also better perfused. Note that this focus incidentally is located underneath the epicardium which also shows a vascular reaction. Vascularization is a normal and essential step in the spontaneous healing process. Large necrotic zones, however, are often poorly vascularized and therefore not effectively populated by living cells necessary for the healing.

The invention claims to reduce such zones.

EXAMPLE IV
DOG MI

Figure 26A:
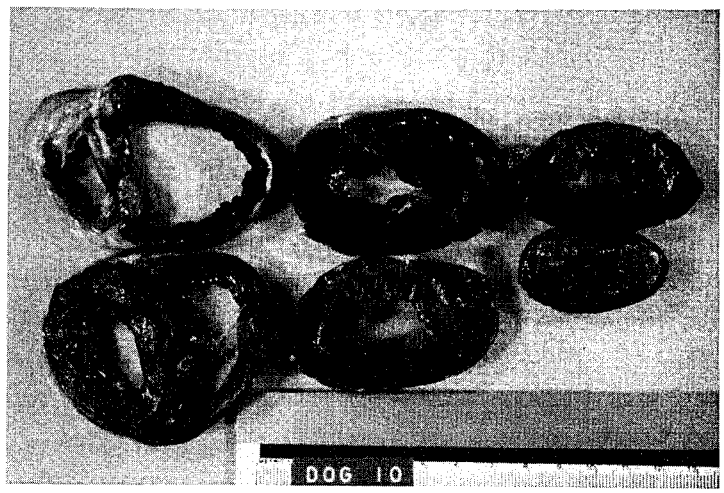
Figure 26B:
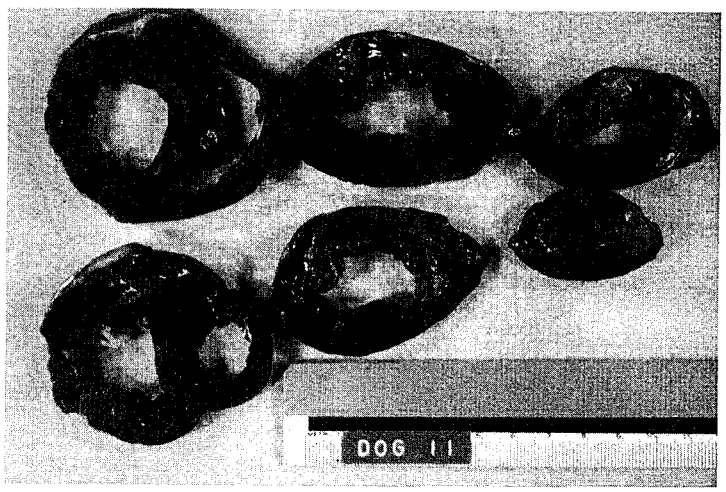

FIG. 26: Gross photos of all standard slices through the heart ventricles of two dogs. The difference between infarcted and normal muscle is enhanced by an enzyme reaction which stains live muscle blueish; infarcted areas remain unstained and show their whitish color with red blood spots. Some areas in the first slice (upper left) are white because of the beginning of the valve area; these are not infarcted.

Microscopic sections are usually taken from slice #4 (lower middle in these photos) at: A-(anterior, center of infarct, top of the slice in these photos), P-(posterior, unaffected control muscle), and L (laterial free wall of left ventricle, important border zone between infarct and normal tissue, needs sometimes several sections). These pathologic readings were done as a blind test.

These infarcts are produced by total ligation of the left anterior coronary artery. Ten days later, at the time of evaluation, the size of the infarcts should be similar for dogs #10 (untreated control), and #11 (treated), since at this time the size is mainly determined by the area supplied by the ligated coronary artery, not by the extent or effectiveness of the healing. Due to anatomical and technical variability between individual dogs and ligations, infarct size at this time is a poor evaluation criterium for treatment effects; it is only measured to assure that reasonable basic conditions exist for all experiments, meaning that at least 9% of the ventricular muscle mass should be infarcted. (This represents at least half of the area which the ligated coronary artery usually supplies, within the limits of individual anatomic variations. Once the extent of this variation is known, the morphometric determination of the scar size may be a meaningful way of assessing the healing process at a later time point. From the first set of dogs 8 were usable with adequate infarcts: 5 experimental and 3 controls. Of the experiment, 4 were recognized and one was indifferent, and of the 3 controls 2 were recognized and one was considered experimental. In at least one experimental animal with 16% MI qualitatively unusual prominence of vessels was seen.

Figure 27A:
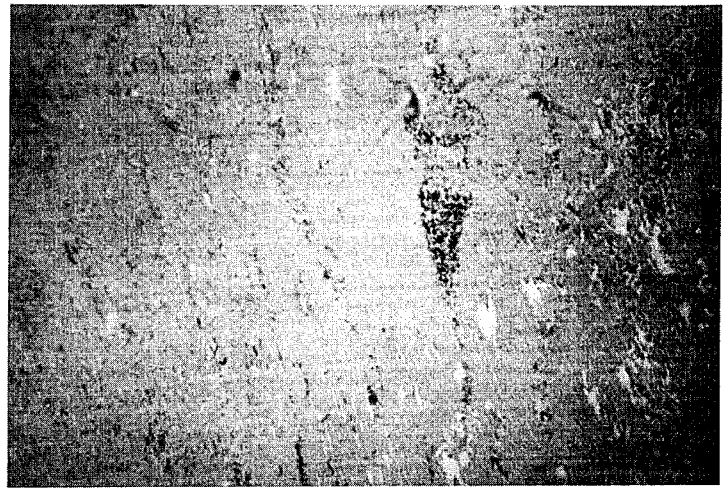
Figure 27B:
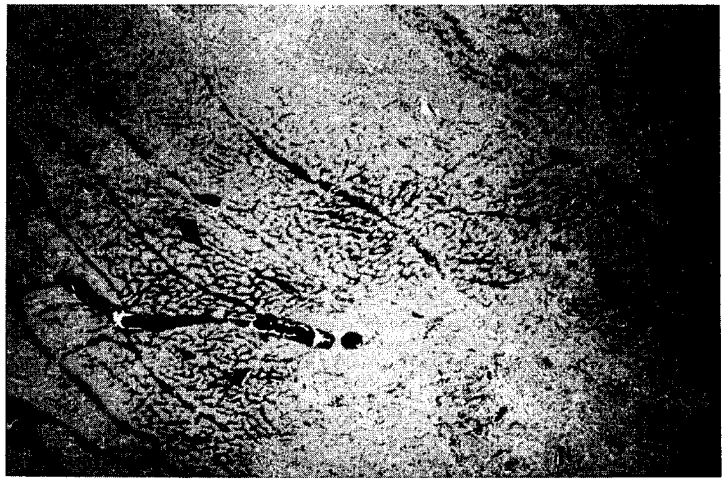

FIG. 27: Necrotic Area (2A: dog #10 control 2B dog #11 treated)

Low power micrographs (16x) of the center of the infarct. All pink background is dead muscle. The red dots and lines represent blood, some of which is fresh (i.e. not clotted or hemolyzed). The pattern in the treated dog #11 apparently follows the original capillary and larger vessel channels, although together with the heart muscle cells the respective vascular cells must have died too in this area. The pattern is unusual and not seen to this extent in controls such as dog #10. Diffuse bleeding into the infarct is more likely to be expected, and at other places, both in controls and treated animals, small hemorrhages do indeed occur.

Figure 28A:
Figure 28B:

FIG. 28: Border of infarct

Similar differences between treated (Dog #12) and untreated (Dog #10) samples are seen: vascularity is more intense in the sample from Dog #12. Both fresh blood and fibrin (bright red) are present in the vascular lumina.

The red lines or vascular channels at the periphery of the infarct, represent the positions where the first living cells, either white cells from the blood or regenerating larger tissue cells, can be seen. It is easy to imagine that the faster and more numerous the new vessels arise, the greater is the chance that they can follow and possibly connect with the old channels. Perfusion is a desired healing step, but bleeding may not be. The perfusion of old channels is also seen in controls (A) but so far, it was more impressive in treated animals.

Figure 29A:
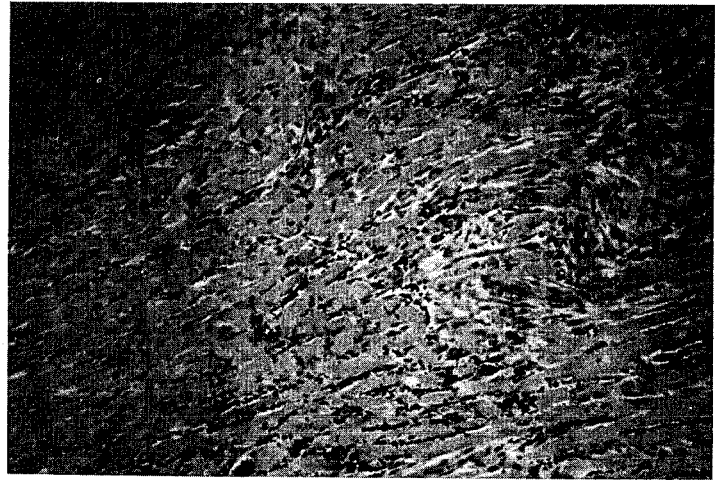
Figure 29B:
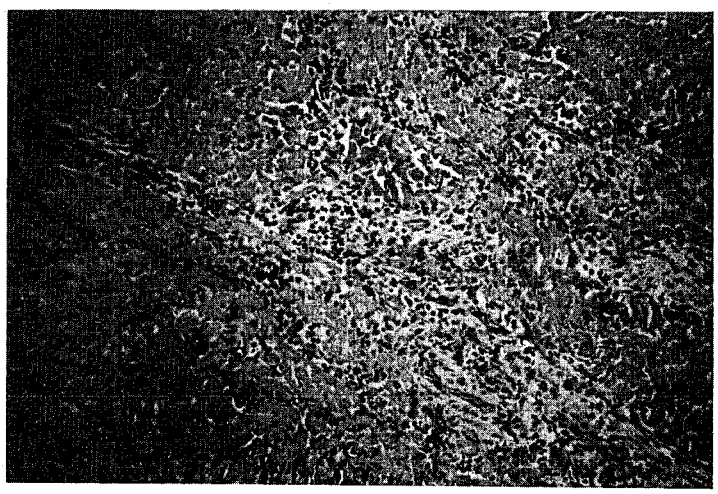

FIG. 29: Border of Infarct

Higher power micrographs (40x) at the edge of the most active cellular regeneration. Of interest are the larger purple dots or ellipsoids which represent nuclei of living regenerating cells. These cells follow the meshwork of old vascular channels which are seen here in both pictures. In the control micrograph (dog #10), most of the regenerating cells are in the left lower corner; in the micrograph of the treated animal (dog #11), the regenerating cells are throughout all channels between the dead (gray) muscle cells, and are intermixed with smaller round cells and neutrophils. Pictures like this illustrate important details, but are not too suitable as evidence of differences, since only a millimeter away from this position, there may be many more living cells in either specimen showing a kind of gradient of cellularity. The overall evaluation by one or several experienced pathologists is therefore of importance.

Figure 30A:
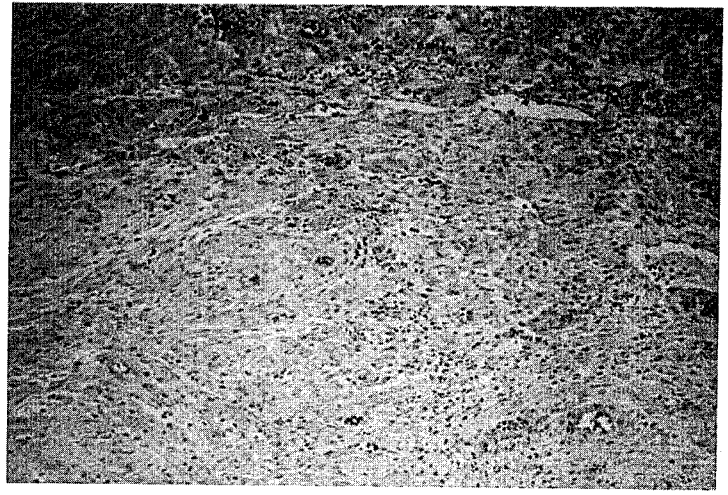
Figure 30B:
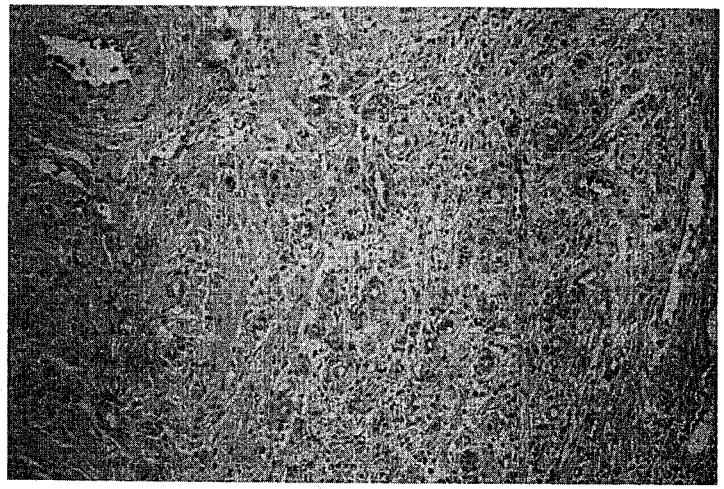

FIG. 30: Regenerating Border

These relatively pale HE stained sections are taken from an earlier series of experiments (dog 7 control, dog 8 treated). They are selected to show exactly the border line of the infarct (40x). In the control, the infarcted area is a small rim of slightly pinker muscle cells at the top of the picture; in the treated specimen, the infarct is represented by a few pink muscle cells at the right side of the picture. The rest of both micrographs contain living, regenerating cells. Circular structures and some elongated slits represent new blood vessels, which are more prominent in the photo from the treated animal. This photo incidently also shows a preexisting coronary artery branch in the upper left corner.

Figure 31:
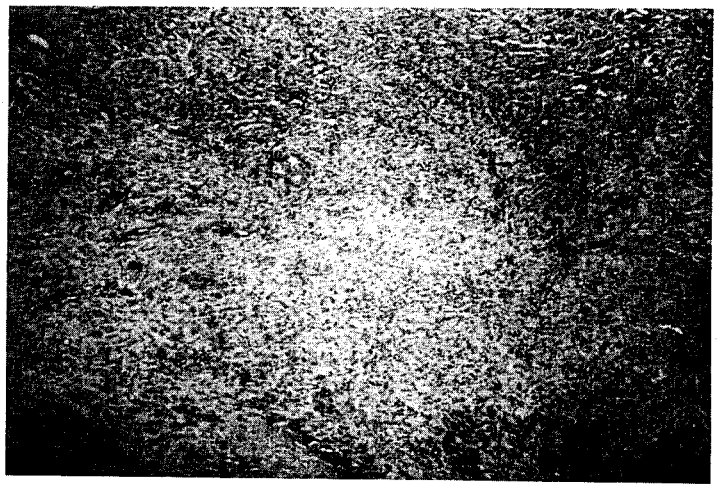

FIG. 31: Cellular reaction

Low power micrographs (16x) to demonstrate that over large areas virtually no differences can be seen. The treated specimen may show a little more collagen (green) than the control. Only the combined impressions from many fields in multiple sections by one or preferentially several trained pathologists may yield conclusive results.

Figure 32A:
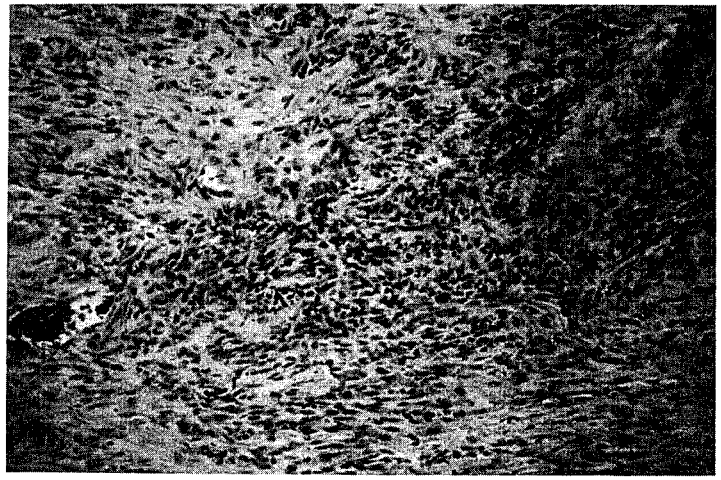
Figure 32B:
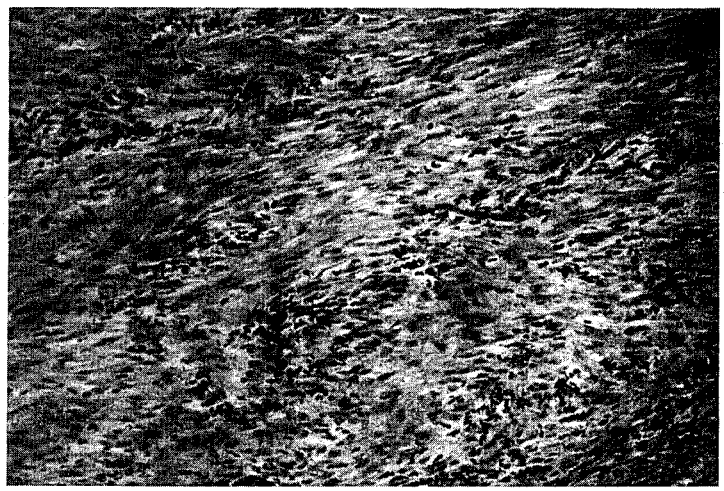

FIG. 32: Most advanced healing

Searching for the area with the absolutely most advanced collagenous organization in each section provided the most impressive differences (40x). All cells in these pictures are living regenerating cells; nor heart muscle cells are present. Collagen stains green. The greenest area in the section from Dog #10 is very cellular, and vessels can also be seen. In dog #12 (treated), the green areas are prominent, and within these areas the cellularity is reduced. When the organization will be completed, most of the cells which have produced the collagen and also most vessels will disappear. Thus this area in the treated animal can safely be interpreted as advanced organization. The more such highly organized collagen is present the higher is the tensile strength of the developing scar and the lower is the risk of rupture. It is only one goal of the treatment to achieve such tensile strength and advanced organization very early and thus to prevent rupture. Relatively few MI patients die from rupture. However, this advanced healing and organization at this time point also indicates that all preceding healing event leading to this scar must have been accelerated; thus the degree of collagenization is an indicator for the success of previous desirable, but not so easily measurable healing events, which determine the function and performance of the surviving hearts as well as a possibly lower rish of reinfarction.

Figure 33A:
Figure 33B:
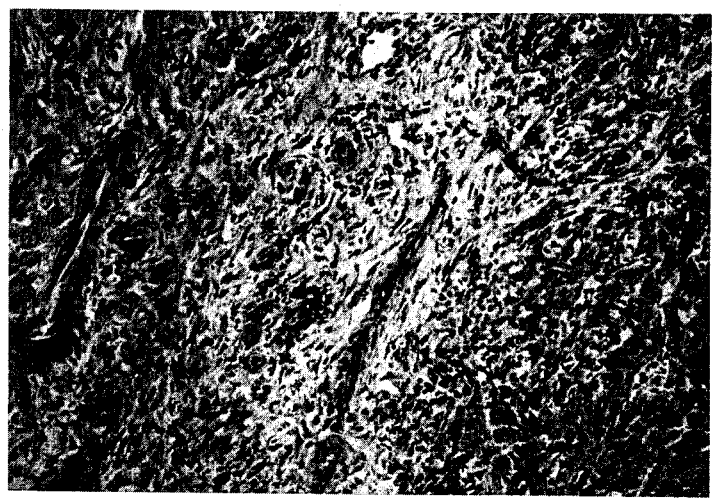

FIG. 33: Advanced healing and active healing (40x)

These micrographs are from two different dogs, both treated. One shows an area of relatively even distribution of regenerating cells and collagen (A), the other (B) a gradient ranging from highly organized collagen (green, right) to dead heart muscle (gray, left), with abundant vessels (Everywhere) and high cellularity. Both patterns appear to represent desirable, active healing processes.

Example V

In a final analysis by two pathologists Dr. Christian Haudenschild (C. H.) and Dr. Michael Klibaner (M. K.) of the Cardiovascular Research Laboratory, Boston University School of Medicine, Boston, Mass. of the dog myocardial infarcts blind evaluations of experimental and control animals were done by both reviewers independently as above. See table VIII. For this second analysis, the early, balloon occluded dogs (1–5) were not included, but all following areas (6–24) were, regardless of the size of the infarct, resulting in 19 evaluations.

Agreement between CH and MK was found in 12 of 19 animals and of these 12, both were correct as to 9 dogs and both were wrong as to 3 dogs (#9, 13, 16). Disagreement between CH and MK was found in 7 of 19 animals and of these 7, CH was correct for 4 and MK was correct for 3.

Therefore the correct calls in analysis of 19 dogs by CH were 13/19 consisting of 6/9 controls and 7/10 experimental and the correct calls for MK were in 12 of 19 consisting of 4 of 9 controls and 8 of 10 experiments. The incorrect calls for CH totalled 6 i.e. 3 of 9 control animals were called as treated and 3 of 10 treated animals were called as controls. The incorrect calls for MK totalled 7 i.e. 5 of 9 control animals were called as treated and 2 of 10 treated animals were called as controls. This data is summarized in the following Table IX where these 19 dogs are evaluated and compared. Also included in the following tables is dog #5, for which one evaluation (MK) and one non-evaluation (i.e. 3, without guess + or-). Thus these tables total 20 dogs. From Table IX is seen the CH correct calls were 14/20 and for MK 13/20 (including dog #5).

TABLE VIII

MATCHED EVALUATION OF MYOCARDIAL INFARCTS IN DOGS

| DOG # | MK | CH | E/C | MATCH* | RIGHT (R)/ WRONG (W) |
|---|---|---|---|---|---|
| 5 | 5 | 3 | E | N | R̲ |
| 6 | 1 | 2 | C | CM | R |
| 7 | 1 | 2 | C | CM | R |
| 8 | 4 | 4 | E | PM | R |
| 9 | 4 | 4 | C | PM | W |
| 10 | 3+ | 1 | C | N− | R̲ |
| 11 | 4 | 5 | E | CM | R |
| 12 | 3+ | 2 | E | N− | W̲ |
| 13 | 2 | 3+ | E | N− | W̲ |
| 14 | 3+ | 1 | E | N− | W̲ |
| 15 | 1 | 3+ | C | N− | R̲ |
| 16 | 4 | 3+ | C | N+ | W̲ |
| 17 | 5 | 5 | E | PM | R |
| 18 | 3+ | 5 | E | N+ | R |
| 19 | 5 | 1 | C | MMM | — |
| 20 | 5 | 4 | E | CM | R |
| 21 | 3+ | 2 | C | N− | R |
| 22 | 1 | 3+ | E | N | R̲ |
| 23 | 5 | 5 | E | PM | R̲ |
| 24 | 2 | 1 | C | CM | R |

LEGEND to Table VIII:
*PM - Perfect Match
CM - Close Match - off by 1
N - Non-Match
MM - Mismatch - off by 3
MMM - Complete Missmatch - off by 4
PM - 4  3 Right  1 Wrong
CM - 5  5 Right  0 Wrong
N - 10  6 Right  4 Wrong
NM - 0
MMM - 1
Under MK is shown the rating by M.K. and under CH is shown the rating by C.H.
E/C = experimental or control.
R̲ or W̲ = non-match
There were 9 matches PM or CM of which 8 were right and 1 was wrong.
There was only 1 complete MMM.

TABLE IX

| COMPARISON OF PATHOLOGISTS' RATINGS | | | | |
|---|---|---|---|---|
| | MK | | CH | |
| | R | W | R | W |
| 1 | 3 | 1 | 3 | 1 |
| 2 | 1 | 1 | 3 | 1 |
| 3− | | | | |
| 3 | | | 1 | |
| 3+ | 3 | 2 | 2 | 2 |
| 4 | 2 | 2 | 2 | 1 |
| 5 | $\frac{4}{13}$ | $\frac{1}{7}$ | $\frac{4}{14}$ 1 | $\frac{0}{5}$ |
| 1 | 3 | 1 | 3 | |
| 5 | $\frac{4}{7}$ | $\frac{1}{2}$ | $\frac{4}{7}$ | $\frac{0}{1}$ |
| 2 | 1 | 1 | 3 | 1 |
| 4 | $\frac{2}{3}$ | $\frac{2}{3}$ | $\frac{2}{5}$ | $\frac{1}{2}$ |
| 3 | 3 | 2 | 1 | 2 |

The 1 & 5 are very significant for both MK & CH. The 2 & 4 look random for MK but significant for CH.

What is claimed:

1. Composition for the treatment of angina, a myocardial ischemic lesion, or a myocardial infarct in a human having angina, a myocardial infarct or a myocardial ischemic lesion consisting essentially of a pharmacologically active mixture of lipid and ganglioside derived from the omentum by extraction with at least one organic solvent.

2. Composition for the treatment of angina, a myocardial ischemic lesion, or a myocardial infarct in a human having angina, a myocardial infarct or a myocardial ischemic lesion wherein the composition consists essentially of pharmacologically active lipid material.

3. Composition for the treatment of angina, a myocardial ischemic lesion, or a myocardial infarct in a human having angina, a myocardial infarct or a myocardial ischemic lesion wherein the composition consists essentially of pharmacologically active ganglioside material.

4. Composition of claim 1 wherein the omentum lipid mixture is a physiologically active chloroform methanol extract of omentum.

5. Composition of claim 1 wherein the omentum mixture is a physiologically active hexane-ethanol extract.

6. Composition of claim 5 wherein the hexane-ethanol extract is derived from further extraction of the chloroform-methanol extract.

7. Composition of claim 1 wherein the composition is a physiologically active supercritical gas extract of omentum.

8. Composition of claim 1, 2 or 3, wherein the essentially ganglioside, lipid or ganglioside-lipid-omental material leads to improved vascularization and collateralization in angina, a myocardial ischemic lesion or a myocardial infarction and tissue bordering the infarction.

9. Composition of claim 1, 2 or 3, wherein the essentially ganglioside, lipid or ganglioside-lipid-omental material leads to improved vascularization and collateralization allowing improved myocardial perfusion in angina, a myocardial ischemic lesion, or a myocardial infarction and tissue bordering the infarction.

10. Composition of claims 1, 2 or 3, wherein the essentially ganglioside, lipid or ganglioside-lipid-omental material leads to improvement of myocardial perfusion in angina, a myocardial ischemic lesion, a myocardial infarction or tissue bordering the infarction.

11. Composition of claim 1, 2 or 3, wherein the essentially ganglioside, lipid or ganglioside-lipid-omental material leads to increased or accelerated organization and collagenization in angina, a myocardial ischemic lesion, or a myocardial infarction.

12. Composition of claim 1, 2 or 3, wherein the essentially ganglioside, lipid or ganglioside-lipid-omental material leads to improvement of vascularization and perfusion in a transplanted heart.

13. Composition of claims 1, 2 or 3, wherein the essentially ganglioside, lipid, or ganglioside-lipid-omental material leads to improvement of a vascular bed supplied by an aortic and peripheral vascular and cardiac coronary graft and in a vessel reopened by techniques such as but not limited to angioplasty.

14. Composition of claims 1, 2 or 3, wherein the essentially ganglioside, lipid or ganglioside-lipid-omental material leads to increased perfusion, vascularization and collateralization, organization and collagenization in angina, a myocardial ischemic lesion, and a myocardial infarct in humans.

15. Method for the treatment of angina, a myocardial ischemic lesion or a myocardial infarction condition in a patient having angina, a myocardial infarct or a myocardial ischemic lesion which comprises using physiologically active amounts of a mixture of isolated lipid and ganglioside material derived from the omentum by extraction with at least one organic solvent in a physiologically active amount sufficient to observe enhanced perfusion, vascularization or collateralization in said condition.

16. Method of claim 15 wherein the omentum derived material consists essentially of lipid.

17. Method of claim 15 wherein the omentum derived material consists essentially of ganglioside.

18. Method of claim 15 wherein the physiologically active extract is a chloroform-methanol extract.

19. Method of claim 15 wherein the physiologically active extract is a hexane-ethanol extract.

20. Method of claim 19 wherein the physiologically active extract is a hexane-ethanol extract derived from the chloroform-methanol extract.

21. Method for the treatment of angina, a myocardial ischemic lesion or a myocardial infarction condition in a patient having angina, a myocardial infarct or a myocardial ischemic lesion which comprises using physiologically active amounts of a mixture of a purified lipid and ganglioside.

22. Method of claim 21 wherein the physiologically active material consists essentially of lipid.

23. Method of claim 21 wherein the physiologically active material consists essentially of ganglioside.

24. Method of claims 15, 16, 17, 21, 22 or 23 wherein the essentially ganglioside, lipid or lipid-ganglioside material enhances perfusion in said conditions.

25. Method of claims 15, 16, 17, 21, 22 or 23 wherein the essentially ganglioside, lipid or lipid-ganglioside material improves collagenation in said conditions.

26. Method of claims 15, 16, 17, 21, 22 or 23 wherein the essentially ganglioside, lipid or lipid-ganglioside material leads to improved scar formation in said conditions.

27. Method of claims 16, 17, 17, 21, 22 or 24 wherein the essentially ganglioside, lipid or lipid-ganglioside material leads to improvement of vascularization, collateralization and perfusion in a transplanted heart.

28. Method of claims 15, 16, 17, 21, 22 or 23 wherein the essentially ganglioside, lipid or lipid-ganglioside material leads to improvement of a vascular bed supplied by an aortic, a peripheral vascular graft, a cardiac coronary graft and in a vessel reopened by techniques such as but not limited to angioplasty.

* * * * *

UNITED STATES PATENT AND TRADEMARK OFFICE
CERTIFICATE OF CORRECTION

PATENT NO. : 4,778,787

DATED : October 18, 1988

INVENTOR(S) : Catsimpoolas et al.

It is certified that error appears in the above-identified patent and that said Letters Patent is hereby corrected as shown below:

| | |
|---|---|
| Col. 6, line 5: | change "chromotography" to -- chromatography --. |
| Col. 9, line 25: | change "Glc/Gal/NaCGal" to -- Glc/Gal/NAcGal --. |
| Col. 14, line 14: | change "8.72" to -- 28.72 --. |
| Col. 14, line 41: (first col. from left in Table III) | after "sol" delete "11". |
| Col. 14, line 43: | after "MeOH" delete "11". |
| Col. 17, line 15: | change "Porcino" to -- Porcine --. |
| Col. 17, line 56: | after "graph" delete ")". |
| Col. 17, lines 58 & 60: | change "platted" to -- plotted --. |
| Col. 25, line 17: | change "salinee" to -- saline --. |
| Col. 30, line 39: | change "enter" to -- center --. |
| Col. 31, line 57: | insert before "Dog 8 10595" -- Photo 15: typical organizing pattern with fibroblasts. --. |

UNITED STATES PATENT AND TRADEMARK OFFICE
CERTIFICATE OF CORRECTION

PATENT NO. : 4,778,787

DATED : October 18, 1988

INVENTOR(S) : Catsimpoolas et al.

It is certified that error appears in the above-identified patent and that said Letters Patent is hereby corrected as shown below:

| | |
|---|---|
| Col. 33, line 45: | change "F Dog. 333" to -- Dog 633 --. |
| Col. 40, line 52: | change "Unnusual" to -- Unusual --. |
| Col. 41, line 62: | change "may" to -- many --. |
| Col. 47, line 15: | change "rish" to -- risk --. |
| Col. 48, line 29: | delete "NM" and insert -- MM --. |
| Claim 27, line 1: | change "16, 17, 17, 21, 22 or 24" to -- 15, 16, 17, 21, 22 or 23 --. |

Signed and Sealed this

Thirty-first Day of October, 1989

Attest:

DONALD J. QUIGG

*Attesting Officer*

*Commissioner of Patents and Trademarks*